(12) United States Patent
Saborio et al.

(10) Patent No.: US 7,803,910 B2
(45) Date of Patent: Sep. 28, 2010

(54) SOLUBLE CD164 POLYPEPTIDES

(75) Inventors: Gabriela Saborio, Dingy en Vuache (FR); Christine Power, Thoiry (FR); Amanda Proudfoot, Chens sur Leman (FR)

(73) Assignee: Merck Serono S.A., Coinsins, Vaud (CH)

( * ) Notice: Subject to any disclaimer, the term of this patent is extended or adjusted under 35 U.S.C. 154(b) by 75 days.

(21) Appl. No.: 11/814,389

(22) PCT Filed: Jan. 24, 2006

(86) PCT No.: PCT/EP2006/050422

§ 371 (c)(1),
(2), (4) Date: Jul. 20, 2007

(87) PCT Pub. No.: WO2006/077266

PCT Pub. Date: Jul. 27, 2006

(65) Prior Publication Data

US 2008/0131437 A1 Jun. 5, 2008

Related U.S. Application Data

(60) Provisional application No. 60/655,382, filed on Feb. 23, 2005.

(30) Foreign Application Priority Data

Jan. 24, 2005 (EP) .................................. 05100432

(51) Int. Cl.
*C07K 14/00* (2006.01)
(52) U.S. Cl. ..................................................... 530/350
(58) Field of Classification Search ........................ None
See application file for complete search history.

(56) References Cited

FOREIGN PATENT DOCUMENTS

WO WO 02/098917 A2 12/2002
WO WO 2005/011728 A2 2/2005

OTHER PUBLICATIONS

Burgess et al J Cell Biol. 111:2129-2138, 1990.*
Mikayama et al. PNAS, 1993. 90: 10056-10060.*
Wang et al. (JBC, 2001 276:49213-49220.*
Whisstock et al ( Quarterly Review of Biophysics, 2003, 36, pp. 307-340.*
Altschul, S. F. et al. "Basic Local Alignment Search Tool" *J. Mol. Biol.*, 1990, pp. 403-410, vol. 215.
Altschul, S. F. et al. "Gapped BLAST and PSI-BLAST: A New Generation of Protein Database Search Programs" *Nucleic Acids Research*, 1997, pp. 3389-3402, vol. 25, No. 17.
Anthony-Cahill, S. J. et al. "Expanding the Natural Repertoire of Protein Structure and Function" *Current Pharmaceutical Biotechnology*, 2002, pp. 299-315, vol. 3.
Brown, A. R. et al. "The Total Chemical Synthesis of Monocyte Chemotactic Protein-1 (MCP-1)" *Journal of Peptide Science*, 1996, pp. 40-46, vol. 2.
Brutlag, D. L. et al. "Improved Sensitivity of Biological Sequence Database Searches" *CABIOS*, 1990, pp. 237-245, vol. 6, No. 3.
Casi, G. et al. "Convergent Protein Synthesis" *Current Opinion in Structural Biology*, 2003, pp. 589-594, vol. 13.
Chai, H. et al. "Glycosylation and High-Level Secretion of Human Tumour Necrosis Factor-β in Recombinant Baculovirus-Infected Insect Cells" *Biotechnol. Appl. Biochem.*, 1993, pp. 259-273, vol. 18.
Chan, J. Y.-H. et al. "Relationship between Novel Isoforms, Functionally Important Domains, and Subcellular Distribution of CD164/Endolyn" *The Journal of Biological Chemistry*, 2001, pp. 2139-2152, vol. 276, No. 3.
Cleland, J. L. et al. "Emerging Protein Delivery Methods" *Current Opinion in Biotechnology*, 2001, pp. 212-219, vol. 12.
Database WPI, Section Ch, Week 199434, Derwent Publications Ltd., London, GB, AN 1994-275519, Jul. 26, 1994, XP002336021.
Dougherty, D. A. "Unnatural Amino Acids as Probes of Protein Structure and Function" *Current Opinion in Chemical Biology*, 2000, pp. 645-652, vol. 4.
Doyonnas, R. et al. "CD164 Monoclonal Antibodies that Block Hemopoietic Progenitor Cell Adhesion and Proliferation Interact with the First Mucin Domain of the CD164 Receptor" *The Journal of Immunology*, 2000, pp. 840-851, vol. 165.
Feldman, L. J. et al. "Adenovirus-Mediated Arterial Gene Therapy for Restenosis: Problems and Perspectives" *Semin Intervent Cardiol*, 1996, pp. 203-208, vol. 1.
Gish, W. et al. "Identification of Protein Coding Regions by Database Similarity Search" *Nature Genetics*, Mar. 1993, pp. 266-272, vol. 3.
Golebiowski, A. et al. "High-Throughput Organic Synthesis of Peptide Mimetics" *Current Opinion in Drug Discovery & Development*, 2001, pp. 428-434, vol. 4, No. 4.
Gonnet, G. H. et al. "Exhaustive Matching of the Entire Protein Sequence Database" *Science*, Jun. 5, 1992, pp. 1443-1445, vol. 256.
Grantham, R. "Amino Acid Difference Formula to Help Explain Protein Evolution" *Science*, pp. 862-864, vol. 185.
Gustafsson, C. et al. "Codon Bias and Heterologous Protein Expression" *Trends in Biotechnology*, Jul. 2004, pp. 346-353, vol. 22, No. 7.
Hanson, L. A. et al. "Anti-Inflammatory Capacities of Human Milk: Lactoferrin and Secretory IgA Inhibit Endotoxin-Induced Cytokine Release" In *Advances in Mucosal Immunology*, ed. J. Mestecky et al., 1995, pp. 669-672, Plenum Press, New York.
Henikoff, S. et al. "Performance Evaluation of Amino Acid Substitution Matrices" *Proteins: Structure, Function, and Genetics*, 1993, pp. 49-61, vol. 17.
Higgins, D. G. et al. "Using CLUSTAL for Multiple Sequence Alignments" *Methods in Enzymology*, 1996, pp. 383-402, vol. 266.
Hruby, V. J. et al. "Conformational and Topographical Considerations in Designing Agonist Peptidomimetics from Peptide Leads" *Current Medicinal Chemistry*, 2000, pp. 945-970, vol. 7.

(Continued)

*Primary Examiner*—Michail A Belyavskyi
(74) *Attorney, Agent, or Firm*—Saliwanchik, Lloyd & Saliwanchik

(57) ABSTRACT

The present invention relates to sCD164 variants and therapeutic uses thereof, in particular for treating or preventing inflammatory or autoimmune disorders.

8 Claims, 22 Drawing Sheets

OTHER PUBLICATIONS

Karlin, S. et al. "Methods for Assessing the Statistical Significance of Molecular Sequence Features by Using General Scoring Schemes" *Proc. Natl. Acad. Sci. USA*, Mar. 1990, pp. 2264-2268, vol. 87.

Küsters, S. et al. "Interferon Gamma Plays a Critical Role in T Cell-Dependent Liver Injury in Mice Initiated by Concanavalin A" *Gastroenterology*, 1996, pp. 462-471, vol. 111.

Lee, Y.-N. et al. "Identification of a Role for the Sialomucin CD164 in Myogenic Differentiation by Signal Sequence Trapping in Yeast" *Molecular and Cellular Biology*, Nov. 2001, pp. 7696-7706, vol. 21, No. 22.

Lenhard, T. et al. "A New Set of Versatile Vectors for the Heterologous Expression of Foreign Genes Using the Baculovirus System" *Gene*, 1996, pp. 187-190, vol. 169.

Luo, Y. et al. "Novel Biomaterials for Drug Delivery" *Expert Opin. Ther. Patents*, 2001, pp. 1395-1410, vol. 11, No. 9.

Matsui, T. et al. "The Ratio of Splicing Variants of MGC-24/CD164, a Sialomucin, Correlates with the Metastatic Potential of Colorectal Carcinomas" *J. Biochem.*, 2000, pp. 1103-1107, vol. 127.

Muir, T. W. "Semisynthesis of Proteins by Expressed Protein Ligation" *Annu. Rev. Biochem.*, 2003, pp. 249-289, vol. 72.

Nicolau, C. et al. "Liposomes as Carriers for in Vivo Gene Transfer and Expression" *Methods in Enzymology*, 1987, pp. 157-176, vol. 149.

Ohno, T. et al. "Gene Therapy for Vascular Smooth Muscle Cell Proliferation After Arterial Injury" *Science*, Aug. 5, 1994, pp. 781-784, vol. 265.

Pearson, W. R. et al. "Improved Tools for Biological Sequence Comparison" *Proc. Natl. Acad. Sci. USA*, Apr. 1988, pp. 2444-2448, vol. 85.

Pillai, O. et al. "Polymers in Drug Delivery" *Current Opinion in Chemical Biology*, 2001, pp. 447-451, vol. 5.

Seino, K.-I. et al. "Protection Against Fas-Mediated and Tumor Necrosis Factor Receptor 1-Mediated Liver Injury by Blockade of FADD without Loss of Nuclear Factor-κB Activation" *Annals of Surgery*, 2001, pp. 681-688, vol. 234, No. 5.

Tascon, R. E. et al. "Vaccination Against Tuberculosis by DNA Injection" *Nature Medicine*, Aug. 1996, pp. 888-892, vol. 2, No. 8.

Thompson, J. D. et al. "CLUSTAL W: Improving the Sensitivity of Progressive Multiple Sequence Alignment Through Sequence Weighting, Position-Specific Gap Penalties and Weight Matrix Choice" *Nucleic Acids Research*, Jan. 1994, pp. 4673-4680, vol. 22, No. 22.

Toyonaga, T. et al. "Chronic Active Hepatitis in Transgenic Mice Expressing Interferon-γ in the Liver" *Proc. Natl. Acad. Sci. USA*, Jan. 1994, pp. 614-618, vol. 91.

Villain, M. et al. "Covalent Capture: A New Tool for the Purification of Synthetic and Recombinant Polypeptides" *Chemistry & Biology*, 2001, pp. 673-679, vol. 8.

Vlasak, R. et al. "Nucleotide Sequence of Cloned cDNA Coding for Honeybee Prepromelittin" *Eur. J. Biochem.*, 1983, pp. 123-126, vol. 135.

Watt, S. M. et al. "CD164, A Novel Sialomucin on CD34$^+$ and Erythroid Subsets, Is Located on Human Chromosome 6q21" *Blood*, Aug. 1, 1998, pp. 849-866, vol. 92, No. 3.

Watt, S. M. et al. "CD164—A Novel Sialomucin on CD34$^+$ Cells" *Leukemia and Lymphoma*, 2000, pp. 1-25, vol. 37, Nos. 1-2.

Wong, T.-K. et al. "Appearance of β-lactamase Activity in Animal Cells Upon Liposome-Mediated Gene Transfer" *Gene*, 1980, pp. 87-94, vol. 10.

Zannettino, A. C. W. et al. "The Sialomucin CD164 (MGC-24v) Is an Adhesive Glycoprotein Expressed by Human Hematopoietic Progenitors and Bone Marrow Stromal Cells that Serves as a Potent Negative Regulator of Hematopoiesis" *Blood*, Oct. 15, 1998, pp. 2613-2628, vol. 92, No. 8.

Zannettino, A. C. W. "CD164" *J Biol Regul Homeost Agents*, 2001, pp. 394-396, vol. 15.

* cited by examiner

| Name | Exon EC dom | Length | Theo MW Da | Sequence ID number |
|---|---|---|---|---|
| Ex4,5,6 | 4,5,6 | 53 | 6172 | 1 |
| Δ1,2,3 | 3,4,5,6 | 77 | 8754 | 2 |
| Ex1 | 1 | 35 | 4406 | 3 |
| Ex1,6 | 1,6 | 56 | 6611 | 4 |
| Ex1,4,6 | 1,4,6 | 69 | 7838 | 5 |
| Δ2,3 | 1,4,5,6 | 88 | 9738 | 6 |
| Δ2 | 1,3,4,5,6 | 112 | 12320 | 7 |
| Δ4 | 1,2,3,5,6 | 127 | 14234 | 8 |
| Ex1,2,3 | 1,2,3 | 87 | 10130 | 9 |
| Δ4,5 | 1,2,3,6 | 108 | 12334 | 10 |
| Δ6 | 1,2,3,4,5 | 119 | 13257 | 11 |
| Δ5 | 1,2,3,4,6 | 121 | 13561 | 12 |
| A22E,G80E | 1,2,3,4,5,6 | 140 | 15592 | 13 |
| N9A,N18A | 1,2,3,4,5,6 | 140 | 15462 | 14 |
| sCD164 | 1,2,3,4,5,6 | 140 | 15462 | 15 |
| sCD164-Fc | 1,2,3,4,5,6-Fc | 372 | 40745 | 16 |
| sCD164-Fcm | 1,2,3,4,5,6-Fc | 372 | 40739 | 18 |

Fig. 2

| Variant | Emax | EC50 nM | | | | | |
|---|---|---|---|---|---|---|---|
| | | IFNg | TNFa | IL-2 | IL-4 | IL-5 | IL-10 |
| sCD164 | >95% | 8.25 | 10.5 | 5.75 | 6.5 | 14.8 | 6.6 |
| Ex1,2,3 | 70% | - | - | 60 | - | - | - |
| ΔD2,3 | 70-80% | 26 | 8 | 10 | 34.6 | 9.3 | 48 |
| Δ4 | >95% | 20 | 25 | 15 | 13 | 22.5 | 8.7 |
| Δ5 | >75-95% | 10.2 | 12.8 | 8.9 | 12.8 | 30.7 | 11.5 |
| A22E,G80E | >95% | 41.2 | 26.2 | 6.25 | 12.5 | 47.5 | 12.5 |
| N9A,N18A | >60-95% | 22.5 | 125 | 41.2 | 52.5 | 91.25 | 101.25 |
| sCD164-Fc | >95% | 19.1 | - | 11.6 | 18.3 | 42.5 | 37.5 |
| Ex1,4,6 | 55-90% | 361 | - | 62.3 | - | - | 93 |
| Ex1,6 | 60% | - | - | - | - | - | 142 |
| Δ6 | >75-95% | 128 | 128 | 20.6 | 32 | 192.3 | 38.4 |

Fig. 13

SOLUBLE CD164 POLYPEPTIDES

CROSS-REFERENCE TO RELATED APPLICATION

This application is the U.S. national stage application of International Patent Application No. PCT/EP2006/050422, filed Jan. 24, 2006, which claims the benefit of U.S. Provisional Patent Application No. 60/655,382, filed Feb. 23, 2005, the disclosures of which are hereby incorporated by reference in their entireties, including all figures, tables and amino acid or nucleic acid sequences.

FIELD OF THE INVENTION

The present invention is in the field of inflammation and autoimmune disorders. In particular, the present invention relates to new sCD164 variants and their use in preventing and/or treating inflammatory and/or autoimmune disorders.

BACKGROUND OF THE INVENTION

The primary function of the human immune system is to protect an individual against infection by foreign invaders such as microorganisms or viruses. However, it may happen that the immune system attacks an individual's own tissues, leading to pathologic states known as autoimmune diseases, which are frequently associated with inflammatory processes.

According to a commonly used classification, CD4+ T-cells can be assigned to two different subsets called T helper type 1-cells (Th1) and T helper type 2-cells (Th2) on the basis of distinct, non-overlapping cytokine expression patterns. Th1 is characterized by the secretion of IL-2, interferon-γ, IL-12 and TNF-α, and Th2 by the secretion of IL-4, IL-5, IL-9, IL-10 and IL-13. In spite of this general categorization, these are not strict subsets as IFN-γ and IL-10 can suppress effects associated with Th1 as well as Th2 responses, and IL-4 and IL-13 are also able to promote the production of IL-12, thereby promoting Th1 and potentially inhibiting Th2 responses. Th1 T-cells are able to mediate macrophage activation and delayed-type hypersensitivity (DTH), giving rise to pro-inflammatory or cell-mediated immune responses, whereas Th2 T-cells promote IgG1 and IgE secretion leading to immediate-type hypersensitivity reactions (humoral immunity; stimulation of antibody-mediated responses, activation of mast cells, and tissue eosinophilia). Th1 is a key feature in the pathogenesis of diseases like rheumatoid arthritis, sarcoidosis, and tuberculosis, whereas Th2 is involved in allergy, antiparasite responses and in the asthmatic airway.

Inflammation is the body's basic response to a variety of external or internal insults, such as infectious agents, physical injury, hypoxia, or disease processes in nearly any organ or tissue in the body. Inflammation entails the four well-known symptoms, namely redness, heat, tenderness/pain, and swelling. More specifically, inflammation involves assembly of immune system cells and molecules at a target site. Examples for chronic inflammatory diseases are rheumatoid arthritis, inflammatory bowel disease, systemic lupus erythematosus, multiple sclerosis, and type 1 diabetes, for example. These diseases are also often characterized as autoimmune diseases or autoimmune/inflammatory disorders.

As mentioned above, an autoimmune disease is a condition in which the body recognizes its own tissues as foreign and directs an immune response against them.

There are many different autoimmune diseases, and they can each affect the body in different ways. For example, the autoimmune reaction is directed against the brain in multiple sclerosis and the gut in Crohn's disease. In other autoimmune diseases such as systemic lupus erythematosus (lupus), affected tissues and organs may vary among individuals with the same disease. One person with lupus may have affected skin and joints whereas another may have affected skin, kidney, and lungs. Ultimately, damage to certain tissues by the immune system may be permanent, as with destruction of insulin-producing cells of the pancreas in Type 1 diabetes mellitus.

Rheumatoid arthritis is a disease marked by signs and symptoms of inflammation of the joints. Systemic lupus erythematosus (SLE) is characterized by red, scaley patches on the skin and by malfunction of the kidneys at the advanced stage of the disease, and is associated with inflammatory reactions triggered by deposition of immune complexes in blood vessels, particularly in the kidneys. Multiple sclerosis is a disease characterized by chronic or by relapsing, inflammatory conditions that can cause weakness, body tremors and, in extreme cases, paralysis, and is associated with immune system attack of the protective myelin sheath surrounding peripheral nerve cells. Allergic inflammation is consistent with a Th2-cell-based aetiology of atopic disease. For example, defective priming of Th2 cells in the absence of IL-4 resulted in a failure to generate allergic inflammatory responses after subsequent airway challenge. IL-5 and IL-13 have been shown to be more directly responsible for the characteristic eosinophil infiltrates and mucus hypersecretion.

In multiple sclerosis, Th1 mediated immune responses are thought to promote the disease, whereas Th2 mediated immune responses are believed to have an ameliorating effect on the progression of the disease. T cells expressing IL-10 have been shown to suppress experimental autoimmune encephalomyelitis (EAE), a rat model for multiple sclerosis. TNF-α, has been hypothesized to be responsible for the induction of EAE (TNF-α, can be secreted by both Th1 and Th2 cultures).

Human systemic lupus erythematosus (SLE) is believed to be driven by a Th2 response. However, IFN-γ has been shown to have a major effect on disease progression in a mouse model, whereas IL-4 is expected to mediate disease maintenance.

Myocarditis is defined by inflammation of the heart muscle and is thought to be mediated by an autoimmune response to a cardiac-specific antigen after an acute upper respiratory infection. The severity of the experimental autoimmune myocarditis (EAM) in the mouse model is reduced by administration of anti-IL-4, indicating a role of IL-4 in disease progression.

Examples of autoimmune diseases are given in Table I.

TABLE I

| Examples of Autoimmune Diseases: |
|---|
| Nervous System: |
| Multiple sclerosis<br>Myasthenia gravis<br>Autoimmune neuropathies, e.g. Guillain-Barré<br>Autoimmune uveitis |

TABLE I-continued

Examples of Autoimmune Diseases:

Blood:

Autoimmune hemolytic anemia
Pernicious anemia
Autoimmune thrombocytopenia

Blood Vessels:

Temporal arteritis
Anti-phospholipid syndrome
Vasculitides such as Wegener's granulomatosis
Behcet's disease Skin:

Psoriasis
Dermatitis herpetiformis
Pemphigus vulgaris
Vitiligo

Gastrointestinal System:

Crohn's Disease
Ulcerative colitis
Primary biliary cirrhosis
Autoimmune hepatitis Endocrine Glands:

Type 1 or immune-mediated diabetes mellitus
Grave's Disease
Hashimoto's thyroiditis
Autoimmune oophoritis and orchitis
Multiple Organs, including the Musculoskeletal System:*

Rheumatoid arthritis
Systemic lupus erythematosus
Multiple Organs Including the Musculoskeletal System:*

Scleroderma
Polymyositis, dermatomyositis
Spondyloarthropathies such as ankylosing spondylitis
Sjogren's syndrome

*These diseases are also called connective tissue (muscle, skeleton, tendons, fascia, etc.) diseases.

CD164 is a member of the mucin-like receptor or sialomucin superfamily of glycoproteins. Sialomucins are transmembrane glycoproteins ranging from 50-3000 kD exhibiting limited similarity at the cDNA and amino acid levels. Mucin-like expressed proteins share the common characteristic of bearing numerous O-glycosylations linked to serine and threonine residues, which infer multiple kinds of cell-cell or cell-extracellular matrix interactions. Functions of mucin receptors depend on cell types and states of activation correlated with the core mucin peptide and with the cell-specific expression of glycosyl transferases, which in turn regulate the structure and presentation of the O-linked oligosaccharide side chains, membrane anchorage, signal transduction abilities and or/the trafficking of the mucin to the correct cellular domain.

Human CD164 is an ortholog of murine MGC-24v (*M. musculus*) and rat endolyn (*R. norvegicus*), a membrane protein located in the lysosomal and endosomal compartment of mammalian cells. Isoforms, domains and the subcellular distribution of CD164/endolyn, have been described (Chan et al., 2001).

In its native state, human CD164 is a disulphide-linked homodimer of two 80-85 kDa subunits. CD164 is highly glycosylated, containing both O- and N-linked glycans. The extracellular region is comprised of two mucin domains (I and II) linked by a non-mucin domain containing intra-disulphide bridges as well as a cysteine-rich motif that resembles a consensus pattern previously found in growth factor and cytokine receptors. CD164 also contains a transmembrane domain and a 13-amino acid intracellular region that includes a C-terminal motif (i.e. YHTL) able to target the protein to endosomes and lysosomes.

Four human CD164 mRNA species have been described arising by alternative splicing of six bona fide exons from a single genomic transcription unit located on human chromosome 6q21 (Zannettino A, 2001; Watt and Chan, 2000).

The predominant CD164 (E1-6) isoform represents a 178 amino acid type I transmembrane glycoprotein. The other described isoforms are a sialomucin CD164 or CD164 isoform delta 5 containing 178 amino acids; a 184 residues CD164 isoform delta 4; and a 200 kD principally soluble isoform termed MGC-24 (for Multi-Glycosylated Core protein of 24 kD) lacking the transmembrane anchoring motif and having 189 residues. All isoforms are highly glycosylated proteins with O- and N-linked glycosylation sites.

CD164 functions include mediating, or regulating, haematopoietic progenitor cell adhesion and the negative regulation of their growth and/or differentiation. CD164 is usually expressed by CD34+ and CD34lo/− haematopoietic stem cells and associated microenvironmental cells (Watt et al., 1998). CD164 is also expressed by committed myeloid and erythroid colony forming cells, on bone marrow stromal and endothelial cells, weakly on lymphocytes, and on mesenchymal stem cells. CD164 may play a key role in haematopoiesis by facilitating the adhesion of human CD34+ cells to bone marrow stroma and by suppressing CD34+CD38lo/− haematopoietic progenitor cell proliferation, acting as a potent signaling molecule (Zannettino et al., 1998).

These effects involve the CD164 class I and/or II epitopes recognized by the monoclonal antibodies (mAbs) 105A5 and 103B2/9E10. The epitopes are carbohydrate-dependent and are located on the N-terminal mucin domain I (Watt et al., 2000; Doyonnas et al., J Immunol, 165: 840-851, 2000). The interaction of haemotopoietic cells with stromal/endothelial cells in their immediate microenvironment is thought to be of major importance in the regulation of haematopoietic stem self-renewal, quiescence, commitment and migration. These interactions involve cooperation between adhesion receptors, their cognate ligands and cytokines. A range of cell adhesion molecules (CAMS) including the Ig, integrin, cadherin, selectin and mucin-like protein families, participate in these processes.

CD164 also has a role in myogenic differentiation (Lee et al., 2001). Overexpression of CD164 in myoblast cell lines accelerated expression of biochemical markers of differentiation and enhanced formation of multinucleate myotubes, whereas antisense CD164 or soluble extracellular regions of CD164 inhibited myogenesis.

The peanut agglutinin (PNA)-binding site of soluble MGC-24 represents a tumor associated carbohydrate marker expressed in many carcinomas. Total MGC-24 mRNA was found to be lower in human colorectal carcinomas as compared with normal adjacent mucosal tissues (Matsui et al., 2000). Lymphatic vessel invasion by the carcinoma was correlated to low levels of MGC-24 mRNA in colon carcinomas, whereas high levels did correlate with less venous invasion and less remote metastasis. Monoclonal antibodies specific for CD164 are said to be useful for cancer diagnosis or therapy and haematopoiesis inhibition (EP889054, EP761814).

WO 02/098917 discloses the protein NOV25 (SEQ ID NO: 8; FIG. 1B) comprising a sequence 80% homologous with the mature form of the extracellular domain of human CD164.

EP1033401 discloses a protein (SEQ ID NO: 7582) comprising a sequence identical to the mature form of the extracellular domain of human CD164 (SEQ ID NO: 7; FIG. 1B).

The biological activities and therapeutic utilities of the CD164-like proteins disclosed is these prior art documents have not been analyzed.

SUMMARY OF THE INVENTION

The present invention is based on the production of new sCD164 variants and the finding that such sCD164 variants have an inhibitory effect on the expression of cytokines such as interferon-γ, IL-2, IL-4, IL-5, IL-10 and TNF-α in cells that produce these cytokines when stimulated with agents such as concavalin A.

Therefore, the invention relates to sCD164 variants and their use for treatment and/or prevention of inflammatory and/or autoimmune disorders, the sCD164 variant being chosen from:
  a. A polypeptide having a sequence selected from SEQ ID NO: 1, 2, 3, 4, 5, 6, 7, 8, 9, 10, 11, 12, 13, 14, 16 or 18;
  b. A polypeptide of (a) further comprising a signal sequence, preferably amino acids 1 to 23 of SEQ ID NO: 17;
  c. A mutein of a polypeptide of (a) or (b), wherein the amino acid sequence has at least 90% or 91% or 92% or 93% or 94% or 95% identity to at least one of the sequences of (a) or (b);
  d. A mutein of a polypeptide of (a) or (b) which is encoded by a DNA hybridizing to the complement of the DNA sequence encoding a polypeptide of (a) or (b) under highly stringent conditions;
  e. A mutein of a polypeptide of (a) or (b) wherein any changes in the amino acid sequence are conservative amino acid substitutions;
  f. an isoform, fused protein, functional derivative, or active fraction of a polypeptide of (a) to (e).

Antibodies directed to these variants, compositions comprising these sCD164 variants, polynucleotides encoding them, host cells producing such sCD164 variants, and a process of production of such sCD164 variants are further aspects of the present invention.

BRIEF DESCRIPTION OF THE DRAWINGS

FIG. 2 shows a table summarizing a number of parameters characterizing sCD164 variants of the invention.

FIG. 13 shows the $E_{max}$ and EC50 values calculated on the basis of the experiments shown in FIGS. 3 to 12.

(FIG. 17C) Shows the percent AUC inhibition of all treatments. Data are referring to a single experiment given as mean ±SEM of n=8 mice /group.

(FIG. 18A) Body weight change (% D0)
(FIG. 18B) Clinical Score (0-4)
(FIG. 18C) Colon Length (cm)
(FIG. 18D) Colon weight/length (mg/100g bw/cm)
(FIG. 18E) Serum amyloid protein (μg/ml)
(FIG. 18F) Spleen weight (mg/100g bw).

(FIG. 19A) Body weight change (% D0)
(FIG. 19B) Clinical Score (0-4)
(FIG. 19C) Colon weight/length (mg/100g bw/cm)
(FIG. 19D) Colon Length (cm)
(FIG. 19E) Serum amyloid protein (μg/m1)
(FIG. 19F) Spleen weight (mg/100g bw),
(FIG. 20A) Body weight change (% D0)
(Fig. 20B) Clinical Score (0-4)
(FIG. 20C) Colon weight/length (mg/100g bw/cm)
(FIG. 20D) Colon Length (cm)
(FIG. 20E) Serum amyloid protein (μg/ml)
(FIG. 20F) Spleen weight (mg/100g bw)
(FIG. 20G) Il-1β (pg/mg/prot).

(FIG. 21A) Clinical Score (0-4)
(FIG. 21B) Clinical Score (AUC D0-14)
(FIG. 21C) Total Swelling (mm vs d0)
(FIG. 21D) Total Swelling (AUC D0-14)
(FIG. 21E) Osteocalein (ng/ml).

(FIG. 21A) Clinical Score (0-4)
(FIG. 22B) Clinical Score (AUC D0-14)
(FIG. 22C) Total Swelling (mm vs d0)
(FIG. 22D) Total Swelling (AUC D0-14)
(FIG. 22E) Osteocalcin (ng/ml).

DETAILED DESCRIPTION OF THE INVENTION

Figure 1:
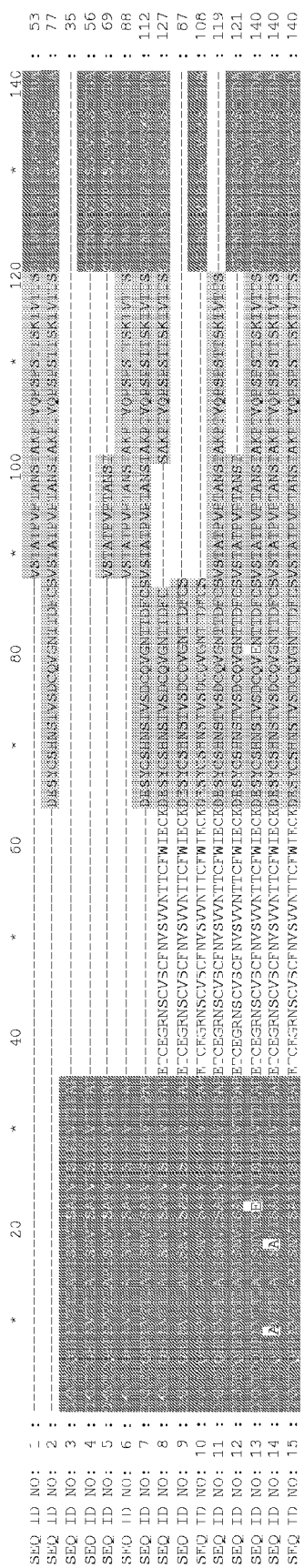
FIG. 1 shows an alignment and length (in amino acids) of sCD164 variants having the sequences SEQ ID NOs: 1 to 15 of the annexed sequence listing.
Figure 3:
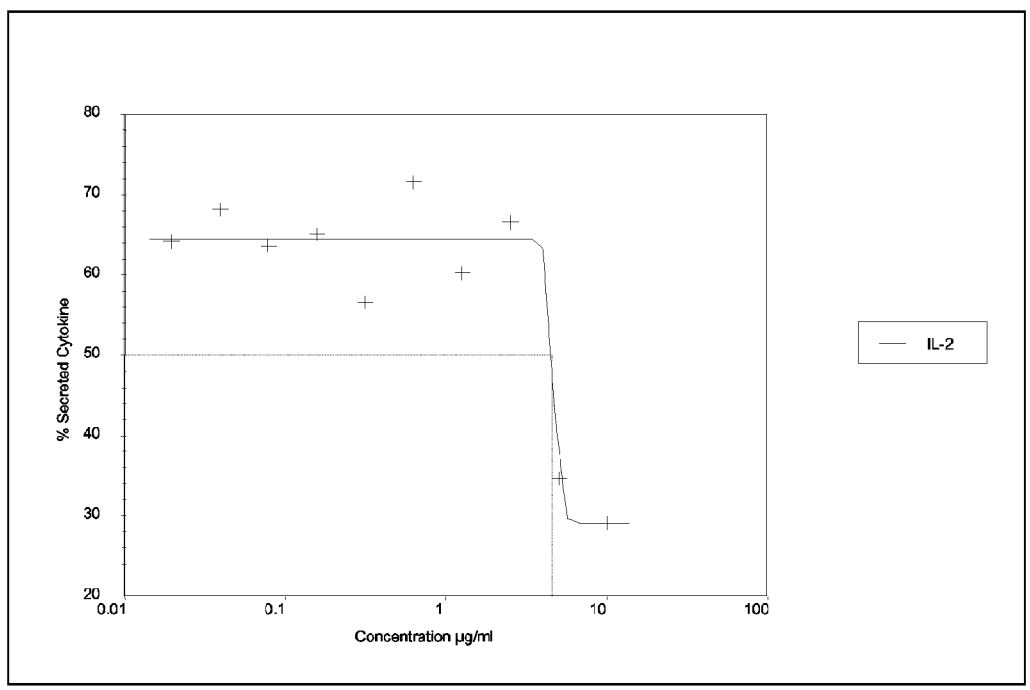
FIG. 3 shows the effect of sCD164 variant Ex1, 2, 3 (SEQ ID NO: 2) on IL-2 release of ConA-stimulated, human PBMC cells. The X-axis represents the sCD164 variant concentration in μg/ml. The Y-axis represents the concentration of IL-2 released in % of the maximal release in control cells (i.e., cells not treated with a sCD164 variant).
Figure 4:
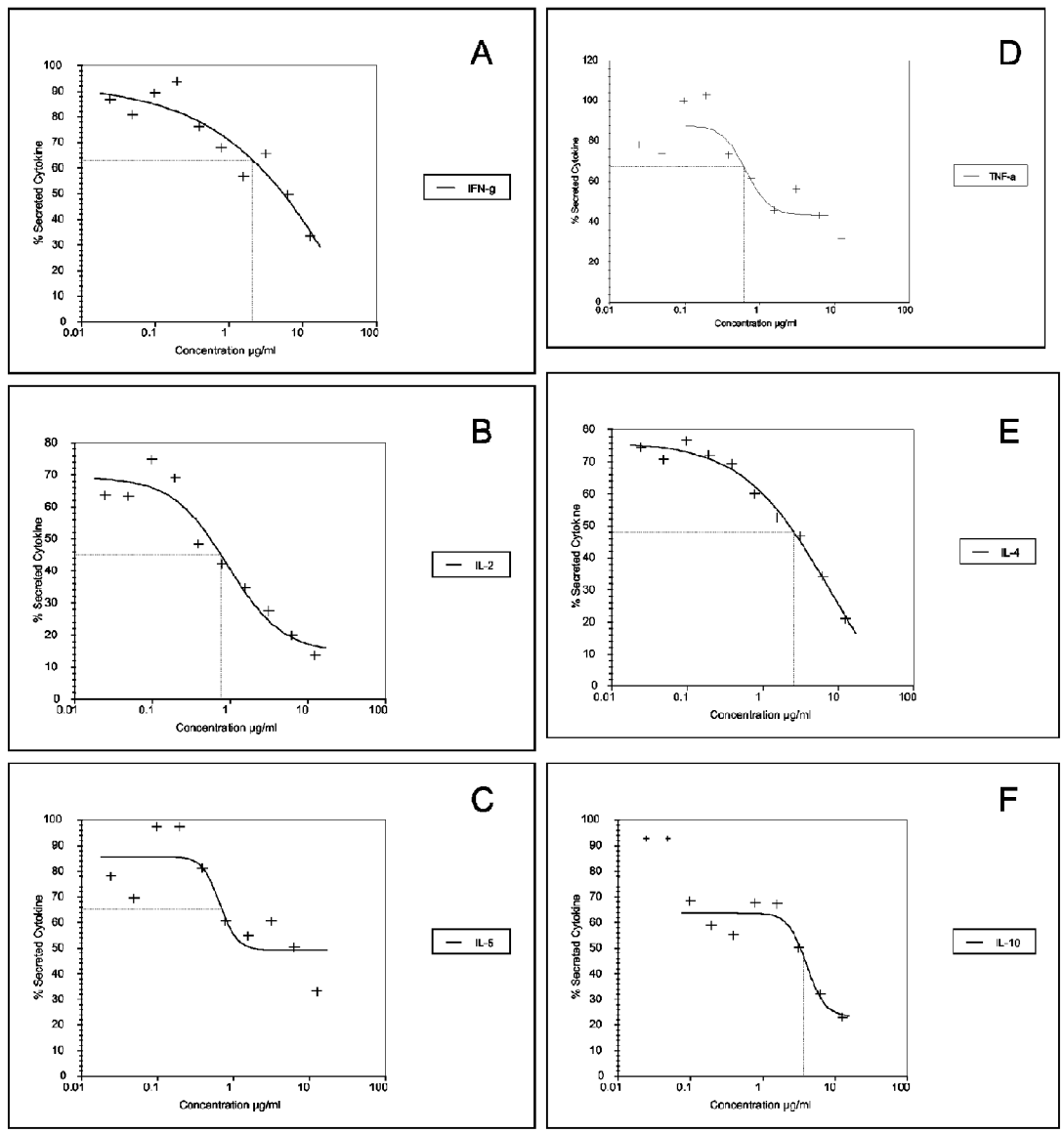
FIGS. 4A-4F show the effect of sCD164 variant Δ2,3 (SEQ ID NO: 6) on IFN-γ (FIG. 4A), IL-2 (FIG. 4B), IL-5 (FIG. 4C), TNF-α(FIG. 4D), IL-4 (FIG. 4E) or IL-10 (FIG. 4F) release of ConA-stimulated, human PBMC cells. The X-axis represents the sCD164 variant concentration in μg/ml. The Y-axis represents the concentration of cytokine released in %.
Figure 5:
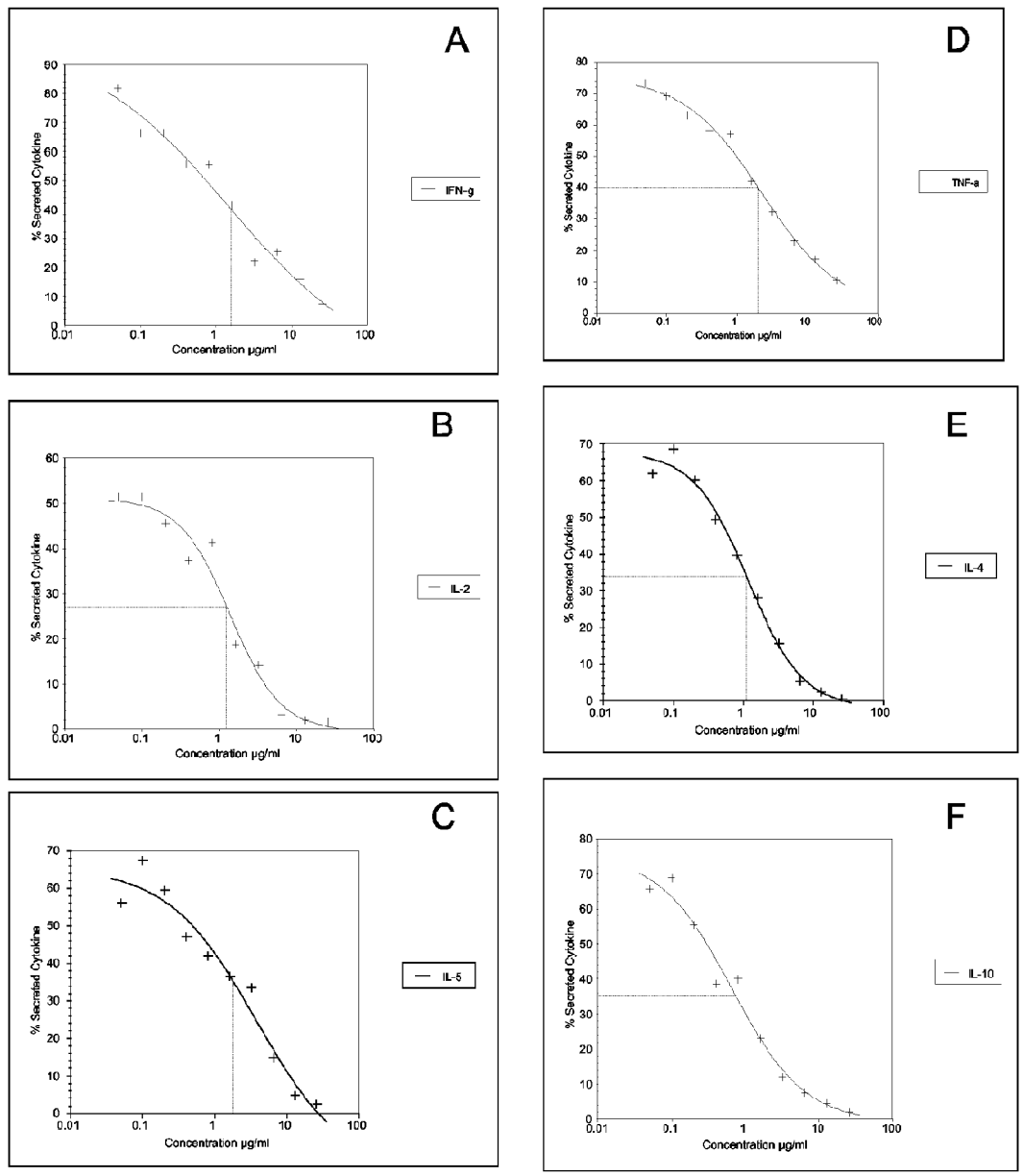
FIGS. 5A-5F show the effect of sCD164 variant Δ4 (SEQ ID NO: 8) on IFN-γ (FIG. 5A), IL-2(FIG. 5B), IL-5 (FIG. 5C), TNF-α, (FIG. 5D), IL-4 (FIG. 5E) or IL-10 (FIG. 5F) release of ConA-stimulated, human PBMC cells. The X-axis represents the sCD164 variant concentration in μ/ml. The Y-axis represents the concentration of cytokine released in %.
Figure 6:
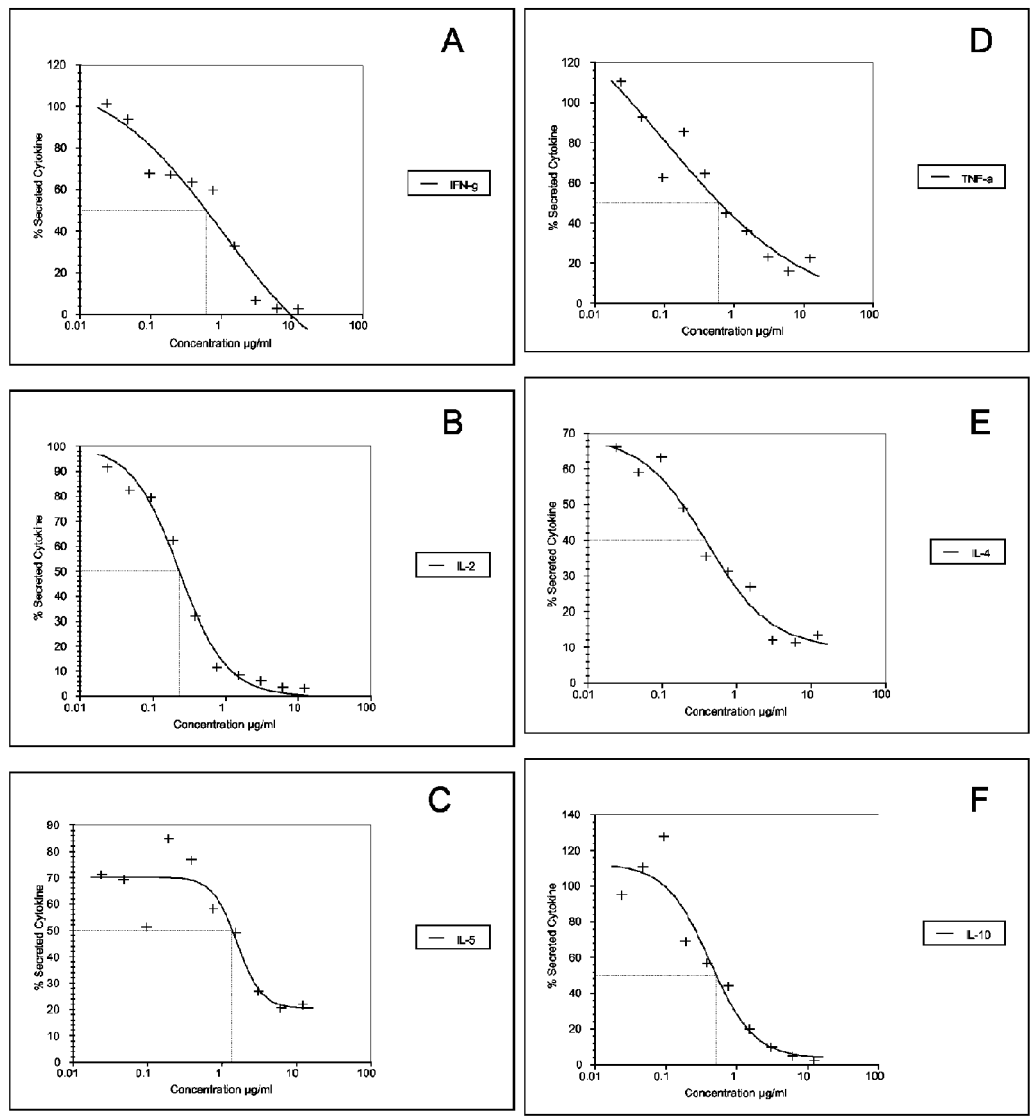
FIGS. 6A-6F show the effect of sCD164 variant Δ5 (SEQ ID NO: 12) on IFN-γ (FIG. 6A), IL-2 (FIG. 6B), IL-5 (FIG. 6C), TNF-α(FIG. 6D), IL-4 (FIG. 6E) or IL-10 (FIG. 6F) release of ConA-stimulated, human PBMC cells. The X-axis represents the sCD164 variant concentration in μg/ml. The Y-axis represents the concentration of cytokine released in %.
Figure 7:
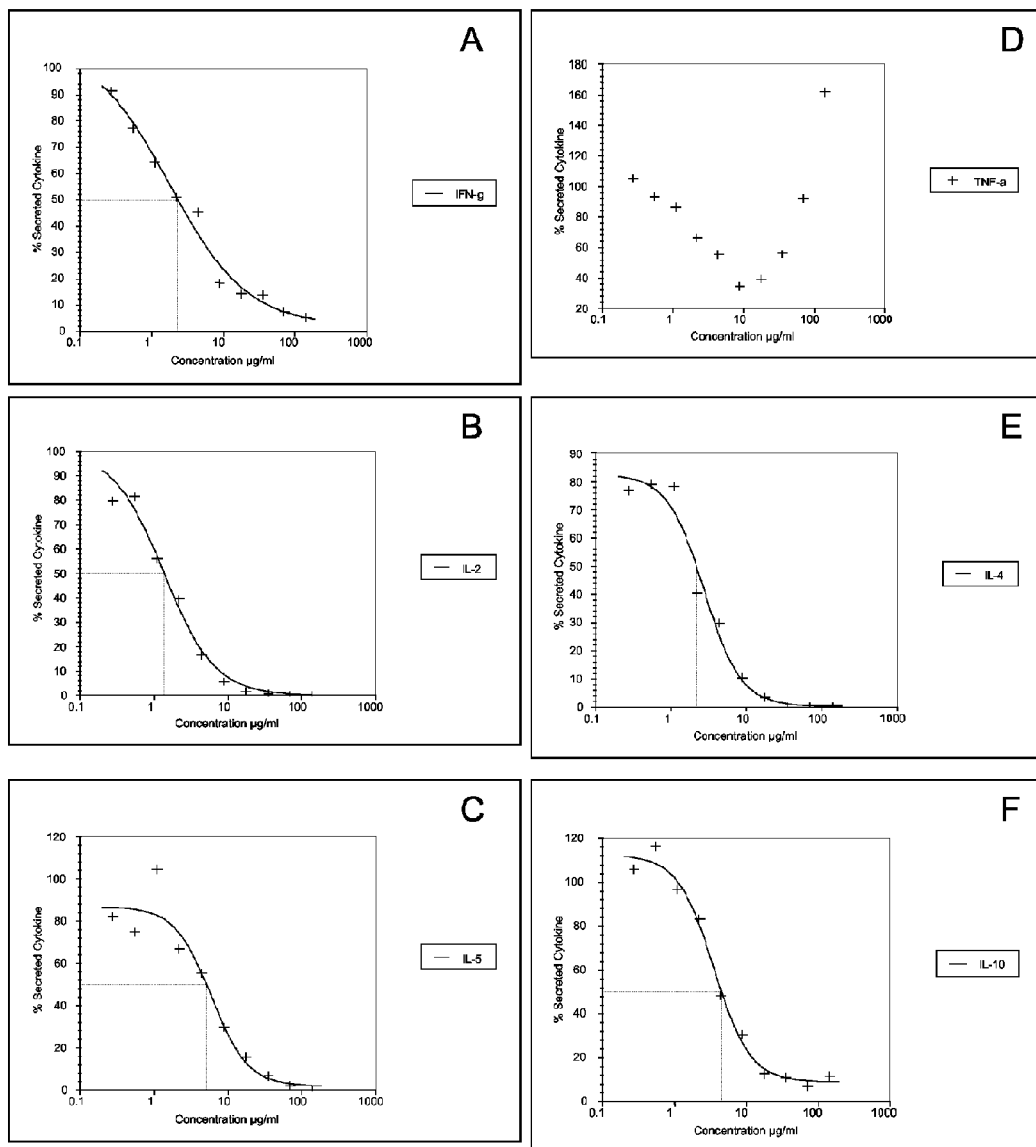
FIGS. 7A-7F show the effect of soluble sCD164-Fe variant (SEQ ID NO: 16) on IFN-γ(FIG. 7A), IL-2 (FIG. 7B), IL-5 (FIG. 7C), TNF-α(FIG. 7D), IL-4 (FIG. 7E) or IL-10 (FIG. 7F) release of ConA-stimulated, human PBMC cells. The X-axis represents the sCD164 variant concentration in μg/ml. The Y-axis represents the concentration of cytokine released by secretion in μg/ml.
Figure 8:
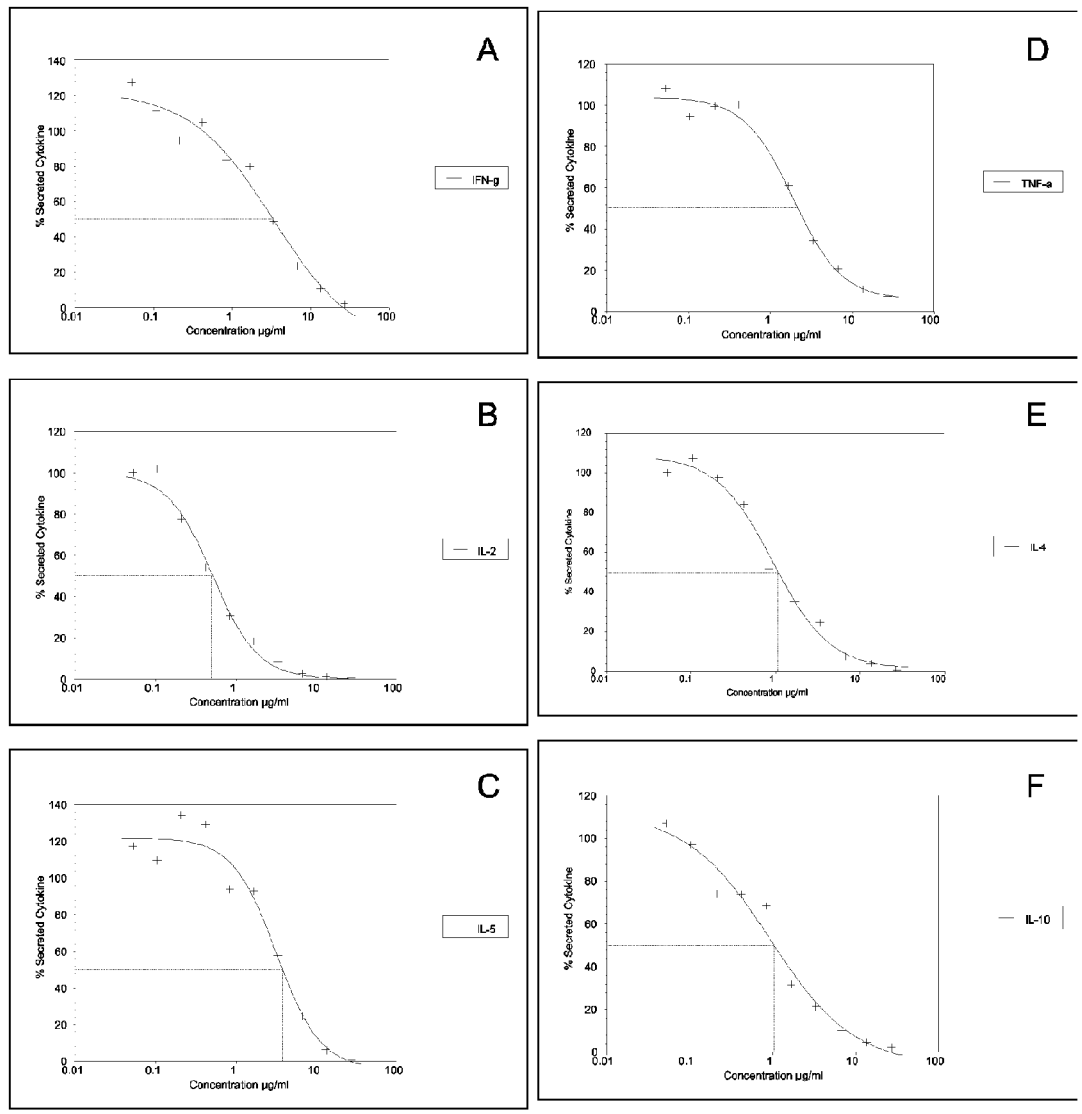
FIGS. 8A-8F show the effect of sCD164 variant A22E, G80E (SEQ ID NO: 13) on IFN-γ (FIG. 8A), IL-2 (FIG. 8B), IL-5 (FIG. 8C), TNF-α (FIG. 8D), IL-4 (FIG. 8E) or IL-10 (FIG. 8F) release of ConA-stimulated, human PBMC cells. The X-axis represents the sCD164 variant concentration in μg/ml. The Y-axis represents the concentration of cytokine released in %.
Figure 9:
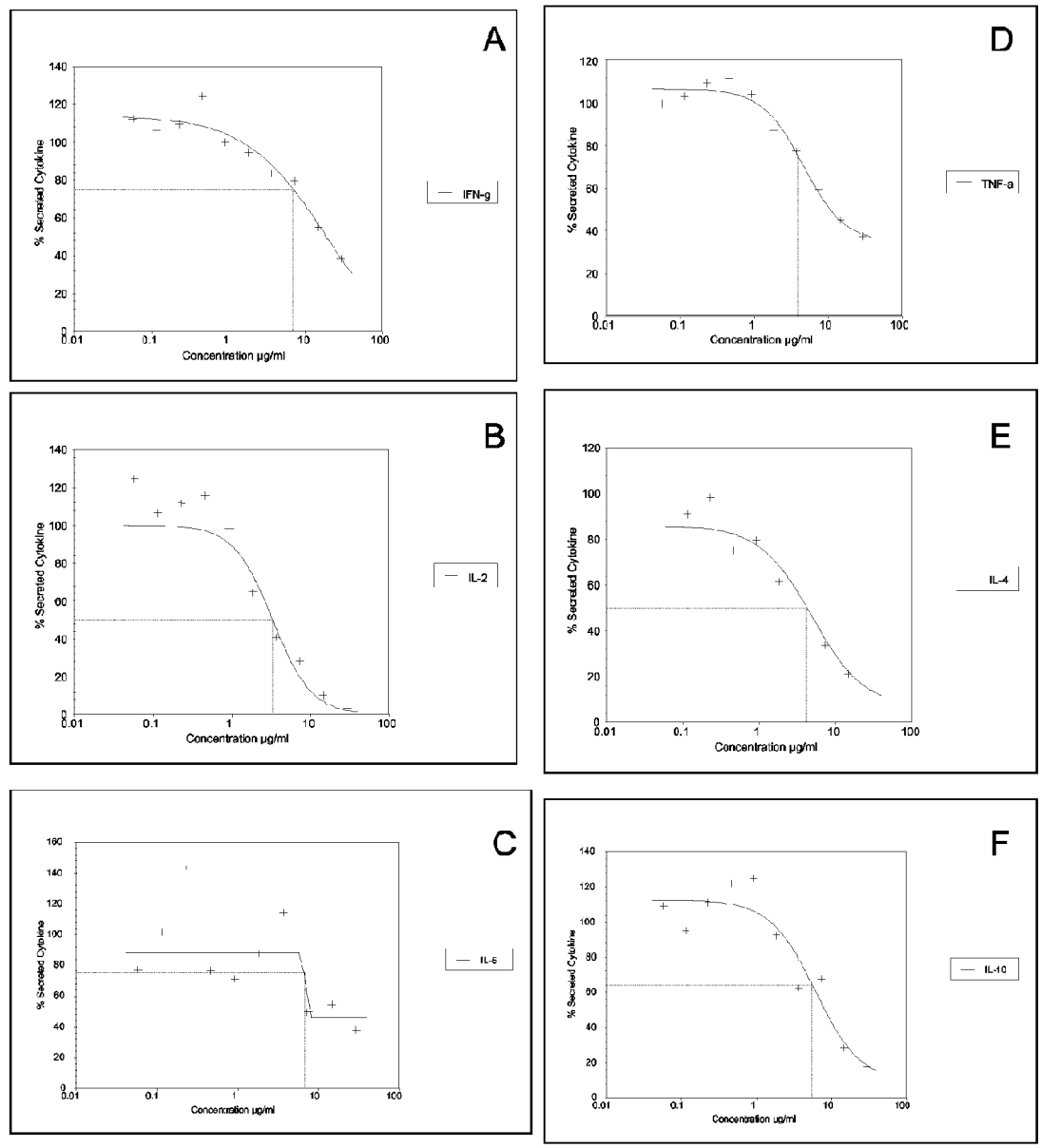
FIGS. 9A-9F show the effect of sCD164 variant N9A, N18A (SEQ ID NO: 14) on IFN-γ (FIG. 9A), IL-2 (FIG. 9B), IL-5 (FIG. 9C), TNF-α (FIG. 9D), IL-4 (FIG. 9E) or IL-10 (FIG. 9F) release of ConA-stimulated, human PBMC cells. The X-axis represents the sCD164 variant concentration in μg/ml. The Y-axis represents the concentration of cytokine released in %.
Figure 10:
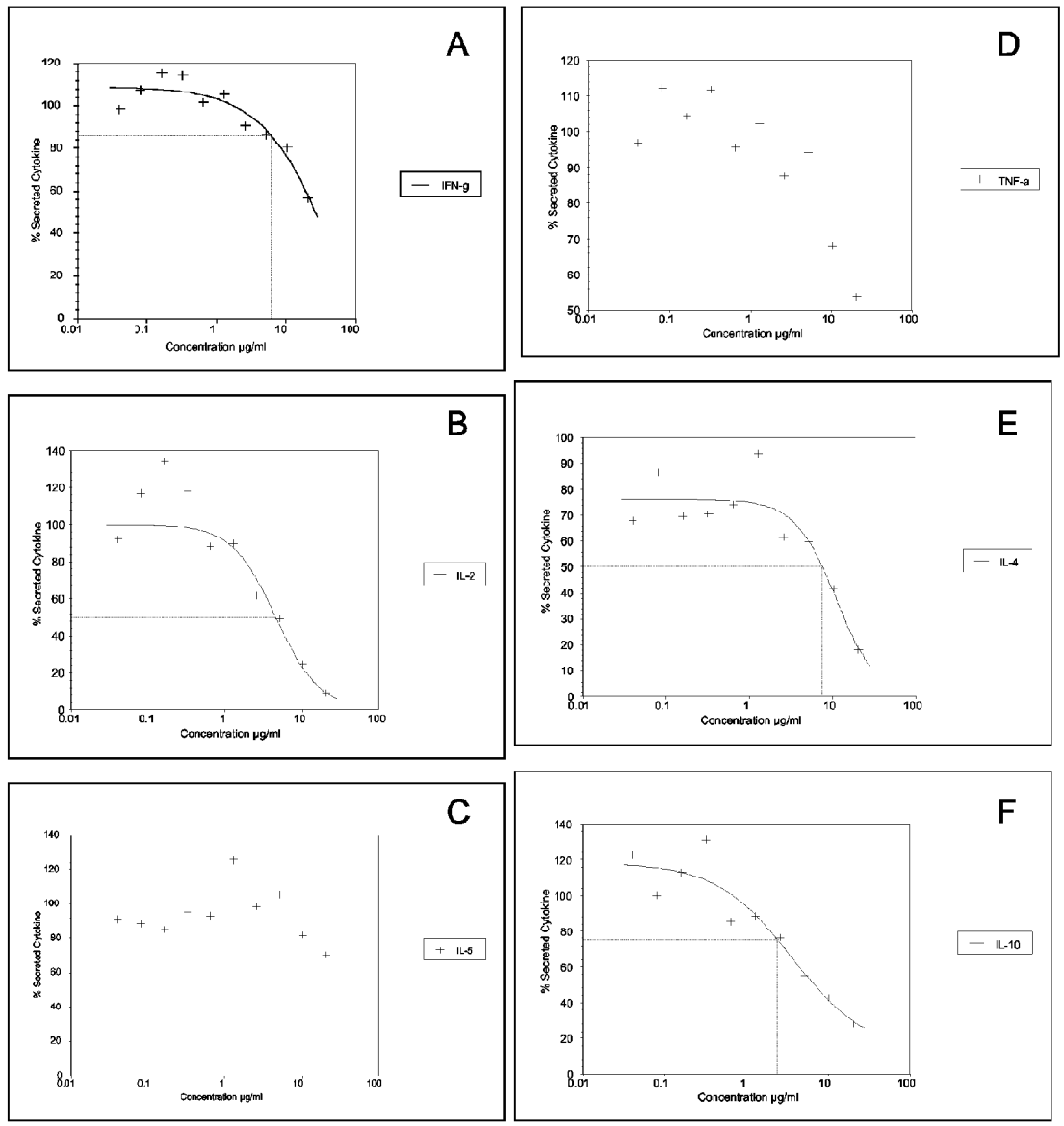
FIGS. 10A-10F show the effect of sCD164 variant Ex1,4,6 (SEQ ID NO: 5) on IFN-γ (FIG. 10A), IL-2 (FIG. 10B), IL-5 (FIG. 10C), TNF-α (FIG. 10D), IL-4 (FIG. 10E) or IL-10 (FIG. 10F) release of ConA-stimulated, human PBMC cells. The X-axis represents the sCD164 variant concentration in μg/ml. The Y-axis represents the concentration of cytokine released in %.
Figure 11:
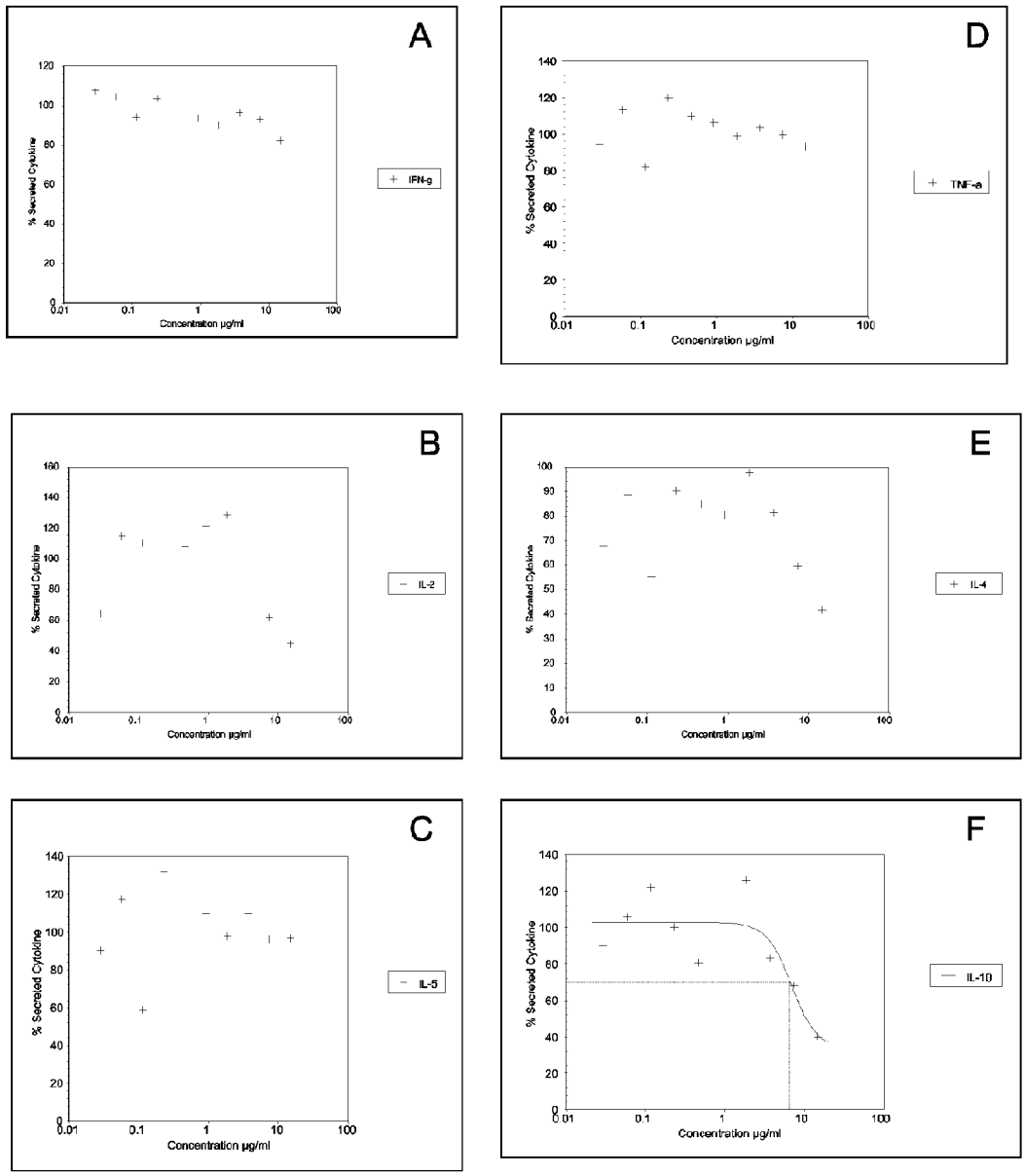
FIGS. 11A-11F show the effect of sCD164 variant Ex1,6 (SEQ ID NO: 4) on IFN-γ (FIG. 11A), IL-2 (FIG. 11B), IL-5 (FIG. 11C), TNF-α (FIG. 11D), IL-4 (FIG. 11E) or IL-10 (FIG. 11F) release of ConA-stimulated, human PBMC cells. The X-axis represents the sCD164 variant concentration in μg/ml. The Y-axis represents the concentration of cytokine released in %.
Figure 12:
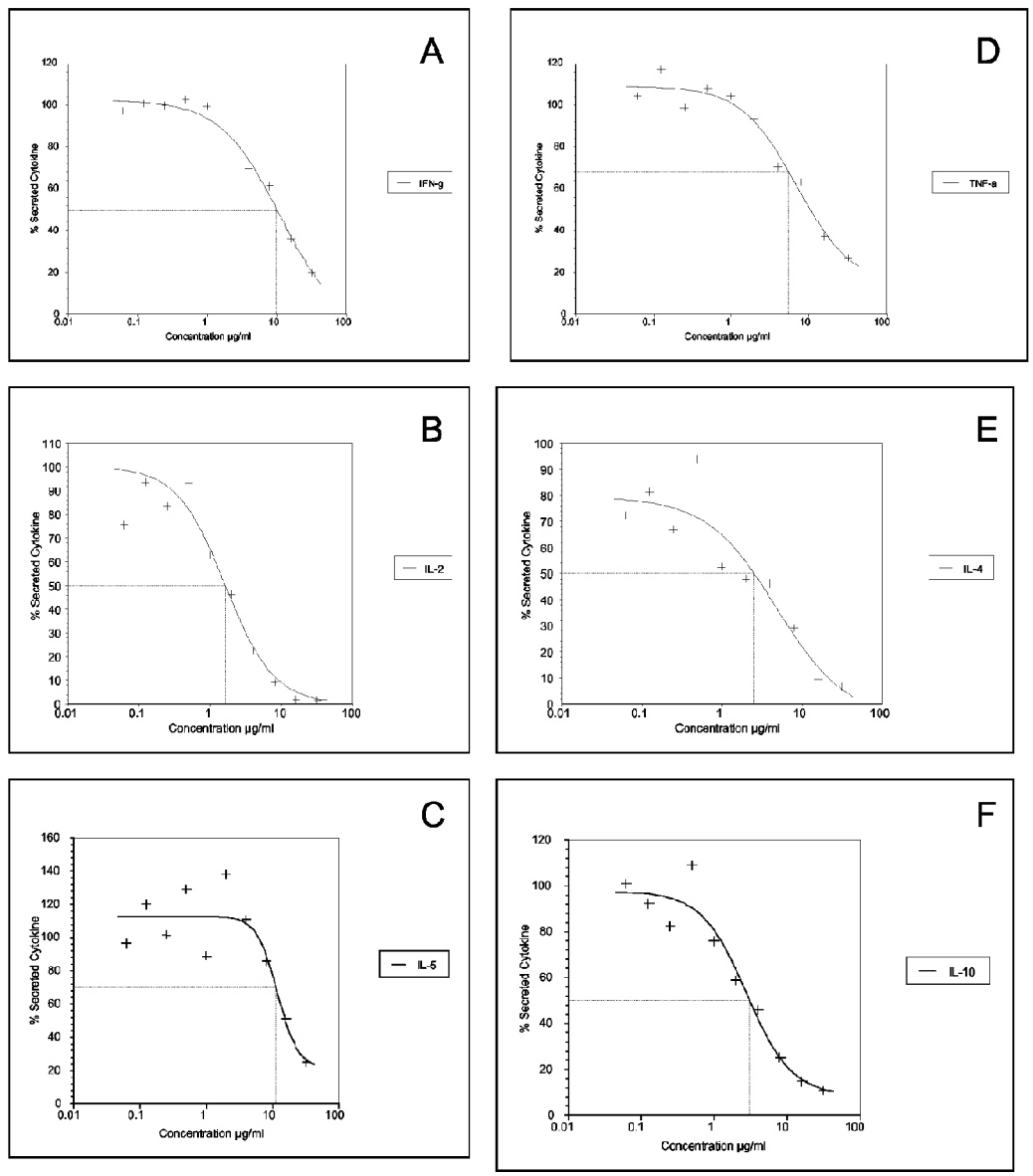
FIGS. 12A-12F show the effect of sCD164 variant Δ6 (SEQ ID NO: 11) on IFN-γ (FIG. 12A), IL-2 (FIG. 12B), IL-5 (FIG. 12C), TNF-α (FIG. 12D). IL-4 (FIG. 12E) or IL-10 (FIG. 12F) release of ConA-stimulated, human PBMC cells. The X-axis represents the sCD164 variant concentration in μg/ml. The Y-axis represents the concentration of cytokine released in %.

In accordance with the present invention, it has been found that sCD164 variants, comprising the whole or parts of the extracellular domain of human CD164, have an inhibitory effect on the cellular expression and secretion of certain cytokines, e.g. interferon-γ, IL-2, IL-4, IL-5, IL-10 and TNF-α, following stimulation of peripheral blood mononuclear cells (PBMCs) with agents such as concanavalin A (ConA) or anti-CD3 and anti-CD28 antibodies. As cytokine release is an event occurring in inflammatory/autoimmune diseases, these sCD164 variants are proposed as therapeutic proteins for prevention or treatment of inflammatory and/or autoimmune diseases.

The administration of sCD164 variants was shown to have a beneficial effect in in vivo animal models of inflammatory/autoimmune diseases. sCD164 variants were shown to significantly decrease cell infiltration in generic models of inflammation i.e. thioglycollate-induced peritoneal recruitment of monocytes/macrophages and LPS induced TNF alpha release model.

A positive effect of the sCD164 variants of the invention was found in a model of Concanavalin-A induced Hepatitis and in a model of skin inflammation in mice.

In addition to this, it has been shown, in a model for ulcerative colitis and arthritis in Mice, that sCD164 variants significantly improved various physiological parameters relating to the diseases.

Further confirmation of the therapeutic use of proteins may be obtained in animal models for individual inflammatory/autoimmune diseases.

It is therefore the first aspect of the present invention to use a sCD164 variant for the manufacture of a medicament for treatment and/or prevention of inflammatory and/or autoimmune disorders, the sCD164 variant being chosen from:
  a. A polypeptide having a sequence selected from SEQ ID NO: 1, 2, 3, 4, 5, 6, 7, 8, 9, 10, 11, 12, 13, 14, 16 or 18;
  b. A polypeptide of (a) further comprising a signal sequence, preferably amino acids 1 to 23 of SEQ ID NO: 17;
  c. A mutein of a polypeptide of (a) or (b), wherein the amino acid sequence has at least 90% or 91% or 92% or 93% or 94% or 95% identity to at least one of the sequences of (a) or (b);
  d. A mutein of a polypeptide of (a) or (b) which is encoded by a DNA sequence hybridizing to the complement of the DNA sequence encoding a polypeptide of (a) or (b) under highly stringent conditions;
  e. A mutein of a polypeptide of (a) or (b) wherein any changes in the amino acid sequence are conservative amino acid substitutions;
  f. an isoform, fused protein, functional derivative, or active fraction of a polypeptide of (a) to (e).

Further aspects of the present invention relate to the use of sCD164 variant as defined in (a) to (f) for the manufacture of a medicament for treatment and/or prevention of skin inflammation related disorders, hepatitis, ulcerative colitis or arthritis.

In the frame of the present invention, the polypeptides or proteins defined in (a) to (f) are called "sCD164 variants" or "sCD164 variants of the invention". For convenience, the individual sCD164 variants recited in (a) have been given designations reflecting their structural composition. FIG. 2 indicates the corresponding names of these sCD164 variants. The polypeptide composed of exons 1 to 6 corresponds to the mature full-length CD164 extracellular domain, and is herein also called soluble CD164, or sCD164. The sCD164 variant of SEQ ID NO: 16 is an Fc-fusion protein comprising sCD164 fused to an Fc part of an immunoglobulin. The sCD164 variant of SEQ ID NO: 18, sCD164-Fcm, is an Fc-fusion protein comprising sCD164 fused to an Fc part of an immunoglobulin mutated in the Fc receptor and C1q binding regions (LLGG into AEGA at amino acid positions 182-185 and mutated AP into SS at amino acid positions 278-279). SEQ ID NO: 17 is not a sCD164 variant of the invention, it is the full-length human CD164 precursor including the signal peptide (amino acids 1 to 23 of SEQ ID NO: 17).

The term "prevention" within the context of this invention refers not only to a complete prevention of a certain effect, but also to any partial or substantial prevention, attenuation, reduction, decrease or diminishing of the effect before or at early onset of disease.

The term "treatment" within the context of this invention refers to any beneficial effect on progression of disease, including attenuation, reduction, decrease or diminishing of the pathological development after onset of disease.

In the context of the present invention, CD164 is supposed to be understood as a transmembrane receptor. The term "sCD164" or "soluble CD164" is to mean a soluble portion of CD164 in particular any portion of the extracellular domain of CD164.

The term "sCD164 variant" is to be understood as a general term referring to splice variants or isoforms, either naturally occurring or artificially generated, of sCD164, in particular those listed in the table of FIG. 2, including fusion proteins of sCD164. Muteins are further variations in the sequence of sCD164 and/or sCD164 variants.

As used herein the term "muteins" refers to analogs of sCD164 variants, in which one or more of the amino acid residues of a sCD164 variant of the invention are replaced by different amino acid residues, or are deleted, or one or more amino acid residues are added to the natural sequence of sCD164 variant, without having a considerable negative impact on the activity of the resulting product as compared to the initial sCD164 variant. These muteins may e.g. be prepared by known synthesis and/or by site-directed mutagenesis techniques, or any other known technique suitable therefore.

Muteins of a sCD164 variant, which can be used in accordance with the present invention, or a nucleic acid encoding a mutein, include a finite set of substantially corresponding sequences as substitution peptides or polynucleotides which can be routinely obtained by one of ordinary skill in the art, without undue experimentation, based on the teachings and guidance presented herein.

Muteins of the sCD164 variants of the invention include polypeptides having the sequences of SEQ ID NO: 1, 2, 3, 4, 5, 6, 7, 8, 9, 10, 11, 12, 13, 14, 16 or 18, optionally further comprising a signal sequence such as e.g. the signal sequence of human CD164, corresponding to amino acids 1 to 23 of SEQ ID NO: 17, wherein the amino acid sequence has at least 90% or 91% or 92% or 93% or 94% or 95% identity to at least one of the sequences.

Known computer programs may be used to determine whether any particular polypeptide is a percentage identical (or homologous) to a sCD164 variant. Such algorithms and programs include, e.g. TBLASTN, BLASTP, FASTA, TFASTA, and CLUSTALW (Pearson and Lipman, 1988; Altschul et al., 1990; Thompson et al., 1994; Higgins et al., 1996; Altschul et al., 1997; Altschul et al., 1993). Protein and nucleic acid sequence homologies are preferably evaluated using the Basic Local Alignment Search Tool ("BLAST"), which is well known in the art (See, e.g., Karlin and Altschul (1990); Altschul et al., 1990, 1993, 1997).

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. The scoring matrix used may be the BLOSUM62 matrix (see, Gonnet et al., 1992, Henikoff and Henikoff, 1993. The PAM or PAM250 matrices may also be used (See, e.g., Schwartz and Dayhoff, eds, (1978) Matrices for Detecting Distance Relationships: Atlas of Protein Sequence and Structure, Washington: National Biomedical Research Foundation). The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (See, e.g., Karlin and Altschul, (1990)). The BLAST programs may be used with the default parameters or with modified parameters provided by the user.

A preferred method for determining the best overall match between a query sequence (a sequence of the present invention) and a subject sequence, also referred to as a global sequence alignment, can be determined using the FASTDB computer program based on the algorithm of Brutlag et al. 1990. In a sequence alignment the query and subject sequences are both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group=25 Length=0, Cutoff Score=1, Window Size=sequence length, Gap Penalty=5, Gap Size Penalty=0.05, Window Size=247 or the length of the subject amino acid sequence, whichever is shorter.

If the subject sequence is shorter than the query sequence due to N- or C-terminal deletions, not because of internal deletions, the results, in percent identity, must be manually corrected because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, that are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query amino acid residues outside the farthest N- and C-terminal residues of the subject sequence.

For example, a 90 amino acid residue subject sequence is aligned with a 100-residue query sequence to determine percent identity. The deletion occurs at the N-terminus of the subject sequence and therefore, the FASTDB alignment does not match/align with the first residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%.

Preferred changes for muteins in accordance with the present invention are what are known as "conservative" substitutions. Conservative amino acid substitutions of the sCD164 variants may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g. under thirty, and preferably under ten, and do not remove or displace amino acids which are critical to a functional conformation, e.g. cysteine residues. Proteins and muteins produced by such deletions and/or insertions come within the purview of the present invention.

Preferably, the synonymous amino acid groups are those defined in Table I. More preferably, the synonymous amino acid groups are those defined in Table II; and most preferably the synonymous amino acid groups are those defined in Table III.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |

TABLE II-continued

More Preferred Groups of Synonymous Amino Acids

| Amino Acid | Synonymous Group |
|---|---|
| Met | Met, Phe, Ile, Val, Leu |
| Trp | Trp |

TABLE III

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of sCD164 variants, polypeptides or proteins, for use in the present invention include any known method steps, such as presented in U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

The term "fused protein" refers to a polypeptide comprising a sCD164 variant, or a mutein or fragment thereof, fused with another protein, which e.g. has an extended residence time in body fluids. A sCD164 variant may thus be fused to another protein, polypeptide or the like, e.g. an immunoglobulin or a fragment thereof.

"Functional derivatives" as used herein, cover derivatives of a sCD164 variant, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to or better than the activity of the unmodified sCD164 variant, and do not confer toxic properties on compositions containing it.

In a preferred embodiment, the functional derivative comprises at least one moiety attached to one or more functional groups, which occur as one or more side chains on the amino acid residue. The moiety may, preferably include polyethylene glycol side-chains, which may mask antigenic sites and extend the residence of a sCD164 variant in body fluids.

Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g alkanoyl or carbocyclic aroyl groups) or O-acyl derivatives of free hydroxyl groups (for example that of seryl or threonyl residues) formed with acyl moieties.

As "active fractions" of a sCD164 variant, the present invention covers any fragment or precursor of the polypeptide chain of the protein molecule alone or together with associated molecules or residues linked thereto, e.g. sugar or phosphate residues, or aggregates of the protein molecule or the sugar residues by themselves, provided said fragment does not have a substantially impaired activity as compared to the initial sCD164 variant.

The term "salts" herein refers to both salts of carboxyl groups and to acid addition salts of amino groups of a sCD164 variant. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of sCD164 variant relevant to the present invention.

The biological activity of any sCD164 variant, mutein, isoform, fused protein, functional derivative, or active fraction thereof may be tested e.g. in a cell based assay as the one described in Example 2 below. A sCD164 variant may e.g. be considered to be active if it inhibits the release of at least one cytokine (chosen from TNF-α, IFN-γ, IL-2, IL-4, IL-5, or IL-10, for example) in Concanavalin A stimulated peripheral blood monocytic cells. The initial (unmodified) sCD164 variant, or sCD164 of SEQ ID NO: 15 may e.g. be used as a comparison, and any isoform, fused protein, functional derivative, or active fraction of a sCD164 variant should have an Emax of at least 75% of the original sCD164 variant or sCD164, and an EC50 of no more than ten times the value calculated for the original sCD164 variant.

In preferred embodiments, post-translationally modified forms of sCD164 variants may be used for the manufacture of a medicament for treatment and/or prevention of inflammatory and/or autoimmune disorders. Preferably, these proteins can be glycosylated, phosphorylated, and/or myristoylated.

The native extracellular domain of human CD164 is known to be modified, e.g. at the following positions of SEQ ID NO: 15:

a) Potential N-glycosylation sites are located at residues 3, 9, 18, 49, 54, 71, 81, 98 and 123;
b) Potential O-glycosylated sites are located at residues 11, 12, 17, 20, 21, 25, 26, 31, 32, 89, 90, 92, 96, 99, 100, 104, 108, 110, 111, 112, 113, 115, 117, 118, 119, 121, 122, 125, 127, 129, 130, 136.
c) Potential cAMP- and cGMP-dependent protein kinase phosphorylation sites are located at residues 134 to 137;
d) Potential Protein Kinase C phosphorylation sites are located at residues 100 to 102 and 112 to 114;
e) Potential Casein kinase II phosphorylation sites are located at residues 73 to 76 and 136 to 139;
f) Potential N-myristoylation site in CD164 is located at residue 119.

Similar modifications may be carried out at corresponding amino acid positions of the sCD164 variants of the invention. The alignment depicted in FIG. 1 allows easy determination of the corresponding amino acid positions.

A way to improve the stability of a sCD164 variant when administered to a subject is to generate multimers of the protein by fusing domains isolated from other proteins allowing the formation or dimers, trimers, etc. Examples for protein sequences allowing the multimerization of the polypeptides of the Invention are domains isolated from proteins such as hCG (WO 97/30161), collagen X (WO 04/33486), C4BP (WO 04/20639), Erb proteins (WO 98/02540), or coiled coil peptides (WO 01/00814).

In a preferred embodiment of the invention, the fused protein of a sCD164 variant comprises a portion of human chorionic gonadotropin (hCG).

In a further preferred embodiment, the sCD164 variant comprises an immunoglobulin fusion, i.e. the sCD164 variant is a fused protein comprising all or part of a sCD164 variant is fused to all or a portion of an immunoglobulin. Examples for such fusion proteins are represented by the constant/Fc region of human immunoglobulin proteins, allowing the dimerization common to human immunoglobulins. Different strategies for generating fusion protein comprising a therapeutic protein and an immunoglobulin fragment are known (WO 91/08298; WO 96/08570; WO 93/22332; WO 04/085478; WO 01/03737, WO 02/66514). For example, the nucleic acid sequence encoding the sCD164 variant can be cloned in an expression vector fused to a nucleic acid sequence encoding the sCD164 variant signal sequence (or any other appropriate signal /export sequence) at its 5' end, and the nucleic acid sequence encoding the constant region of human immunoglobulin lambda heavy chain IgG1 (NCBI Acc. No. CM75302; segment 246-477) at its 3' end (or vice versa). The resulting vector can be used to transform a CHO or HEK293 host cell line and the clones stably expressing and secreting the recombinant fusion protein having the sCD164 variant at the N-terminus and the IgG1 sequence at the C-terminus can be selected. This clone then can be used for scaling up the production and for purifying the recombinant fusion protein from the culture medium. Alternatively, the position of the nucleic acid encoding the constant region of human immunoglobulin lambda heavy chain IgG1 and the sCD164 variant can be inversed, and the resulting protein can be expressed and secreted by using an appropriate signal/export sequence.

The fusion between the sCD164 variant and the Ig-portion may be direct, or via a short linker peptide which can be as short as 1 to 3 amino acid residues in length or longer, for example, 13 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met introduced between the sCD164 variant sequence and the immunoglobulin sequence. The resulting fusion protein has preferably improved properties, such as an extended residence time in body fluids (half-life), increased specific activity, increased expression level, or the purification of the fusion protein is facilitated.

In a preferred embodiment, sCD164 variant is fused to the constant region of an Ig molecule. Preferably, it is fused to heavy chain regions, like the CH2 and CH3 domains of human IgG1, for example. Other isoforms of Ig molecules are also suitable for the generation of fusion proteins according to the present invention, such as isoforms $IgG_2$ or $IgG_4$, or other Ig classes, like IgM or IgA, for example. Fusion proteins may be monomeric or multimeric, hetero- or homomultimeric. Further amino acid substitutions may be carried out on the Fc part of the 1 g-fusion protein, e.g. for reduced binding to Fc receptors or other unwanted properties. An example of a sCD164-Fc variant is the protein of SEQ ID NO: 16. An example of a sCD164-Fc variant mutated in the Fc part is sCD164-Fcm (SEQ ID NO: 18).

A further aspect of the present invention relates to the use of a polynucleotide coding for a sCD164 variant for the manufacture of a medicament for treatment and/or prevention of inflammatory or/and autoimmune disorders, the sCD164 variant being chosen from:

a. A polypeptide having a sequence selected from SEQ ID NO: 1, 2, 3, 4, 5, 6, 7, 8, 9, 10, 11, 12, 13, 14, 16 or 18;
b. A polypeptide of (a) further comprising a signal sequence, preferably amino acids 1 to 23 of SEQ ID NO: 17;
c. A mutein of a polypeptide of (a) or (b), wherein the amino acid sequence has at least 90% or 91% or 92% or 93% or 94% or 95% identity to at least one of the sequences of (a) or (b);
d. A mutein of a polypeptide of (a) or (b) which is encoded by a DNA sequence hybridizing to the complement of the DNA sequence encoding a polypeptide of (a) or (b) under highly stringent conditions;
e. A mutein of a polypeptide of (a) or (b) wherein any changes in the amino acid sequence are conservative amino acid substitutions;
f. an isoform, fused protein, functional derivative, or active fraction of a polypeptide of (a) to (e).

The inflammatory and/or autoimmune disease that may be treated or prevented in accordance with the present invention, may be any inflammatory or autoimmune disease or condition, and is preferably selected from the group consisting of: multiple sclerosis, systemic lupus erythematosus, rheumatoid arthritis, juvenile idiopathic arthritis, psoriatic arthritis, osteoarthritis, spondylarthropathies, inflammatory bowel disease, endotoxemia, Crohn's disease, Still's disease, uveitis, Wegener's granulomatosis, Behcet's disease, scleroderma, Sjogren's syndrome, sarcoidosis, pyodema gangrenosum, polymyositis, dermatomyositis, myocarditis, psoriasis, systemic sclerosis, hepatitis C, allergies, allergic inflammation, allergic airway inflammation, chronic obstructive pulmonary disease (COPD), mesenteric infarction, stroke, ulcerative colitis, allergic asthma, bronchial asthma, mesenteric infarction, stroke, fibrosis, post-ischemic inflammation in muscle, kidney and heart, skin inflammation, glomerulonephritis, juvenile onset type I diabetes mellitus, hypersensitivity diseases, viral or acute liver diseases, alcoholic liver failure, tuberculosis, septic shock, HIV-infection, graft-versus-host disease (GVHD) and atherosclerosis.

The skin inflammation related disorders encompassed by the present invention might be psoriasis, eczema, burning and dermatitis. Skin inflammation related disorders may be contact hypersensitivity disorders such as contact dermatitis, wherein acute or chronic inflammation is produced by substances contacting the skin and causing toxic (irritant) or allergic reactions, are also within the invention.

Hepatitis is the inflammation of the liver usually caused by specific hepatitis viruses, alcohol, drugs, toxins or parasites. Acute viral Hepatitis is a diffuse liver inflammation caused by specific hepatotropic viruses (Hepatitis A, B, C, D, E and G and viruses). Chronic Hepatitis encompasses a spectrum of disorders between acute hepatitis and cirrhosis.

Ulcerative colitis is a chronic inflammation of the large intestine (colon). In patients with ulcerative colitis, ulcers and inflammation of the inner lining of the colon lead to symptoms of abdominal pain, diarrhea, and rectal bleeding. Ulcerative colitis is closely related to another condition of inflammation of the intestines called Crohn's disease. Together, they are frequently referred to as inflammatory bowel disease (IBD). Ulcerative colitis and Crohn's diseases are chronic conditions that can last years to decades.

Arthritis is a disease involving joint inflammation. The joints show swelling, stiffness, tenderness, redness or warmth. The joint symptoms may be accompanied by weight loss, fever or weakness. When these symptoms last for more than two weeks, inflammatory arthritis like rheumatoid arthritis may be the cause. Joint inflammation may also be caused by infection, which can lead to septic arthritis. A very common type of arthritis is degenerative joint disease (osteoarthritis). Joint inflammation is not a prominent feature of osteoarthritis.

A further aspect of the present invention relates to a sCD164 variant chosen from:

a. A polypeptide having a sequence selected from SEQ ID NO: 1, 2, 3, 4, 5, 6, 7, 8, 9, 10, 11, 12, 13, 14, 16 or 18;
b. A polypeptide of (a) further comprising a signal sequence, preferably amino acids 1 to 23 of SEQ ID NO: 17;
c. A mutein of a polypeptide of (a) or (b), wherein the amino acid sequence has at least 90% or 91% or 92% or 93% or 94% or 95% identity to at least one of the sequences of (a) or (b);
d. A mutein of a polypeptide of (a) or (b) which is encoded by a DNA sequence hybridizing to the complement of the DNA sequence encoding a polypeptide of (a) or (b) under highly stringent conditions;
e. A mutein of a polypeptide of (a) or (b) wherein any changes in the amino acid sequence are conservative amino acid substitutions;
f. an isoform, fused protein, functional derivative, or active fraction of a polypeptide of (a) to (e).

In a further aspect, the invention relates to a polynucleotide sequence encoding for a sCD164 variant of the invention. The polynucleotide may e.g. be present in a vector, for example an expression vector. The polynucleotide sequence encoding for a sCD164 variant of the invention can thus be used for the manufacture of a medicament for treatment and/or prevention of inflammatory or/and autoimmune disorders. These polynucleotides may be also used for the generation of non-human animals and plants that express recombinant sCD164 variants. The animals or plants can be transgenic, i.e. each of their cells contains a gene encoding the sCD164 variant, or, alternatively, a polynucleotide encoding the polypeptide can be introduced into somatic cells of the animal or plant, e.g. into mammary secretory epithelial cells of a mammal. In preferred embodiments, the non-human animal is a mammal such as a cow, sheep, goat, pig, or rabbit. Methods of making transgenic animals such as mammals are well known to those of skill in the art, and any such method can be used in the present invention. Moreover, transgenic mammals can be generated that secrete the recombinant soluble proteins polypeptides in their milk. Typically, the encoded polypeptide will include a signal sequence to ensure the secretion of the protein into the milk.

The polynucleotides encoding the sCD164 variants of the invention may be formulated in a composition or pharmaceutical composition for use in vitro and in vivo applications. A polynucleotide may be administered as "naked" polynucleotide, see WO 90/11092; WO 95/11307; Tascon et al., 1996. The transfer of a naked polynucleotide into cells may be proceeded with a particle bombardment (biolistic), said particles being DNA-coated microprojectiles accelerated to a high velocity allowing them to pierce cell membranes and enter cells without killing them, such as described by Klein et al. 1990. In a further embodiment, the polynucleotide of the invention may be entrapped in a liposome (Ghosh and Bacchawat, 1991; Wong et al., 1980; Nicolau et al., 1987). These liposomes may further be targeted to cells expressing LSR by incorporating leptin, triglycerides, afiponectin, or other known LSR ligands into the liposome membrane. The amount of vector to be injected to the desired host organism varies according to the site of injection. As an indicative dose, it will be injected between 0.1 and 100 µg of the vector in an animal body, preferably a mammal body, for example a mouse body. The vector may also be introduced in vitro in a host cell, preferably in a host cell previously harvested from the animal to be treated and more preferably a somatic cell such as a muscle cell. In a subsequent step, the cell that has been transformed with the vector coding for the desired sCD164 polypeptide or the desired fragment thereof is reintroduced into the animal body in order to deliver the recombinant protein within the body either locally or systemically.

For in vivo administration, the polynucleotides can be administered in any suitable formulation, at any of a range of concentrations (e.g. 1-500 µg/ml, preferably 50-100 µg/ml), at any volume (e.g. 1-100 ml, preferably 1 to 20 ml), and can be administered any number of times (e.g. 1, 2, 3, 5, or 10 times), at any frequency (e.g. every 1, 2, 3, 5, 10, or any number of days). Suitable concentrations, frequencies, modes of administration, etc. will depend upon the particular polynucleotide, vector, animal, etc., and can readily be determined by one of skill in the art.

In general, the sCD164 variants of the invention can be prepared by any procedure known in the art, including recombinant DNA-related technologies and chemical synthesis technologies.

Recombinant DNA-related technologies allow producing the sCD164 variants by first generating polynucleotides encoding them. These nucleic acids can be obtained by PCR from genomic DNA or, from a vector containing the full sequence of human CD164 (SEQ ID NO: 17) or any other relevant homologous sequences. The oligonucleotide primers complementary to the desired sequence contain restriction endonuclease sequences allowing the digestion by specific restriction endonucleases for further cloning, taking care to ensure that the sequence encoding the soluble protein is positioned properly with respect to the polyA signal and the rest of the other sequences in the expression plasmid.

Using common genetic engineering techniques, these polynucleotides can be cloned in replicable expression vector of viral or plasmid origin which are used to transform a prokaryotic or eukaryotic host cell, using episomal or non-/homologously integrated vectors, as well as transformation-, infection-, precipitation-, or transfection-based technologies. These vectors should allow the expression of the recombinant proteins in the prokaryotic or eukaryotic host cell under the control of their own transcriptional initiation/termination regulatory sequences, which are chosen to be constitutively active or inducible in said cell. A cell line substantially enriched in such cells can be then isolated to provide a stable cell line expressing the protein of interest.

Many books and reviews provides teachings on how to clone and produce recombinant proteins using vectors and Prokaryotic or Eukaryotic host cells, such as some titles in the series "A Practical Approach" published by Oxford University Press ("DNA Cloning 2: Expression Systems", 1995; "DNA Cloning 4: Mammalian Systems", 1996; "Protein Expression", 1999; "Protein Purification Techniques", 2001).

A typical expression vector comprises:

a) a DNA coding sequence, and b) an expression cassette;

wherein said sequence (a) is operably associated with a tissue-specific or a constitutive promoter included in sequence (b).

The expression vector may be any of the mammalian, yeast, insect or bacterial expression systems known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence can be optimized for the particular expression organism into which the expression vector is introduced (U.S. Pat. No. 5,082,767; Gustafsson C et al., 2004).

Generally, recombinant expression vectors will include origins of replication, selectable markers permitting transformation of the host cell, and a promoter derived from a highly expressed gene to direct transcription of a downstream structural sequence. The heterologous structural sequence is assembled in appropriate phase with translation initiation and termination sequences, and preferably a leader sequence capable of directing secretion of the translated protein into the periplasmic space or the extracellular medium. In a specific embodiment wherein the vector is adapted for transfecting and expressing desired sequences in mammalian host cells, preferred vectors will comprise an origin of replication in the desired host, a suitable promoter and enhancer, and also any necessary ribosome binding sites, polyadenylation sites, splice donor and acceptor sites, transcriptional termination sequences, and 5'-flanking non-transcribed sequences. DNA sequences derived from the SV40 viral genome, for example SV40 origin, early promoter, enhancer, splice and polyadenylation sites may be used to provide the required non-transcribed genetic elements.

The suitable promoter regions used in the expression vectors that may be used in the context of the present invention are chosen taking into account the cell host in which the heterologous gene is expressed. The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell, such as, for example, a human or a viral promoter. The promoter used may be constitutive or inducible.

A suitable promoter may be heterologous with respect to the nucleic acid for which it controls the expression or alternatively can be endogenous to the native polynucleotide containing the coding sequence to be expressed. Additionally, the promoter is generally heterologous with respect to the recombinant vector sequences within which the construct promoter/coding sequence has been inserted.

Promoter regions can be selected from any desired gene using, for example, CAT (chloramphenicol transferase) vectors and more preferably pKK232-8 and pCM7 vectors. Preferred bacterial promoters are the LacI, LacZ, the T3 or T7 bacteriophage RNA polymerase promoters, the gpt, lambda PR, PL and trp promoters (EP 0036776), the polyhedrin promoter, or the p10 protein promoter from baculovirus (Kit Novagen) (Smith et al., (1983) Mol Cell Biol 3(12):2156-65; O'Reilly et al., 1992), the lambda PR promoter or also the trc promoter. Eukaryotic promoters include CMV immediate early, HSV thymidine kinase, early and late SV40, LTRs from retrovirus, and mouse metallothionein-L. In addition, promoters specific for a particular cell type may be chosen, such as those facilitating expression in adipose tissue, muscle tissue, or liver. Selection of a convenient vector and promoter is well within the level of ordinary skill in the art.

Where a cDNA insert is used, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated, as an element of the expression cassette is a terminator. These elements can serve to enhance message levels and to minimize read through from the cassette into other sequences.

The vectors may also contain additional, non-coding sequences, including for example, but not limited to non-coding 5' and 3' sequences, vector sequence, sequences used for purification, probing, or priming. For example, heterologous sequences include transcribed, non-translated sequences that may play a role in transcription, and mRNA processing, for example, ribosome binding and stability of mRNA.

Selectable markers confer an identifiable change to the cell permitting easy identification of cells containing the expression construct. The selectable marker genes for selection of transformed host cells are preferably dihydrofolate reductase or neomycin resistance for eukaryotic cell culture, TRP1 for *S. cerevisiae* or tetracycline, rifampicin or ampicillin resistance in *E. coli*, or levan saccharase for mycobacteria, this latter marker being a negative selection marker.

As a representative but non-limiting example, useful expression vectors for bacterial use can comprise a selectable marker and a bacterial origin of replication derived from commercially available plasmids comprising genetic elements of pBR322 (ATCC 37017). Such commercial vectors include, but are not limited to, pKK223-3 (Pharmacia, Uppsala, Sweden) and pGEM1 (Promega Biotec, Madison, Wis., USA).

Large numbers of other suitable vectors are known to those of skill in the art, and are commercially available, such as the following bacterial vectors: pTrc-His, pET30-His, pQE70, pQE60, pQE-9 (Qiagen), pbs, pD10, phagescript, psiX174, pbluescript SK, pbsks, pNH8A, pNH16A, pNH18A, pNH46A (Stratagene); ptrc99a, pKK223-3, pKK233-3, pDR540, pRIT5 (Pharmacia); pWLNEO, pSV2CAT, pOG44, pXT1, pSG (Stratagene); pSVK3, pBPV, pMSG, pSVL (Pharmacia); pQE-30 (QIAexpress).

A suitable vector for the expression of polypeptides is a baculovirus vector that can be propagated in insect cells and in insect cell lines. A specific suitable host vector system is the pVL1392/1393 baculovirus transfer vector (Pharmingen) that is used to transfect the SF9 cell line (ATCC N°CRL 1711) which is derived from *Spodoptera frugiperda*. Further suitable baculovirus vectors are known to those skilled in the art, for example, FastBacHT. Other suitable vectors for the expression of an APM1 globular head polypeptide in a baculovirus expression system include, but are not limited to, those described by Chai et al. 1993; Vlasak et al. 1983; and Lenhard et al. 1996.

Further suitable vectors for the expression of polypeptides are mammalian vectors. A number of suitable vector systems are known to those skilled in the art, for example, pcDNA4HisMax, pcDNA3.1 Hygro-His and pcDNA3.1 Hygro.

Further suitable vectors for the expression of polypeptides are viral vector, such as the ones derived from an adenovirus.

Preferred adenovirus vectors according to the invention are those described by Feldman and Steg 1996 or Ohno et al. 1994.

Retrovirus vectors and adeno-associated virus vectors are generally understood to be the recombinant gene delivery systems of choice for the transfer of exogenous polynucleotides in vivo, particularly to mammals, including humans. These vectors provide efficient delivery of genes into cells, and the transferred nucleic acids are stably integrated into the chromosomal DNA of the host.

Another possibility to express polypeptides is to activate endogenously the genes by introducing regulatory sequence into the right locus of the genome by homologous recombination, thus operably linking the regulatory sequence with the gene, the expression of which is required to be induced (WO 91/09955; WO 02/10372).

The invention further relates to a host cell being modified to express a polypeptide of the invention, either by standard recombinant technologies, or modified by endogenous gene activation.

Suitable host cells may be either prokaryotic or eukaryotic. Preferred host cells are eukaryotic hosts, e.g. mammalian cells, such as human, monkey, mouse, and Chinese Hamster Ovary (CHO) cells, because they provide post-translational modifications to protein molecules, including correct folding or glycosylation at correct sites. Also yeast cells can carry out post-translational peptide modifications including glycosylation. A number of recombinant DNA strategies exist which utilize strong promoter sequences and high copy number of plasmids, which can be utilized for production of the desired proteins in yeast. Yeast recognizes leader sequences in cloned mammalian gene products and secretes peptides bearing leader sequences (i.e., pre-peptides).

Preferred host cells used as recipients for expressing the soluble proteins are the following:

a) Prokaryotic host cells: *Escherichia coli* strains (I.E. DH5-α strain), *Bacillus subtilis, Salmonella typhimurium*, and strains from species like *Pseudomonas, Streptomyces* and *Staphylococcus;* b) Eukaryotic host cells: HeLa cells (ATCC N°CCL2; N°CCL2.1; N°CCL2.2), Cv 1 cells (ATCC N°CCL70), COS cells (ATCC N°CRL1650; N°CRL1651), Sf-9 cells (ATCC N°CRL1711), C127 cells (ATCC N°CRL-1804), 3T3 (ATCC N° CRL-6361), CHO (ATCC N° CCL-61), human kidney 293 (ATCC N° 45504; N° CRL-1573), BHK (ECACC N° 84100501; N° 84111301), PLC cells, HepG2, and Hep3B.

For Eukaryotic hosts (e.g. yeasts, insect or mammalian cells), different transcriptional and translational regulatory sequences may be used, depending on the nature of the host. They may be derived form viral sources, such as adenovirus, bovine papilloma virus, Simian virus or the like, where the regulatory signals are associated with a particular gene which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated. The cells, which have been stably transformed by the introduced DNA can be selected by also introducing one or more markers which allow for selection of host cells which contain the expression vector. The marker may also provide for phototrophy to an auxotropic host, biocide resistance, e.g. antibiotics, or heavy metals such as copper, or the like. The selectable marker gene can either be directly linked to the DNA gene sequences to be expressed, or introduced into the same cell by co-transfection. Additional elements may also be needed for optimal synthesis of proteins of the invention.

If the nucleic acid encoding the soluble protein lacks a methionine to serve as the initiation site, an initiating methionine can be introduced next to the first codon of the nucleic acid using conventional techniques. Similarly, if the insert from the sCD164 variant cDNA lacks a poly A signal, this sequence can be added to the construct by, for example, splicing out the Poly A signal from pSG5 (Stratagene) using BgII and SaII restriction endonuclease enzymes and incorporating it into the mammalian expression vector pXT1 (Stratagene). pXT1 contains the LTRs and a portion of the gag gene from Moloney Murine Leukemia Virus. The position of the LTRs in the construct allow efficient stable transfection. The vector includes the Herpes Simplex Thymidine Kinase promoter and the selectable neomycin gene.

The sCD164 variants may be also be produced by chemical synthesis technologies, for example by solid phase synthesis and liquid phase synthesis. As a solid phase synthesis, for example, the amino acid corresponding to the C-terminus of the peptide to be synthesized is bound to a support which is insoluble in organic solvents, and by alternate repetition of reactions, one wherein amino acids with their amino groups and side chain functional groups protected with appropriate protective groups are condensed one by one in order from the C-terminus to the N-terminus, and one where the amino acids bound to the resin or the protective group of the amino groups of the peptides are released, the peptide chain is thus extended in this manner.

Solid phase synthesis methods are largely classified by the tBoc method and the Fmoc method, depending on the type of protective group used. Typically used protective groups include tBoc (t-butoxycarbonyl), Cl-Z (2-chlorobenzyloxycarbonyl), Br-Z (2-bromobenzyloxycarbonyl), Bzl (benzyl), Fmoc (9-fluorenylmethoxycarbonyl), Mbh (4,4'-dimethoxydibenzhydryl), Mtr (4-methoxy-2,3,6-trimethylbenzenesulphonyl), Trt (trityl), Tos (tosyl), Z (benzyloxycarbonyl) and Cl2-Bzl (2,6-dichlorobenzyl) for the amino groups; NO2 (nitro) and Pmc (2,2,5,7,8-pentamethylchromane-6-sulphonyl) for the guanidino groups; and tBu (t-butyl) for the hydroxyl groups). After synthesis of the desired peptide, it is subjected to the de-protection reaction and cut out from the solid support. Such peptide cutting reaction may be carried with hydrogen fluoride or tri-fluoromethane sulfonic acid for the Boc method, and with TFA for the Fmoc method. Totally synthetic proteins of a length comparable to the one of the proteins of the invention are disclosed in the literature (Brown et al., 1996; Muir, 2003; Casi, 2003).

The chemical synthesis of the soluble proteins allows expanding the natural repertoire of protein structure and function by making use of non-natural amino acids (Anthony-Cahill and Magliery 2002. These molecules can be designed on the sequence and/or the structure of the soluble proteins in order to select the residues can be chemically modified at the level of amino acid side chains, of amino acid chirality, and/or of the peptide backbone, and then to improve relevant properties, such as potency, easiness of purification, half-life. Preferred alternative, "synonymous" groups for amino acids to be included are those defined in Table II. The techniques for the synthesis and the development of these compounds are well known in the art (Hruby, 2000; Golebiowski, 2001; Villain et al., 2001, WO 02/10195;). Various methodology for incorporating unnatural amino acids into proteins, using both in vitro and in vivo translation systems, to probe and/or improve protein structure and function are also disclosed in the literature (Dougherty, 2000).

A further aspect of the invention relates to an antibody specifically reacting with a sCD164 variant of the invention, or an isoform, fused protein, functional derivative, or active fraction thereof.

The antibody may be monoclonal or synthetic, human, humanized, murine or chimeric.

The invention also relates to a process of production of a sCD164 variant, comprising the step of culturing the host cell of the invention under conditions suitable for expression of said sCD164 variant.

The cells may be cultured in any cell culture medium adapted for the specific cell type. If the host cell is a mammalian cell, the medium may contain fetal calf serum, or may preferably be serum-free. Examples for serum-free media include e.g. DMEM, optionally with Ham's F12 or ProCho5 medium.

In a further aspect of the invention, the process of production of a sCD164 variant comprises the step of isolating the sCD164 variant from the cell culture supernatant of a host cell. If the sCD164 variant is not secreted into the supernatant, it may also be isolated from the cells.

In a preferred embodiment, the process of production further comprises the step of purifying the sCD164 variant.

The purification of synthetic or recombinant soluble proteins that can be used according to the invention, may be carried out by any of the methods known for this purpose, i.e. any conventional procedure involving precipitation, chromatography (anion or cation exchange chromatography, phosphocellulose chromatography, hydrophobic interaction chromatography, affinity chromatography, hydroxylapatite chromatography and lectin chromatography), electrophoresis, differential extraction, salt fractionation, centrifugation or the like.

A purification procedure that may be used in preference is affinity chromatography using monoclonal antibodies, or any other chemical groups that bind the target protein (directly to the sCD164 variant or, if it is a fusion protein, the heterologous sequence such as e.g. an histidine tag or an Ig-portion) with sufficient affinity and specificity. The binding groups are produced and immobilized on a gel matrix contained within a column. Impure preparations containing the proteins are passed through the column. The soluble protein will be bound to the column by affinity while the impurities will pass through. After washing away remaining impurities, the soluble protein can be eluted from the gel by a change in pH or ionic strength. Alternatively, HPLC (High Performance Liquid Chromatography) can be used. The elution can be carried using a water-acetonitrile-based solvent commonly employed for protein purification.

In a preferred embodiment, the invention relates to the process of production further comprising the step of formulating the sCD164 variant into a pharmaceutical composition, and to a composition or pharmaceutical composition comprising a sCD164 variant of the invention.

In a further aspect, the invention relates to a composition or pharmaceutical composition comprising a sCD164 variant, mutein, isoform, fused protein, functional derivative, or active fraction. Such compositions may further comprise an additional active compound such as an immunosuppressant or anti-inflammatory substance, for simultaneous, sequential or separate use. Compounds that may be used in combination with a sCD164 variant of the invention include e.g. interferons, preferably interferon-β, or TNF-α antagonists, such as soluble forms of the TNF-receptors p55 or p75, also known as TBF-binding protein I and II (TBP-1, TBP-2), or derivatives thereof.

The pharmaceutical compositions of the invention may also contain any suitable pharmaceutically acceptable carriers, biologically compatible vehicles and additives that are suitable for administration to an animal (for example, physiological saline) and eventually comprising auxiliaries (like excipients, stabilizers or diluents) that facilitate the processing of the sCD164 variants into preparations that can be used pharmaceutically. The pharmaceutical compositions may be formulated in any acceptable way to meet the needs of the mode of administration. For example, the use of biomaterials and other polymers for drug delivery, as well the different techniques and models to validate a specific mode of administration, are disclosed in literature (Cleland, 2001; Luo B and Prestwich, 2001).

"Pharmaceutically acceptable" is meant to encompass any carrier, which does not interfere with the effectiveness of the biological activity of the active ingredient and that is not toxic to the host to which is administered. For example, for parenteral administration, the above active ingredients may be formulated in unit dosage form for injection in vehicles such as saline, dextrose solution, serum albumin and Ringer's solution.

Any accepted mode of administration can be used and determined by those skilled in the art to establish the desired blood levels of the active ingredients. For example, administration may be by various parenteral routes such as subcutaneous, intravenous, epidural, topical, intradermal, intrathecal, direct intraventricular, intraperitoneal, transdermal (e.g. in slow release formulations), intramuscular, intraperitoneal, intranasal, intrapulmonary (inhaled), intraocular, oral, or buccal routes. Parenteral administration can be by bolus injection or by gradual perfusion over time. Other particularly preferred routes of administration are aerosol and depot formulation. Sustained release formulations, particularly depot, of the invented medicaments are expressly contemplated.

Preparations for parenteral administration include sterile aqueous or non-aqueous solutions, suspensions, and emulsions, which may contain auxiliary agents or excipients known in the art, and can be prepared according to routine methods. In addition, suspension of the sCD164 variants as appropriate oily injection suspensions may be administered. Suitable lipophilic solvents or vehicles include fatty oils, for example, sesame oil, or synthetic fatty acid esters, for example, sesame oil, or synthetic fatty acid esters, for example, ethyl oleate or triglycerides. Aqueous injection suspensions that may contain substances increasing the viscosity of the suspension include, for example, sodium carboxymethyl cellulose, sorbitol, and/or dextran. Optionally, the suspension may also contain stabilizers. Pharmaceutical compositions include suitable solutions for administration by injection, and contain from about 0.01 to 99 percent, preferably from about 20 to 75 percent of sCD164 variant together with the excipient. Compositions that can be administered rectally include suppositories.

For parenteral (e.g. intravenous, subcutaneous, intramuscular) administration, the active protein(s) can be formulated as a solution, suspension, emulsion or lyophilised powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques. For transmucosal administration, penetrants appropriate to the barrier to be permeated are used in the formulation. Such penetrants are generally known in the art.

Pharmaceutical or physiologically acceptable preparations that can be taken orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner. For administration by inhalation, the compounds for use according to the present invention are conveniently delivered in the form of an aerosol spray presentation from pressurized packs or a nebulizer, with the use of a suitable gaseous propellant, e.g., carbon dioxide. In the case of a pressurized aerosol the dosage unit may be determined by providing a valve to deliver a metered amount. Capsules and cartridges of, e.g., gelatin, for use in an inhaler or insufflator, may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in aqueous vehicles, and may contain formulatory agents such as suspending, stabilizing and/or dispersing agents. Alternatively, the active ingredient may be in powder or lyophilized form for constitution with a suitable vehicle, such as sterile pyrogen-free water, before use.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days.

It is understood that the dosage administered will be dependent on the age, sex, health, and weight of the recipient, kind of concurrent treatment, if any, frequency of treatment, and the nature of the effect desired. The dosage will be tailored to the individual subject, as is understood and determinable by one of skill in the art. The total dose required for each treatment may be administered by multiple doses or in a single dose. The pharmaceutical composition of the present invention may be administered alone or in conjunction with other therapeutics directed to the condition, or directed to other symptoms of the condition. Usually a daily dosage of active ingredient is comprised between 0.01 to 100 milligrams per kilogram of body weight or more. Ordinarily 1 to 40 milligrams per kilogram per day given in divided doses or in sustained release form is effective to obtain the desired results. Second or subsequent administrations can be performed at a dosage, which is the same, less than, or greater than the initial or previous dose administered to the individual.

In a further aspect, the invention relates to a method of treating and/or preventing an inflammatory and/or autoimmune disease comprising administering to a host in need thereof an effective amount of a sCD164 variant, the sCD164 variant being chosen from:

a. A polypeptide having a sequence selected from SEQ ID NO: 1, 2, 3, 4, 5, 6, 7, 8, 9, 10, 13, 14, 16 or 18;
b. A polypeptide of (a) further comprising a signal sequence, preferably amino acids 1 to 23 of SEQ ID NO: 17;
c. A mutein of a polypeptide of (a) or (b), wherein the amino acid sequence has at least 90% or 91% or 92% or 93% or 94% or 95% identity to at least one of the sequences of (a) or (b);
d. A mutein of a polypeptide of (a) or (b) which is encoded by a DNA sequence hybridizing to the complement of the DNA sequence encoding any of (a) or (b) under highly stringent conditions;
e. A mutein of a polypeptide of (a) or (b) wherein any changes in the amino acid sequence are conservative amino acid substitutions;
f. an isoform, fused protein, functional derivative, or active fraction of a polypeptide of (a) to (e).

An "effective amount" refers to an amount of the active ingredients that is sufficient to affect the course and the severity of the disease, leading to the reduction or remission of such pathology. The effective amount will depend on the route of administration and the condition of the patient.

The amount of composition administered will, of course, be dependent on the subject being treated, on the subject's weight, the severity of the affliction, the manner of administration and the judgment of the prescribing physician. The dosage administered, as single or multiple doses, to an individual will vary depending upon a variety of factors, including pharmacokinetic properties, the route of administration, patient conditions and characteristics (sex, age, body weight, health, size), extent of symptoms, concurrent treatments, frequency of treatment and the effect desired.

The substances of the invention may be administered daily or every other day, of less frequent. Preferably, one or more of the substances of the invention are administered one, twice or three times per week. The daily doses are usually given in divided doses or in sustained release form effective to obtain the desired results. Second or subsequent administrations can be performed at a dosage which is the same, less than or greater than the initial or previous dose administered to the individual. A second or subsequent administration can be administered during or prior to onset of the disease.

According to the invention, the substances of the invention can be administered prophylactically or therapeutically to an individual prior to, simultaneously or sequentially with other therapeutic regimens or agents (e.g. multiple drug regimens), in a therapeutically effective amount. Active agents that are administered simultaneously with other therapeutic agents can be administered in the same or different compositions.

For any sCD164 variant used in the method of the invention, the therapeutically effective dose can be estimated initially from cell culture assays. For example, a dose can be formulated in animal models to achieve a circulating concentration range that includes or encompasses a concentration point or range shown to decrease cytokine expression in an in vitro system. Such information can be used to more accurately determine useful doses in humans. A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the LD50, (the dose lethal to 50% of the test population) and the ED50 (the dose therapeutically effective in 50% of the population). The dose ratio between toxic and therapeutic effects is the therapeutic index and it can be expressed as the ratio between LD50 and ED50. Compounds that exhibit high therapeutic indices are preferred. The data obtained from these cell culture assays and animal studies can be used in formulating a range of dosage for use in humans. The dosage of such compounds lies preferably within a range of circulating concentrations that include the ED50, with little or no toxicity. The dosage may vary within this range depending upon the dosage form employed and the route of administration utilized. The exact formulation, route of administration and dosage can be chosen by the individual physician in view of the patient's condition. (See, e.g., Fingi et al., 1975, in "The Pharmacological Basis of Therapeutics", Ch. 1).

The sCD164 variants of the invention may also be produced, formulated, administered, or used for the manufacture of a medicament for treatment and/or prevention of inflammatory or/and autoimmune disorders as an active derivative, a proteolysis-resistant modified form, a conjugate, a complex, a fraction, a precursor, and/or a salt.

The conjugate or complex can be formed with a molecule chosen amongst radioactive labels, biotin, fluorescent labels, cytotoxic agents, drug delivery agents. These conjugates or complexes can be generated, using molecules and methods known in the art, for example for allowing the detection of the interaction with other proteins (radioactive or fluorescent labels, biotin), for improving therapeutic efficacy (cytotoxic agents), or for improving drug delivery efficacy, using polymers such as polyethylene glycol and other natural or synthetic polymers (Pillai and Panchagnula, 2001).

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the polypeptide with consideration of effects on functional or antigenic domains of the polypeptide. There are a number of attachment methods available to those skilled in the art, e.g., EP 0 401 384, herein incorporated by reference (coupling PEG to G-CSF), see also Malik et al. (1992) Exp Hematol 20(8):1028-35, reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues, glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

A polypeptide resistant to proteolysis, can be generated by replacing a —CONH— peptide bond with one or more of the following: a (CH2NH) reduced bond; a (NHCO) retro inverso bond; a (CH2—O) methylene-oxy bond; a (CH2—S) thiomethylene bond; a (CH2CH2) carba bond; a (CO—CH2) cetomethylene bond; a (CHOH—CH2) hydroxyethylene bond); a (N—N) bound; a E-alcene bond; or a —CH═CH— bond. Thus, the invention also encompasses a soluble sCD164 or a variant thereof in which at least one peptide bond has been modified as described above. In addition, amino acids have chirality within the body of either L or D. In some embodiments it is preferable to alter the chirality of the amino acids in order to extend half-life within the body. Thus, in some embodiments, one or more of the amino acids are preferably in the L configuration. In other embodiments, one or more of the amino acids are preferably in the D configuration.

One specific embodiment for a method for delivering a soluble protein to the interior of a cell of a vertebrate in vivo comprises the step of introducing a preparation comprising a physiologically acceptable carrier and a naked polynucleotide operatively coding for the polypeptide of interest into the interstitial space of a tissue comprising the cell, whereby the naked polynucleotide is taken up into the interior of the cell and has a physiological effect. This is particularly applicable for transfer in vitro but it may be applied to in vivo as well.

A further aspect of the invention relates to a method of inhibiting the expression of one or more cytokines in an individual comprising administering to said individual a composition comprising a sCD164 variant of the invention. The cytokine can be TNF-α, IFN-γ, IL-2, IL-4, IL-5, or IL-10. These methods comprise providing or administering to individuals in need thereof said pharmaceutical or physiologically acceptable composition as described below, and can be considered as methods for preventing and/or treating inflammation and/or autoimmune disorders.

The present invention provides also provides novel screening assays and kits including soluble proteins comprising a polypeptide or polynucleotide of the invention, that can be used identify and compare the properties of compounds as inhibitors of cytokine secretion and expression. The kits and the assays may comprise a sCD164 variant of the invention, eventually labelled or immobilised on a solid support.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning an range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

Having now described the invention, it will be more readily understood by reference to the following examples that are provided by way of illustration and are not intended to be limiting of the present invention.

EXAMPLES

Abbreviations
AUC Area Under the Curve
ip intraperitoneal
iv intravenous
sc subcutaneous
s.e.m. standard error of the mean Example 1

Cloning, High Throughput Expression, and Purification in Mammalian Cells of sCD164 (SEQ ID NO: 15)

The cDNA sequence encoding the full extracellular region of human CD164 (residues 1-163 of NCBI Acc. No. NP_006007=SEQ ID NO: 17) was subcloned to generate an expression plasmid using Gateway™ cloning technology (Invitrogen). This expression plasmid allows the expression and the secretion of the mature form of the extracellular region of human CD164 (140 amino acids, i.e. 163 minus the 23 amino acid signal peptide of SEQ ID NO: 15) as a soluble protein having a hexa-histidine tag fused to its C-terminus. The tag served for affinity purification. The secretion is driven by the natural CD164 signal sequence (residues 1-23 of NCBI Acc. No. NP_006007/SEQ ID NO: 17).

The mammalian cells chosen for expression were Human Embryonic Kidney 293 cells expressing the Epstein-Barr virus Nuclear Antigen (HEK293-EBNA, Invitrogen).

The cells were maintained in suspension in Ex-cell VPRO serum-free medium (seed stock, maintenance medium, JRH Biosciences). Sixteen to 20 hours prior to transfection (transfection day −1), cells were seeded (density of $2 \times 10^5$ cells/ml) in 2× T225 flasks, each containing 50 ml DMEM (Dulbecco's modified Eagle's medium)/F12 (1:1) with 2% FBS (fetal bovine serum) seeding medium (JRH Biosciences). The next day (transfection day 0) the transfection took place by using the JetPEI™ reagent (2 μl/μg plasmid; PolyPlus-transfection). For each flask, 113 μg of the sCD164 expression plasmid were co-transfected with 2.3 μg of a plasmid expressing a fluorescent protein. The transfection mix was then added to the 2× T225 flasks and incubated at 37° C. (5% $CO_2$) for 6 days. Confirmation of positive transfection was done by microscopy (Axiovert 10 Zeiss) at day 1 and day 6 for qualitatively evaluating the fluorescence due to the fluorescent protein. On day 6 (harvest day), supernatants (100 ml) from the two flasks were pooled and centrifuged (4° C., 400 g) and placed into a vessel bearing a unique identifier.

The purification process was performed starting from 100 and 500 ml culture medium samples from cells expressing the C-terminal His-tagged recombinant protein. The samples were diluted with one volume cold buffer A (50 mM $NaH_2PO_4$; 600 mM NaCl; 8.7% (w/v) glycerol, pH 7.5) to final volumes of 200 and 1000 ml, respectively. The samples were filtered through a 0.22 μm sterile filter (Millipore, 500 ml filter unit) and kept at 4° C. in sterile square media bottle (Nalgene).

The purification was performed at 4° C. on the VISION workstation (Applied Biosystems) connected to an automatic sample loader (Labomatic). The purification procedure was composed of two sequential steps, metal affinity chromatography on a Poros 20 MC (Applied Biosystems) column charged with Ni ions (4.6×50 mm, 0.83 ml), followed by gel filtration on a Sephadex G-25 medium (Amersham Pharmacia) column (1.0×10 cm).

For the first chromatography step the metal affinity column (Ni-column) was regenerated with 30 column volumes of EDTA solution (100 mM EDTA; 1 M NaCl; pH 8.0), recharged with Ni ions through washing with 15 column volumes of a 100 mM NiSO$_4$ solution, washed with 10 column volumes of buffer A, followed by 7 column volumes of buffer B (50 mM NaH$_2$PO$_4$; 600 mM NaCl; 8.7% (w/v) glycerol, 400 mM; imidazole, pH 7.5), and finally equilibrated with 15 column volumes of buffer A containing 15 mM imidazole. The sample was transferred, by the Labomatic sample loader, into a 200 ml sample loop and subsequently charged onto the Ni metal affinity column at a flow rate of 10 ml/min. For the 1000 ml sample the charging procedure was repeated 5 times. The Ni-column was washed with 12 column volumes of buffer A, followed by 28 column volumes of buffer A containing 20 mM imidazole. During this wash, loosely attached contaminating proteins were eluted of the column. The recombinant His-tagged protein was finally eluted from Ni-column with 10 column volumes of buffer B at a flow rate of 2 ml/min, and the eluted protein was collected in a 1.6 ml fraction.

For the second chromatography step, the Sephadex G-25 gel-filtration column was regenerated with 2 ml of buffer D (1.137 M NaCl; 2.7 mM KCl; 1.5 mM KH$_2$PO$_4$; 8 mM Na$_2$HPO$_4$; pH 7.2), and subsequently equilibrated with 4 column volumes of buffer C (137 mM NaCl; 2.7 mM KCl; 1.5 mM KH$_2$PO$_4$; 8 mM Na$_2$HPO$_4$; 20% (w/v) glycerol; pH 7.4). The peak fraction eluted from the Ni-column was automatically, through the integrated sample loader on the VISION, loaded onto the Sephadex G-25 column and the protein was eluted with buffer C at a flow rate of 2 ml/min. The desalted sample was recovered in a 2.2 ml fraction. The fraction was filtered through a 0.22 μm sterile centrifugation filter (Millipore), aliquoted, frozen and stored at −80° C. An aliquot of the sample was analyzed on SDS-PAGE (4-12% NuPAGE gel; Novex) by Coomassie staining and Western blot with anti-His antibodies.

Coomassie staining was performed by incubating the NuPAGE gel in a 0.1% Coomassie blue R250 staining solution (30% methanol, 10% acetic acid) at room temperature for 1 hour. The gel was subsequently de-stained in 20% methanol, 7.5% acetic acid until the background was clear and the protein bands clearly visible.

For the Western blot, the proteins were electro-transferred from the NuPAGE gel to a nitrocellulose membrane at 290 mA for 1 hour at 4° C. The membrane was blocked with 5% milk powder in buffer E (137 mM NaCl; 2.7 mM KCl; 1.5 mM KH$_2$PO$_4$; 8 mM Na$_2$HPO$_4$; 0.1% Tween 20, pH 7.4) for 1 hour at room temperature, and subsequently incubated with a mixture of 2 rabbit polyclonal anti-His antibodies (G-18 and H-15, 0.2 ug/ml each; Santa Cruz) in 2.5% milk powder in buffer E overnight at 4° C. After further 1 hour incubation at room temperature, the membrane was washed with buffer E (3×10 min), and then incubated with a secondary HRP-conjugated anti-rabbit antibody (DAKO, HRP 0399) diluted 1/3000 in buffer E containing 2.5% milk powder for 2 hours at room temperature. After washing with buffer E (3×10 minutes), the membrane was developed with the ECL kit (Amersham Pharmacia) for 1 min. The membrane was subsequently exposed to a Hyperfilm (Amersham Pharmacia), the film developed and the western blot image visually analyzed.

The protein concentration in the samples was determined using the BCA protein assay kit (Pierce) with bovine serum albumin as standard.

sCD164 variants Ex-4, 5, 6 (SEQ ID NO: 1), Ex1 (SEQ ID NO: 3), Ex1,6 (SEQ ID NO: 4), Ex1, 4, 6 (SEQ ID NO: 5), Δ2,3 (SEQ ID NO: 6), Δ4 (SEQ ID NO: 8), Ext1, 2, 3 (SEQ ID NO: 9), Δ6 (SEQ ID NO: 11), Δ5 (SEQ ID NO: 12), A22E, G80E (SEQ ID NO: 13) and N9a, N18A (SEQ ID NO: 14), sCD164-Fc (SEQ ID NO: 16) and sCD164-Fcm (SEQ ID NO: 18) were produced and purified using the expression vector system, host cell and purification process described above for sCD164 (SEQ ID NO: 15).

Example 2

Effect of sCD164 Variants on Cytokine Release Measured in Cell-based Assays (Concavalin A Induced)

The effect of the sCD164 variants on Concanavalin A (Con A)-induced cytokine secretion was measured in an in vitro cytokine bead array (CBA). Cytokines measured included IL-2, IFN-γ, TNF-α, IL-5, IL-4 and IL-10.

Equipment and software:
96 well microtiter plate photometer EX (Labsystem).
Graph Pad Software (Prism)
Excel software (Microsoft)
Flow cytometer (Becton-Dickinson)
CBA Analysis software
Hood for cell culture
Incubator for cell culture
Centrifuge
Pipettes
Material and reagents:
Buffy coat (A concentrate of white cells and platelets obtained from 500 ml of centrifuged human whole blood)
DMEM (GIBCO)
Human serum type AB (SIGMA)
L-Glutamine (GIBCO)
Penicillin-Streptomycin (GIBCO)
Ficoll (PHARMACIA)
96 well microtiter plate for cell culture (COSTAR)
Concanavalin A (SIGMA)
Human Th1/Th2 Cytokine CBA Kit (Becton-Dickinson)
PBS (GIBCO)
Falcon 50 ml sterile tubes (Becton-Dickinson)
Bovine Serum Albumin (BSA; SIGMA)
Glycerol (MERCK)
Dimethyl Sulfoxide (DMSO; SIGMA)
96 well microtiter plate conical bottom (NUNC)
autoMACS™ Separator and MACS cell isolation kit (Miltenyl Biotec)
The cells were isolated as follows.
Human peripheral blood mononuclear cells (PBMC) were isolated from 500 ml of buffy coat diluted with DMEM. 25 ml of diluted blood was thereafter slowly added onto a 15 ml layer of Ficoll in a 50 ml Falcon tube, and tubes were centrifuged (2000 rpm, 20 minutes, at Room Temperature without brake). The interphase (ring) was then collected and the cells were washed with 25 ml of DMEM followed by a centrifuge step (1200 rpm, 5 min). This procedure was repeated three times. A buffy coat gave approximately $600 \times 10^6$ total cells.

The conditions applied for the cell-based assays were the following:
- 100000 cells/well in 96-well plates in 100 µl final in 2% glycerol.
- 5 ng/ml of the mitogen Concanavallin A (ConA).
- 48 hours for each assay.

The cells were prepared in each well by mixing
- 80 µl of $1.25 \times 10^6$ cells/ml were diluted in DMEM+2.5% Human Serum+1% L-Glutamine+1% Penicillin-Streptomycin.
- 10 µl of the solution containing sCD164 variant that was diluted in PBS+20% Glycerol (the final dilution of the proteins is 1/10);
- 10 µl ConA.

After 48 hours, cell supernatants were collected and human cytokines were measured by Human Th1/Th2 Cytokine CBA Kit (Becton-Dickinson).

The mixed Human Th1/Th2 Capture Beads suspension were prepared by vigorously vortexing for a few seconds before mixing with the samples from microwell plate. For each assay to be analyzed, 10 µl aliquot of each capture bead were added into a single tube labeled "mixed capture beads". The Bead mixture was thoroughly vortexed. The supernatants were diluted (1:4) using the Assay Diluent (20 µl of supernatants+60 µl of Assay Diluent). The sample dilution was then mixed before transferring samples into a 96 wells microtiter plate conical bottom (Nunc).

The human Th1/Th2 Cytokine CBA Assay was performed by adding 50 µl of the diluted supernatants into a 96 wells microtiter plate conical bottom (Nunc). 50 µl of the mixed capture beads were added followed by 50 µl addition of the Human Th1/Th2 PE Detection Reagent. The plate was then incubated for 3 hours at RT and protected from direct exposure to light followed by centrifugation at 1500 rpm for 5 minutes. The supernatant was then carefully discarded. In a subsequent step, 200 µl of wash buffer were twice added to each well, centrifuged at 1500 rpm for 5 minutes and supernatant carefully discarded. 130 µl of wash buffer were thereafter added to each well to resuspend the bead pellet. The samples were finally analyzed on a flow cytometer. The data were analyzed using the CBA Application Software, Activity Base and Microsoft Excel software.

The effect of the sCD164 variants on cytokine release from human PBMC cells (mixture) and isolated T cells was measured for six cytokines: TNF-α, IFN-γ, IL-2, IL-4, IL-5 and IL-10. The results are depicted in FIGS. 3 to 12.

For evaluation of the activity of the variants, the concentration of sCD164 variant at which the maximal effect is achieved ($E_{max}$), and the concentration of sCD164 variant at which 50% of the activity was achieved were determined. The results are summarized in FIG. 13.

Example 3

Effect of sCD164 and sCD164 Variants on Cytokine release Measured in Cell-based Assays (T Cell Receptor Mediated PBMC Activation)

The effect of the sCD164 (SEQ ID NO: 15), and sCD164 variants sCD164-Fc (SEQ ID NO: 16) and sCD164-Fcm (SEQ ID NO: 18), on the cytokine secretion (IL-2, TNF-α and IL-4) of PBMC cells following T cell receptor mediated activation (with anti human CD3 and anti human CD28 antibodies)

Materials and Reagents

Buffy coat
DMEM GIBCO Ref: 21331-020
Human serum type AB SIGMA Ref: H1513
L-Glutamine GIBCO Ref: 250 030-020
Penicillin-Streptomycin GIBCO Ref: 150 070-063
Ficoll PHARMACIA ref: 17-1440-03
96 well microtiter plate flat bottom for cell culture COSTAR Ref: 3596
96 well microtiter plate round bottom for cell culture COSTAR Ref: 3799
Dexamethasone water soluble SIGMA Ref: D2915
Human Th1/Th2 Cytokine CBA Kit Becton-Dickinson Ref: 550749
PBS GIBCO Ref: 14190-094
FALCON 50 ml sterile Becton-Dickinson Ref: 2070
Purified anti Human CD3 BD Pharmingen Ref: 555336
Purified anti Human CD28 BD Pharmingen Ref: 555725

Purification of Human PBMC from a Buffy Coat

The buffy coat was diluted form 1 to 2 with DMEM. Thereafter 30 ml of diluted blood were slowly added onto a 15 ml layer of Ficoll in a 50 ml Falcon tube, and the tubes were than centrifuged (2500 rpm, 20 min, at room temperature without brake).

The interphase (ring) was then collected and the cells were washed with 25 ml of DMEM followed by a centrifuge step (1500 rpm, 5 min). This procedure was repeated three times.

Activity Test
- 180 µl of $1.1 \times 10^6$ cells/ml, diluted in DMEM+2.5% Human Serum+1% L-Glutamine+1% Penicillin-Streptomycin, were added to a 96 well microtiter plate round bottom.
- 20 µl of the following solution containing sCD164 or sCD164 variants was added per well:
  - sCD164 dose response 10 points 109 µg/ml to 0.21 µg/ml
  - sCD164-Fc dose response 10 points 120 µg/ml to 0.23 µg/ml
  - sCD164-Fcm dose response 10 points 130 µg/ml to 0.25 µg/ml The mix was Incubated 2-3 hours at 37° C. with 5% CO2

Stimulation of Human PBMC

In a 96 well microtiter plate flat bottom, 50 µl of a solution of anti human CD3 at 5 µg/ml in PBS was added in each well.

The mix was incubated overnight at 4° C. and washed 3 times with PBS

Addition of 90 µl of the PBMC cells mix with sCD164 or sCD164 variants

Addition of 10 µl per well of a solution of anti human CD28 at 10 µg/ml in PBS

After 48 h, cell supernatants were collected and human cytokines measured by a specific immunoassay (ELISA, R&D Systems kits) and by Human Th1/Th2 Cytokine CBA Kit Becton-Dickinson.

Figure 14:
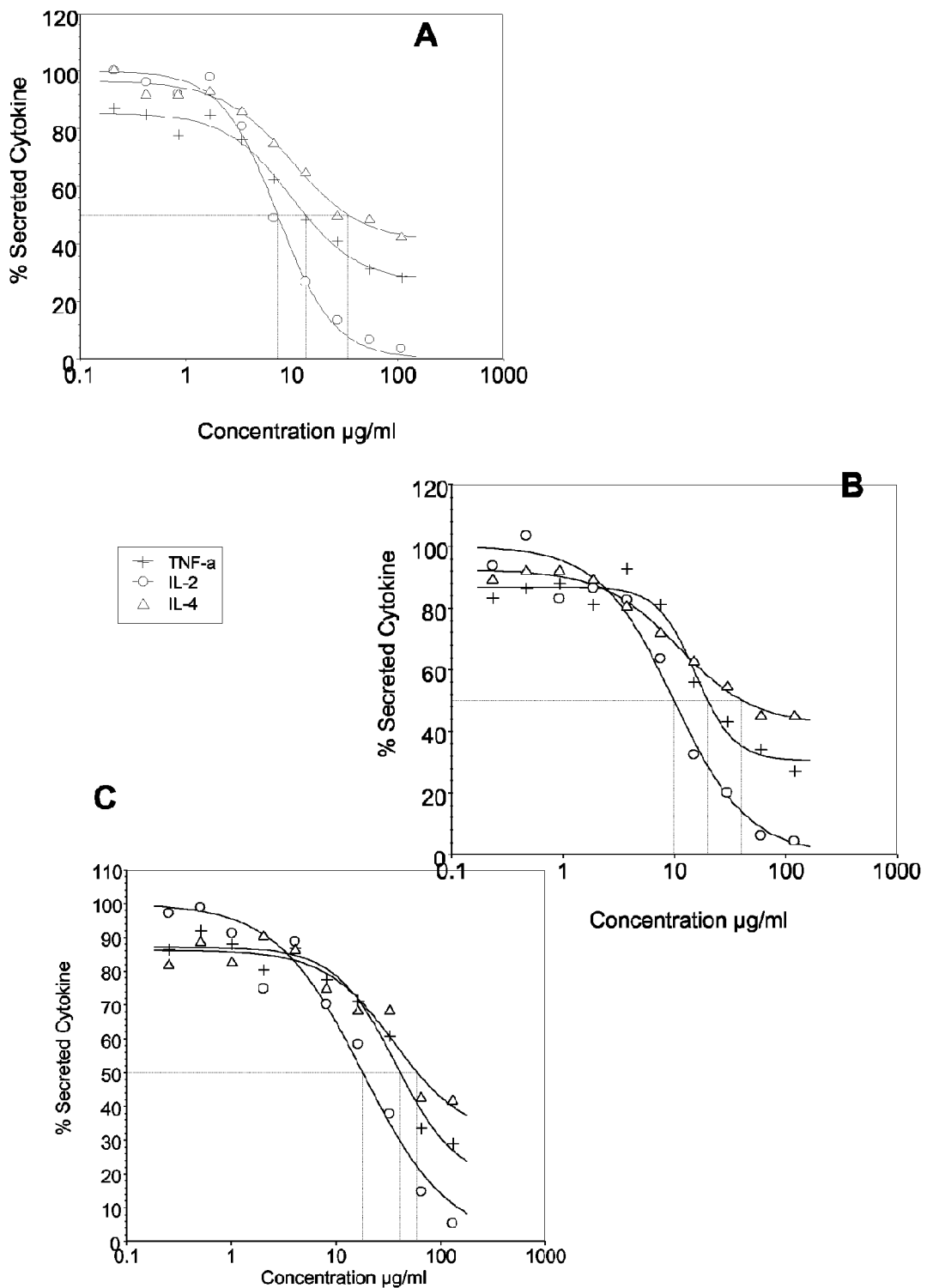
FIGS. 14A-14C show the effect of (FIG. 14A) sCD164 (SEQ ID NO: 15), of (FIG. 14B) sCD164-Fc variant (SEQ ID NO: 16) and (FIG. 14C) sCD164-Fcm variant (SEQ ID NO: 18) on the release of TNF-a, IL-2 and IL-4 from anti-CD3/anti-CD28 antibodies stimulated human PBMC. The X-axis represents the sCD164 variant concentration in μg/ml. The Y-axis represents the concentration of cytokine released in %.

Results (FIG. 14)

The three compounds tested, sCD164 (FIG. 14A), sCD164-Fc variant ((FIG. 14B) and sCD164-Fcm variant (FIG. 14C) decreased the release of the cytokines TNFa, IL-2 and IL-4 with equivalent efficacy (EC50=1-10 mcg/ml)

Example 4

Effect of sCD164 Variant on Immune Cells Recruitment in an Animal Model—Thioglycollate-induced Leukocyte Peritoneal Recruitment Assay The effect of a sCD164 variant on immune cells recruitment was tested using the thioglycollate-induced leukocyte peritoneal recruitment assay. In this example the capacity of ssCD164-Fc (SEQ ID NO: 16) to decrease monocytes/macrophage recruitment was evaluated.

Materials and Methods

The peritonitis was induced in 8 week old C3H mice (Elevage Janvier) by the injection of thioglycollate (1.5%, 40 ml/kg, ip). sCD164-Fc or the vehicle (PBS/0.02% BSA) was injected by subcutaneous or intravenous route at the doses of 0.003, 0.03 and 0.3 mg/kg 15 min before and 24 h after the challenge with thioglycolate. Forty-eight hours after the challenge, the animals were sacrificed and the lavage of the peritoneal cavity was conducted using 2×5 ml PBS-1 mM EDTA (+4° C.). After centrifugation (10 min at 3000 rpm), the pellet was resuspended in 1 ml PBS. The peritoneal cells were counted using a Beckman/Coulter counter. Dexamethasone (1 mg/kg), the anti-inflammatory compound was used as reference positive control.

Results sCD164-Fc administered by iv route at the doses of 0.003, 0.03 and 0.3 mg/kg reduced significantly the peritoneal recruitment of macrophages by 32%, 38% and 34%, respectively. Dexamethasone (1 mg/kg, iv) reduced the peritoneal recruitment of macrophages by 94%.

sCD164-Fc administered by sc route at the dose of 0.3 mg/kg reduced weakly, but significantly, the peritoneal recruitment of macrophages (−27%). Dexamethasone (1 mg/kg, sc) reduced the peritoneal recruitment of macrophages by 61%.

In this model, the positive effect of sCD164 variant on decreasing cell recruitment indicates the capacity of the molecule to diminish cell infiltration into inflamed tissues.

The efficacy of sCD164 (SEQ ID N: 15) and sCD164-Fc (SEQ ID NO: 16) was compared in independent head to head experiments. Both molecules reached similar efficacy indicating thereby that Fc effector functions are not required for the biological activity in the thioglycollate model.

Example 5

Effect of sCD164 Variant on Immune Cells Recruitment in an Animal Model—LPS-induced TNFalpha Release in Mice Previous experiments in this model have shown the capacity of sCD164 to decrease TNFα release after LPS induction. In the following experiment a head to head comparison of sCD164 (SEQ ID NO: 15), and sCD164 variant sCD164-Fc (SEQ ID NO: 16) was performed.

Materials and Methods

C3H mice (Elevage Janvier) (8 week old), received *E. Coli*'s LPS (O111:B4, Sigma, 0.3 mg/kg, ip) 15 minutes after the administration of the test molecules. LPS was solubilized in sterile saline. Dexamethasone (0.1 mg/kg, sc) was used as reference. 24 h later, the animals were sacrificed and the blood was sampled. Plasma levels of TNF-αwere determined in serum using an ELISA kit (R&D). Statistical analysis was determined with an ANOVA test followed by a post-test of Dunnett.

Results

Figure 15:
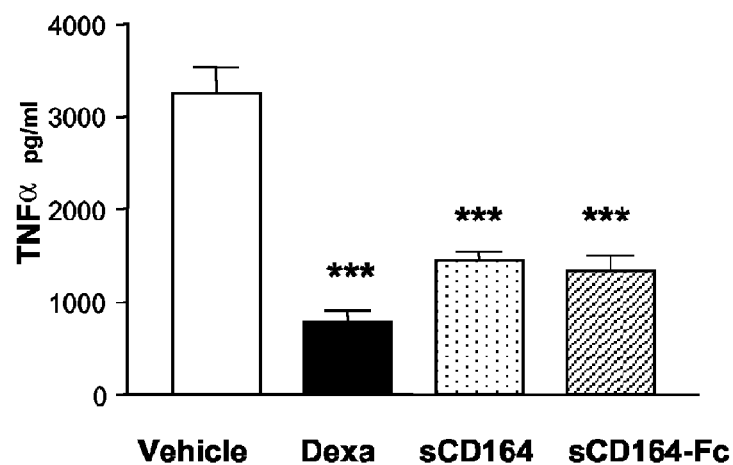
FIG. 15 shows the effect of sCD164 and sCD164-Fc (1 mg/Kg, iv) administration on TNF-α release in pg/ml in an animal model for LPS-induced TNF-α release. Dexamethasone was administered sc at 0.1 mg/kg.

Dexamethasone injected subcutaneously was able to significantly decrease LPS-induced TNFα ($P<0.001$). Both sCD164 molecules tested (sCD164 and sCD164-Fc) injected intravenously 15 minutes prior to LPS were able to significantly decrease the LPS-induced TNFα release, at the dose tested 1 mg/kg ($P<0.001$) (See FIG. 15).

Example 6

Effect of sCD164 Variant in a Model of Concanavalin A-induced Hepatitis in Mice

Several sCD164 variants have been shown in vitro to inhibit secretion of certain cytokines by ConA-stimulated human peripheral blood mononuclear cells (PBMC), see Examples 2 and 3 above. Since cytokines play a crucial role in T-cell induced ConA induced liver hepatitis (Seino et al. 2001, Kusters, 1996; Toyonaga et al. 1994), the present model was used to further test the sCD164 variants.

Materials and Methods 8 week old C3H mice (Elevage Janvier) received concanavaline A (Sigma, 20 mg/kg, iv in sodium acetate buffer (pH 5.0)), 1 hr after the subcutaneous administration of sCD164-Fc (0.1, 0.3 and 1 mg/kg) or vehicle (PBS/0.02% BSA). Eighteen hours later, the animals were sacrificed and the blood was sampled. Serum levels of transaminases (alanine transaminase (ALAT), aspartate aminotransferase (ASAT)) were determined in serum using a clinical analyzer (Hitachi). Dexamethasone (0.3 mg/kg, sc) was used as reference.

Figure 16:
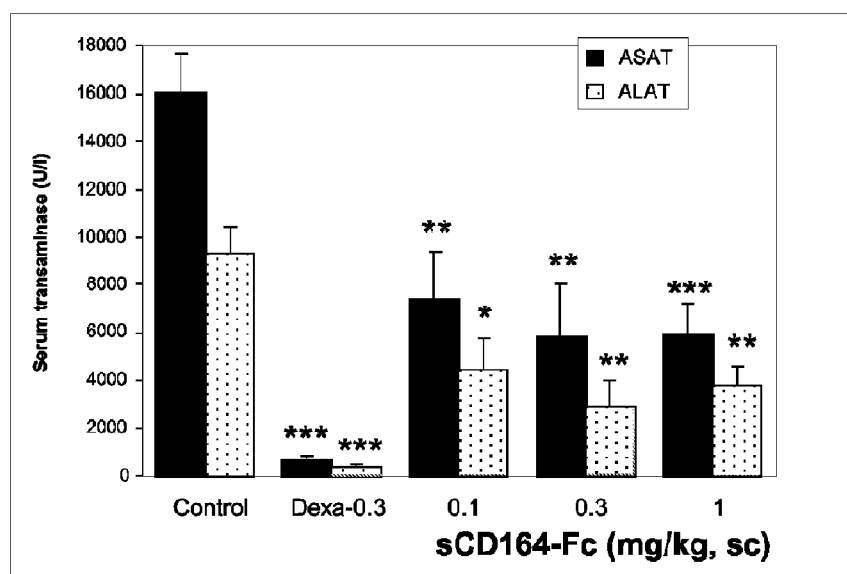
FIG. 16 shows the effect of sCD164-Fc at 0.1, 0.3 and 1 mg/kg (sc) and Dexamethasone (at 0.3 mg/kg, sc) on serum levels of transaminases ALAT and ASAT in a model of hepatitis induced by concanavaline A. Control: Vehicle treated (PBS/0.02% BSA).

Results (FIG. 16)

sCD164-Fc (SEQ ID NO: 16) administered at the doses of 0.1, 0.3 and 1 mg/kg, sc, reduced significantly the increase in serum transaminases (ALAT: −52%, −69% and −59%; ASAT: −54%, −64% and −63%, respectively) induced by concanavaline A. Dexamethasone (0.3 mg/kg, sc) reduced by 96% the level of serum transaminases.

The efficacy of sCD164 (SEQ ID N: 15) and sCD164-Fc (SEQ ID NO: 16) was compared in independent head to head experiments. Both molecules reached similar efficacy, indicating thereby that Fc effector functions are not required for the biological activity in the concanavaline A model.

Example 7

Effect of sCD164 Variant in a Model of Contact Hypersensitivity in Mice (CHS)

Contact hypersensitivity is a T cell mediated model of skin inflammation related disorders. In this model the hapten DNFB (dinitrofluorobenzene), which induces a type-1 cytokine response was used.

Materials and Methods

Female Balb/c 8-12 weeks years old were sensitized on day −5 and −4 by applying 35 μl of freshly prepared sensitizing solution (0.5% dinitrofluorobenzene-DNFB in acetone/oil, 4:1) onto the shaved abdomen. On day 0 CHS reaction was elicited (challenge, CH) by applying 10 μl of the challenging solution (0.2% DNFB in acetone/oil, 4:1) to the dorsal and ventral side of the right ear. sCD164-Fc (SEQ ID NO: 16) was administered at 0.1, 0.3, 1 3 mg/kg by iv route 30 minutes after DNFB challenge. As control, the left ear was challenged with an equal volume of vehicle (acetone/olive oil). Dexamethasone at 1 mg/kg and Enbrel® (Etanercept-soluble TNF receptor) at 30 mg/kg were used as positive controls and administered by sc route. Ear thickness was measured by means of a precision caliper in three different sites on ear surface, 24, 48 and 72 hours after challenge.

Results

Figure 17:
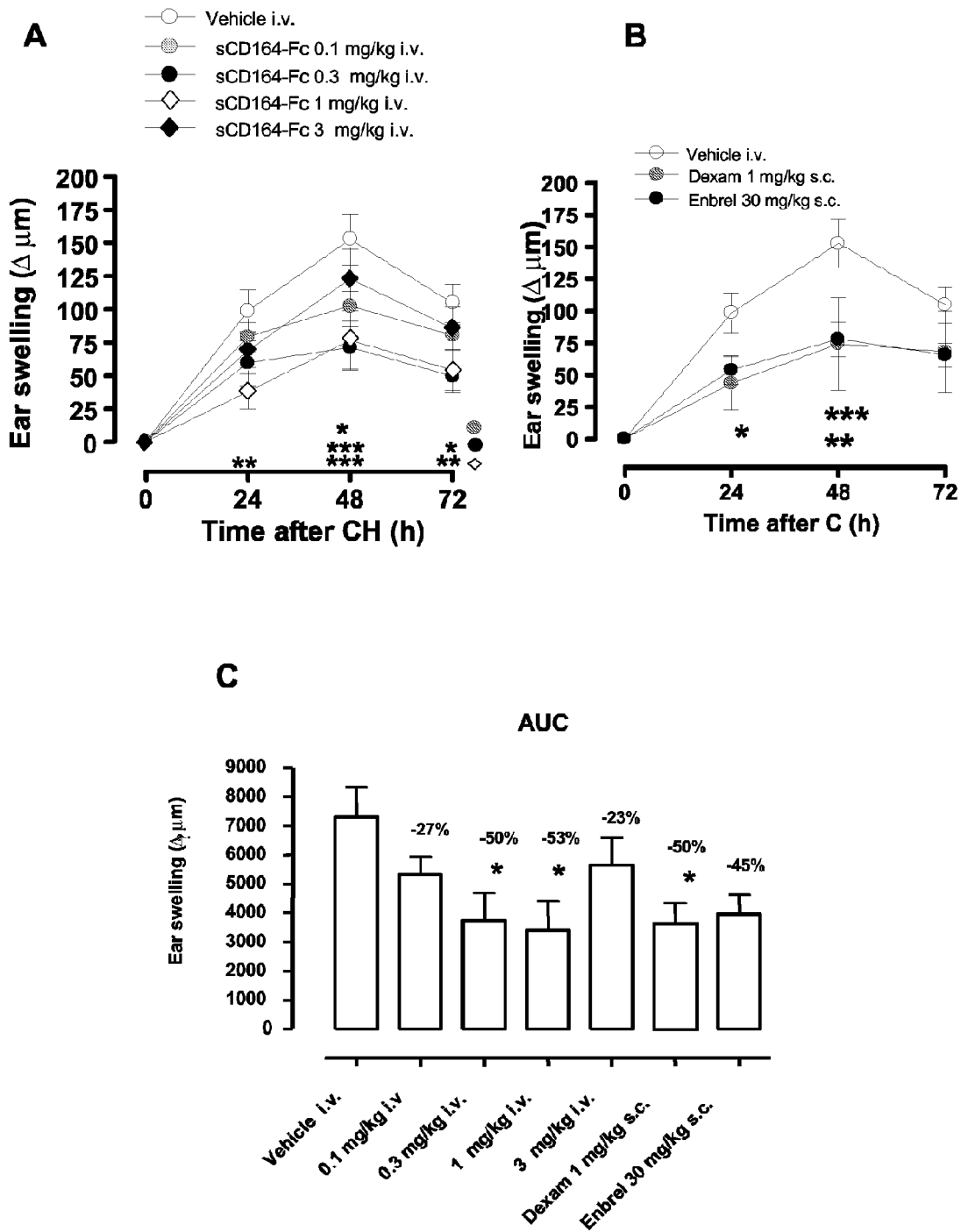
FIGS. 17A-17C show the inhibition of DNFB-induced ear swelling after (FIG. 17A) sCD164-Fc iv treatments at 0.1, 0.3, 1 and 3 mg/kg and (FIG. 17B) dexamethasone at 1 mg/kg and ENBREL at 30 mg/kg treatments via sc route.

As shown in FIG. 17, sCD164-Fc was able to significantly reduce ear swelling/edema at 0.3 and 1 mg/kg iv (FIG. 17A; p<0.01; two way ANOVA followed by Bonferroni's test). Maximal efficacy achieved by iv route at 1 mg/kg was −53% (FIG. 17C) overall the experimental period (0-72 h post challenge).

sCD164-Fc efficacy was compared with dexamethasone and Enbrel® (Etanercept-soluble TNF receptor) administered systemically at 1 mg/kg and 30 mg/kg sc, respectively, as shown in FIG. 17C. Efficacy achieved on AUC (Area Under the Curve) evaluation (0-72 h) at 1 mg/kg with sCD164-Fc is comparable to both dexamethasone and Enbrel®.

Example 8

Effect of sCD164 Variants in Dextran Sodium Sulfate-induced Ulcerative Colitis Disease Model The DSS model of colitis mimics some aspects of the human affection such as macrophage infiltration and up regulation of inflammatory cytokines (i.e. TNFα, IL-1p, IL-6) in the colon mucosa.

Materials and Methods

Ulcerative colitis (UC) was induced in female mice (Balb/c, 20-22 g, Elevage Janvier) by Dextran Sodium Sulfate (DSS 4%) administered in drinking water (oral route). The mice had free access to DSS during 7 days. Body weight was determined daily. The severity of the UC was assessed by a clinical score estimating the constituency of the stool (0=firm, 1=loose, 2=diarrhea) and the presence of blood (0=no blood, 1=occult blood, 2=gross rectal bleeding). Seven days after the induction of the disease, the animals were sacrificed. The length and the weight of the colon were determined and the ratio Weight/Length/100 g body weight was calculated. The spleen weight was also determined. Blood was sampled to determine serum amyloid protein (SAA) using a specific ELISA.

Test substances or vehicle (PBS/0.02% BSA) was administered at days 3, 4, 5 and 6 after the induction of the UC. Enbrel® (1 mg/kg, sc) was used as reference compound. Three studies were performed as per the following table:

| Substance | Study 1 | Study 2 | Study 3 |
|---|---|---|---|
| sCD164-Fcm (SEQ ID NO: 18) | 0.3, 1, 3 mg/kg ip | 0.3, 1, 3 mg/kg sc | 0.3, 1, 3 mg/kg sc |
| Enbrel ® | 1 mg/kg sc | 1 mg/kg sc | 1 mg/kg sc |
| Control - Water (Sham) | X | X | X |
| Control 4% DSS (Control) | X | X | X |
| sCD164-Fc (SEQ ID NO: 16) | — | — | 1 mg/Kg, sc |
| IgG1 | — | — | 1 mg/Kg, sc |

In Study 3, the content of IL-1β in the colon was also measured.

Results

Figure 18:
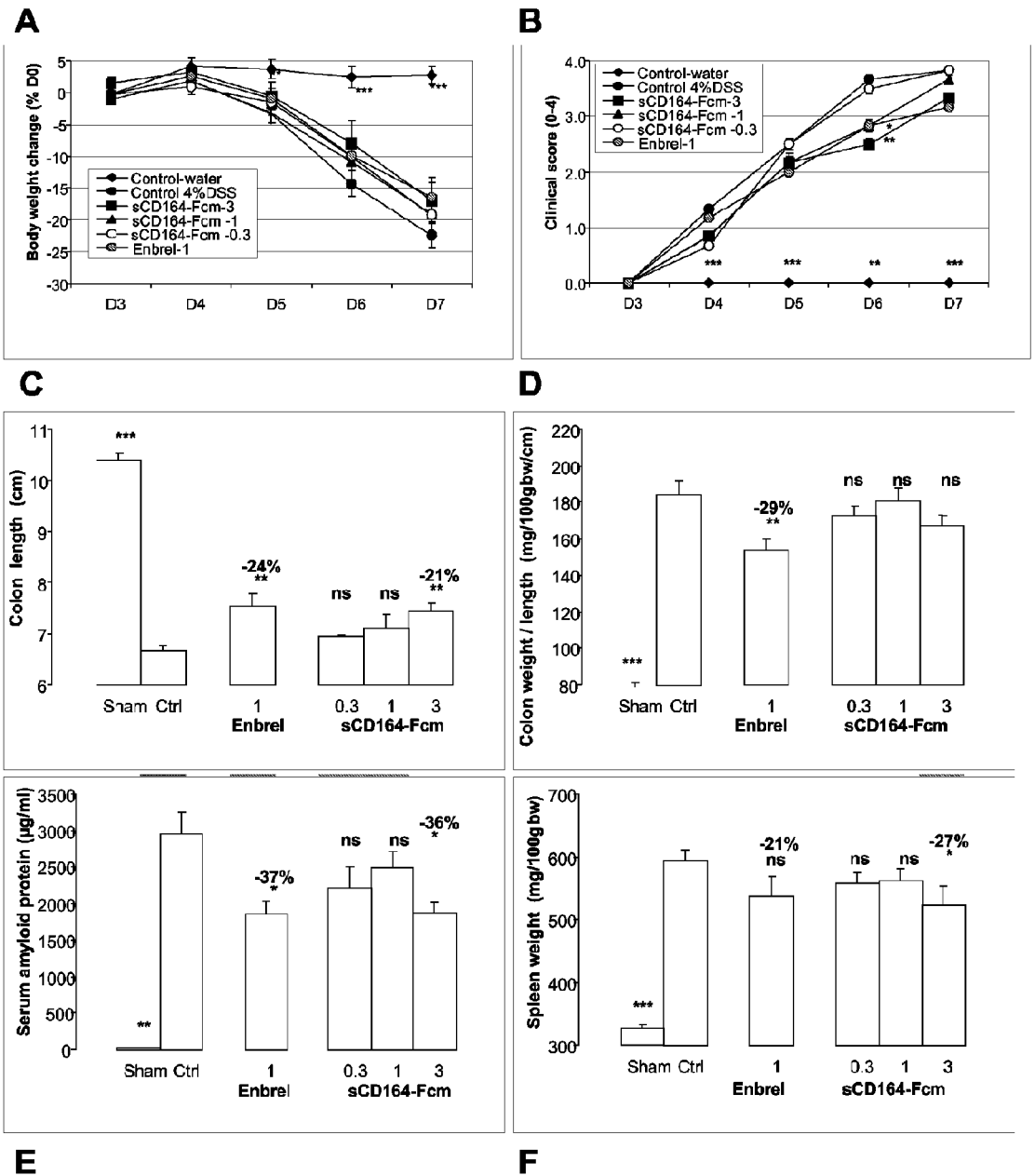
FIGS. 18A-18F show the effect of sCD164-Fcm at 0.3, 1 and 3 mg/kg (ip route), ENBREL at 1 mg/Kg (sc), control 4%DSS and water in a model of ulcerative colitis induced by 4% dextran sulfate sodium in mice (oral route) form D3 to D7 on the following parameters.

Study 1: (FIG. 18, A-F)

sCD164-Fcm (3 mg/kg, ip) prevented significantly the colon reduction (length −21%, FIG. 18C), the increase in serum amyloid protein A (−36%, FIG. 18E) and the splenomegaly (−27%, FIG. 18F). The clinical score was also significantly improved at day 6 when sCD164-Fcm was administered at the doses of 1 and 3 mg/kg, ip (−23% and −32%, respectively; FIG. 18D). The ratio weight/length and the body weight loss were not affected by the treatment with sCD164-Fcm (FIG. 18 D).

Enbrel® (1 mg/kg, ip) prevented significantly the colon reduction (length −24% and ratio weight/length −29%), the clinical score at day 6 (−23%) and the increase in serum amyloid protein A (−37%). The body weight loss and the splenomegaly were not prevented.

Figure 19:
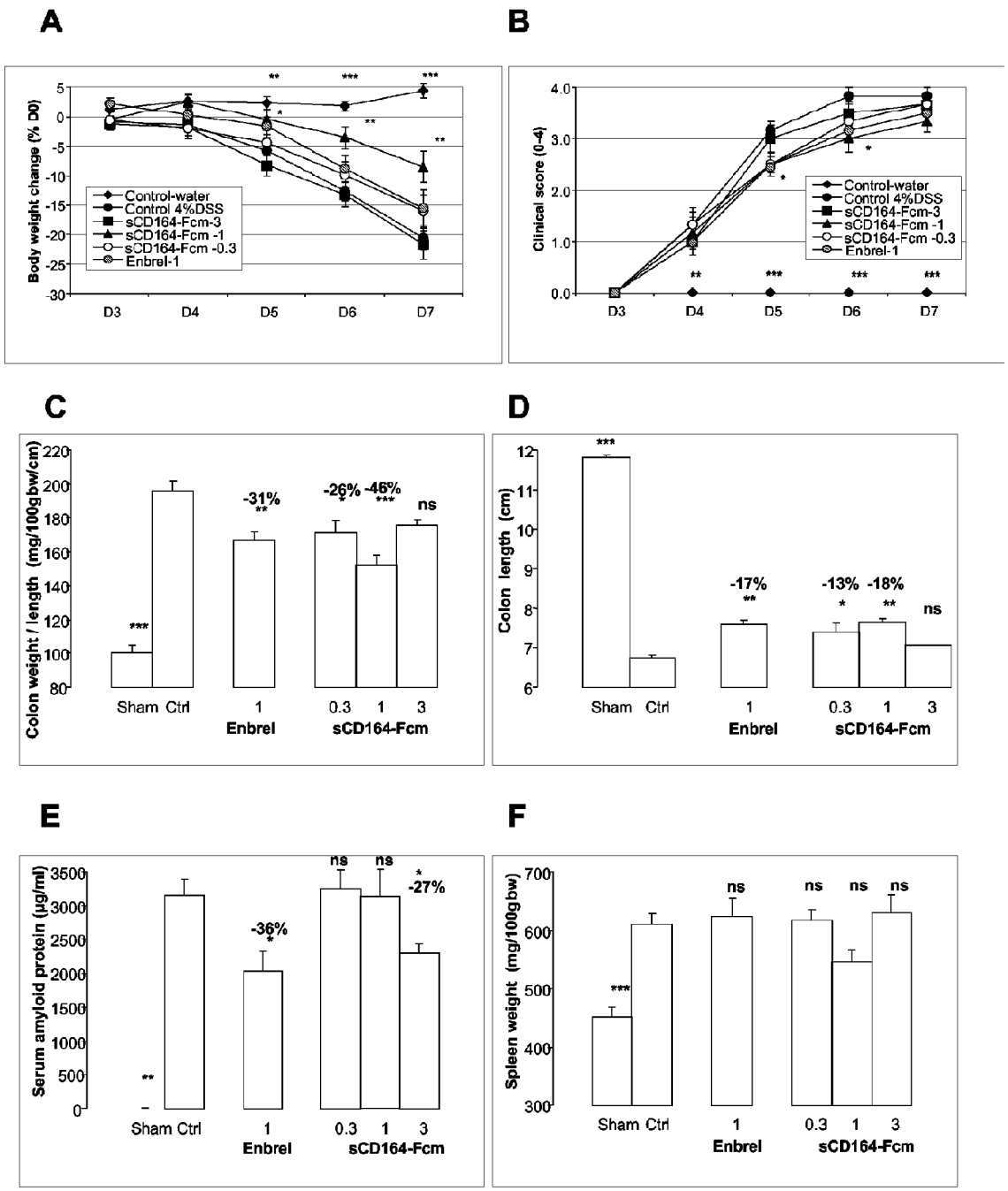
FIGS. 19A-19F show the effect of sCD164-Fcm at 0.3, 1 and 3 mg/kg (sc route), ENBREL at 1 mg/Kg (sc), control 4%DSS and water in a model of ulcerative colitis induced by 4% dextran sulfate sodium in mice (oral route) on the following parameters.

Study 2: (FIG. 19, A-F)

sCD164-Fcm (1 mg/kg, sc) reduced significantly the clinical score (day 6 (−22%)), the body weight loss (day 5 to day 7), the colon reduction (length (−18%) and ratio weight/length (−46%)). The increase in serum amyloid protein A was significantly decreased when sCD164-Fcm was administered at the dose of 3 mg/kg, sc. At the dose of 0.3 mg/kg, sc, sCD164-Fcm also prevented the colon reduction (length (−13%) and ratio weight/length (−26%)). The splenomegaly was not improved.

Enbrel® (1 mg/kg, sc) reduced significantly the clinical score (day 5 (−21%)), the colon reduction (length (−17%) and ratio weight/length (−31%)), and the increase in serum amyloid protein A (−36%). The splenomegaly was not improved.

Figure 20:
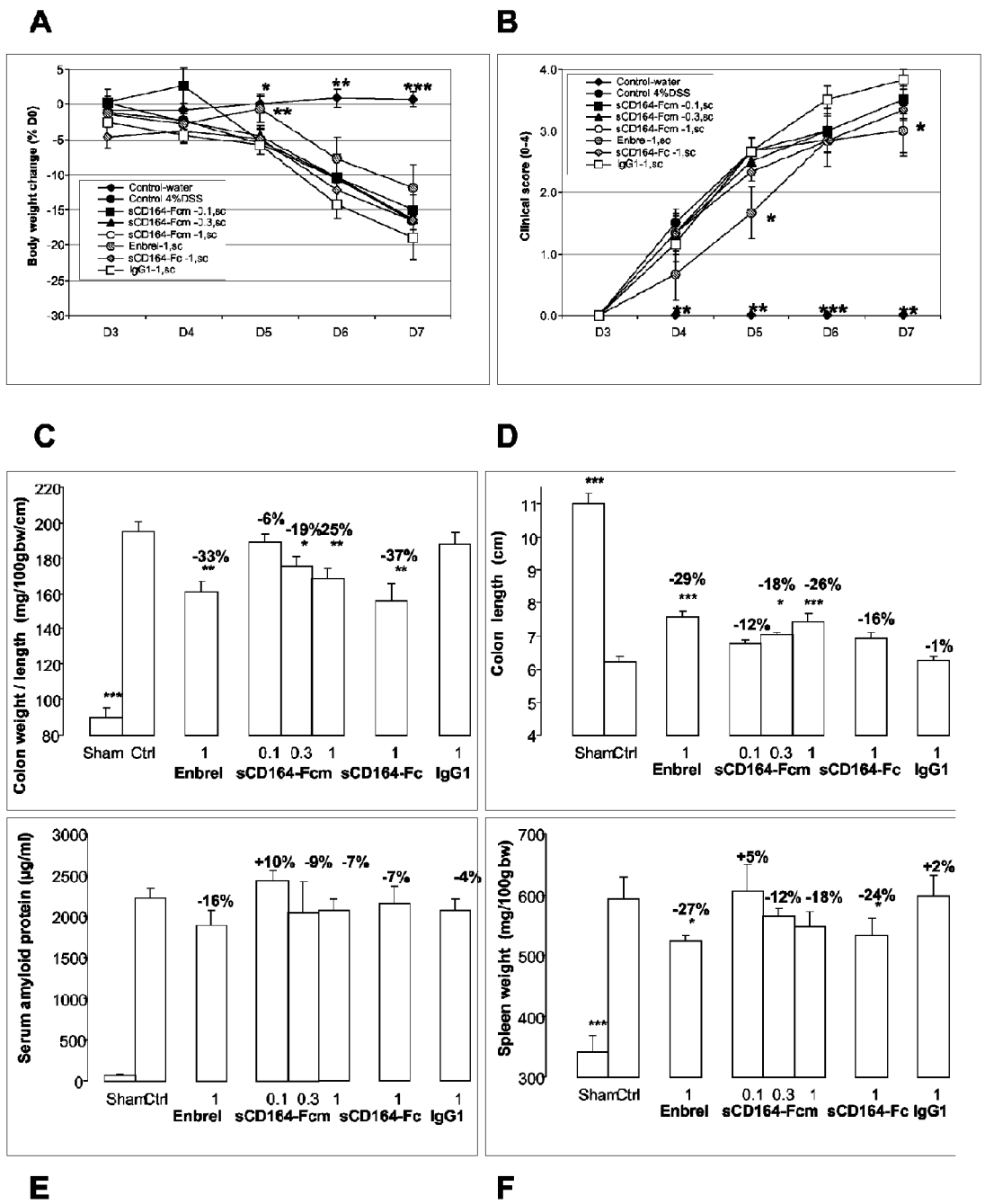
FIGS. 20A-20G show the effect of sCD164-Fcm at 0.1, 0.3 and 1 mg/kg (sc route), ENBREL at 1 mg/Kg (sc), sCD164-Fc at 1mg/kg, IgG1, control 4%DSS and water in a model of ulcerative colitis induced by 4% dextran sulfate sodium in mice (oral route) form D3 to D7 on the following parameters.
Figure 20:
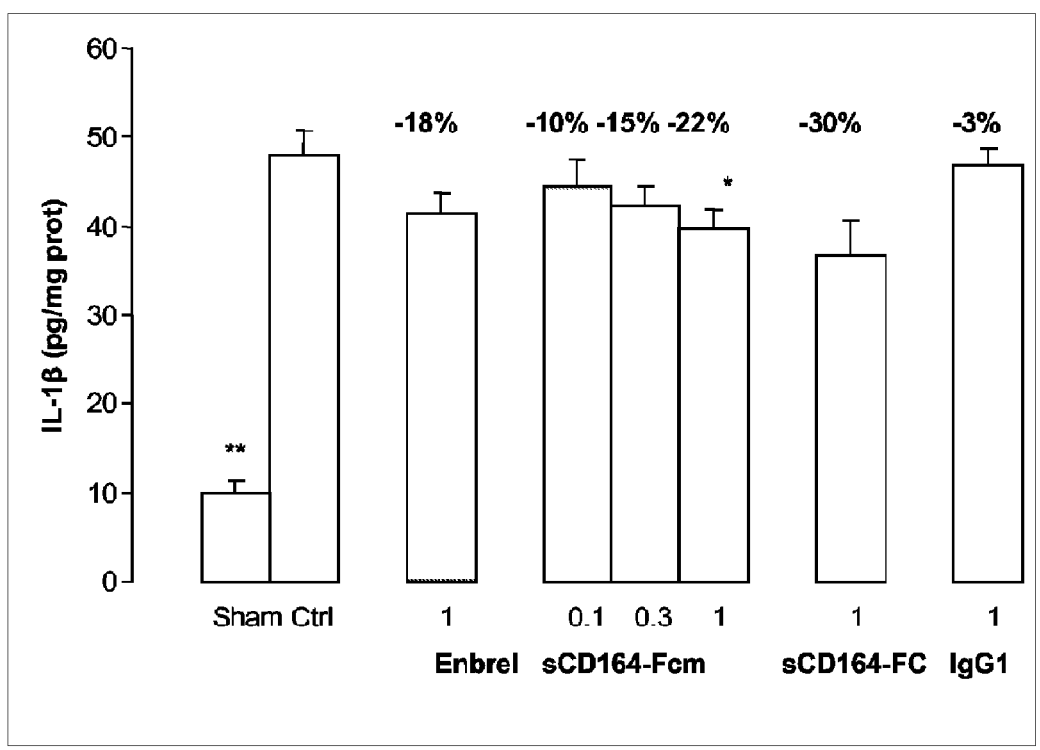

Study 3: (FIG. 20, A-G)

sCD164-Fcm (0.3 and 1 mg/kg, sc) improved significantly the colon reduction (length (−18% and −26%, respectively) and ratio weight/length (−19% and −25%, respectively)) and the content of IL-1β in colon (−22%). sCD164-Fcm trended to improve the clinical score and the splenomegaly but did not have any effect on body weight loss and serum amyloid A protein.

sCD164-Fc (1 mg/kg, sc) improved significantly the colon reduction and the splenomegaly. sCD164-Fcm tended to improve the clinical score and the content of IL-1β in colon but did not have any effect on body weight loss and serum amyloid A protein.

Enbrel® (1 mg/kg, sc) reduced significantly the clinical score (day 5 (−38%), day 7 (−30%), the colon reduction (length (−29%) and ratio weight/length (−33%)), the splenomegaly (−27%) and the body weight loss (day 5 (−83%)). Enbrel® trended to reduce serum amyloid protein A and the content of IL-1β in colon.

IgG1 did not improve any of the readouts.

Example 9

Effect of sCD164 Variant in K/B×N Serum Transfer Model of Arthritis in Mice

This is a passive model of arthritis, induced by serum transfer of K/B×N mice (spontaneously develop arthritis) to naïve mice. This model depends on macrophages and neutrophils. Inflammatory cytokines such as TNFα and IL-1β play an important role in the development of the disease.

Materials and Methods

Eight week old Balb/c mice (Charles River) received by iv route 150 μl of K/B×N serum (Charles McKay, Australia), containing high level of auto-antibodies against glucose-6- phosphate isomerase. They evolved severe arthritis assessed with a clinical score (0-12) evaluating the presence of swelling, erythema, edema, joint rigidity and ankylosis. The final score was the sum of scores on individual paws. The swelling of ankle, fore paw and hind paw was measure using a caliper. The clinical score and the swelling were determined every day. Fourteen days after the induction of the disease blood was sampled to determine osteocalcin and the legs were removed and fixed in formalin for histology.

sCD164-Fc or vehicle (PBS/0.02% BSA) were administered by ip route (Study Nr 1) or by sc route (Study Nr 2) once daily, 5 days a week, starting 3 days after the induction. Enbrel® (10 mg/kg, sc, once daily, 3 days a week) was used as reference compound.

Results

Figure 21:
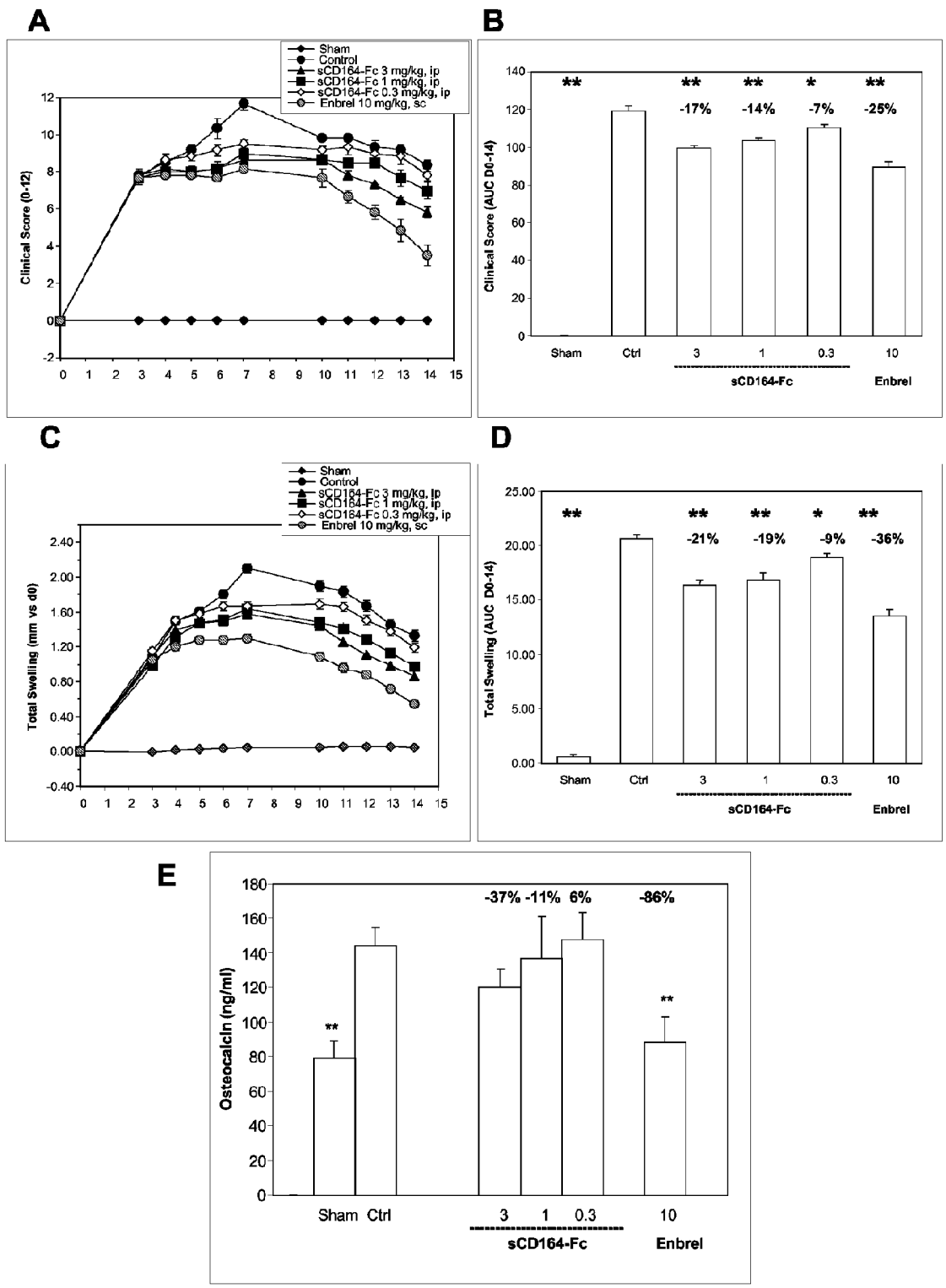
FIGS. 21A-21E show the effect of sCD164-Fc at 0.3, 1 and 3 mg/kg (ip route), ENBREL at 10 mg/Kg (sc), control (vehicle treated), in K/BxN serum transfer model of arthritis in mice.

Study 1: sCD164-Fc treatment by intraperitoneal route (FIG. 21, A-D)

sCD164-Fc, administered by ip route once daily, 5 days per week, at the doses of 0.3, 1 and 3 mg/kg, decreased significantly ($p<0.05$-$0.01$) the clinical score by 7%, 14% and 17%, and the paw swelling by 9, 19% and 21%, respectively. In addition sCD164-Fc (0.3, 1 and 3 mg/kg) trended to reduce serum osteocalcin (an index of bone degradation) by 6%, 11% and 37%, respectively. The efficacy of sCD164-Fc was dose dependent.

Enbrel®, administered by sc route once daily, 3 days per week, at the doses of 10 mg/kg, decreased significantly ($p<0.01$) the clinical score, the paw swelling and serum osteocalcin by 25%, 36% and 86%, respectively.

Figure 22:
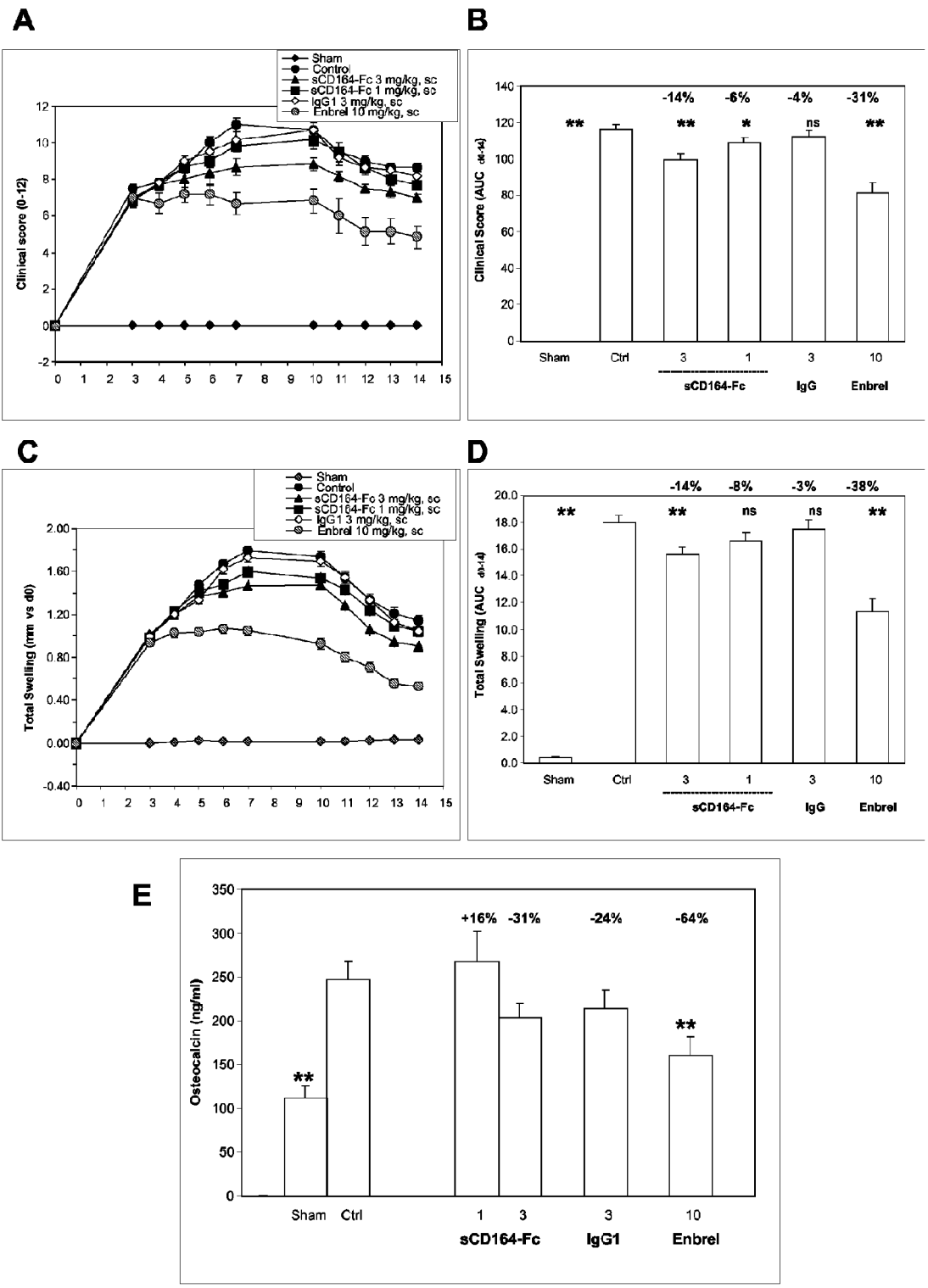
FIGS. 22A-22E show the effect of sCD164-Fc at 0.3, 1 and 3 mg/kg (sc route), ENBREL at 10 mg/Kg (sc), control (vehicle treated), in K/BxN serum transfer model of arthritis in mice.

Study 2: sCD164-Fc treatment by subcutaneous route (FIG. 22, A-D)

sCD164-Fc, administered by sc route once daily, 5 days per week, at the doses of 1 and 3 mg/kg, decreased significantly ($p<0.05$-$0.01$) the clinical score by 6% and 14%, respectively. The paw swelling was significantly reduced by 14% when sCD164-Fc was administered at the dose of 3 mg/kg. In addition sCD164-Fc trended to reduce serum osteocalcin (an index of bone degradation) by 16% and 31%, respectively. The efficacy of sCD164-Fc was dose dependent.

Enbrel®, administered by sc route once daily, 3 days per week, at the doses of 10 mg/kg, decreased significantly ($p<0.01$) the clinical score, the paw swelling and serum osteocalcin by 31%, 38% and 64%, respectively.

IgG1 had no preventive effect the paw swelling, the clinical score and serum osteocalcin.

Soluble CD164 variant, which diminishes macrophage recruitment and modulates TNFα, and IL-1β release, exhibit all the characteristics to modulate the outcome of the pathological process in this disease model.

Example 10

Effect of a sCD164 Variant on Administration on Cytokine Release Measured in the LPS Induced TNF-α Release Animal Model The model of lipopolysaccharide (LPS)-induced TNF-α release in mice is set up according the patent WO98/38179. LPS(O111:B4; SIGMA) is injected (0.3 mg/kg, ip) in C3H/HeN mice (Charles River, France). Ninety minutes later blood is sampled and plasma TNF-α is determined using an ELISA kit (R&D). The CD164 variant to be tested and dexamethasone are diluted in PBS and injected (Sf-CD164 at 0.03, 0.1 and 0.3 mg/kg, iv; or dexamethasone at 0.1 mg/kg, sc) 15 minutes prior to LPS administration.

Dexamethasone, the anti-inflammatory compound used as positive control, ($p<0.001$) inhibits LPS-induced TNF-α release by 72%. The CD164 variant is predicted to inhibits LPS-induced TNF-α release as well.

Example 11

Effect of a sCD164 Variant on Immune Cells Recruitment in Two Animal Models

The effect of a CD164 variant on immune cell recruitment can be tested using the thyoglicollate-induced leukocyte peritoneal recruitment assay.

The mice (strain C3H, 8 week old, n=6; Elevage Janvier, France) are injected with a CD164 variant (0.03, 0.1 and 0.3 mg/kg, iv) or dexamethasone (1 mg/kg, sc) diluted in PBS containing 0.02% BSA. Thioglycollate (1.5%, 40 ml/kg, ip; SIGMA) is injected 15 minutes after administration of the test molecules. A second administration of the test molecule is done 24 hours later. Forty-eight hours after the challenge with thioglycollate, the animals are sacrificed and the lavage of the peritoneal cavity is conducted using 2×5 ml PBS-1 mM EDTA (+4° C.). After centrifugation (10 min at 3000 rpm), the pellet is resuspended in 1 ml PBS. The peritoneal cells are counted using a Beckman/Coulter counter.

Dexamethasone inhibits significantly ($p<0.001$) the recruitment of macrophages in a dose dependent manner. It is predicted that the sCD164 variant inhibits thioglycollate-induced peritoneal recruitment of macrophages, lymphocytes and neutrophils as well.

LPS-induced peritoneal recruitment of neutrophils and lymphocytes is a further way of testing the sCD164 variants. The same administration protocol described above is used, but with LPS (O111:B4, Sigma; 0.9 mg/kg, 40 ml/kg, ip). The sCD164 variant is predicted to inhibit LPS-induced peritoneal recruitment of neutrophils and activated lymphocytes.

Example 12

Effect of a sCD164 Variant in a Cell-based Assay for MBP-specific Antigen Processing and Presentation An assay to test the effect of a sCD164 variant on the proliferation of myelin basic protein (MBP)-specific T cells induced by myelin basic protein peptide Ac1-11 (MBP(Ac1-11)) may be used. It has been shown that epicutaneous immunization (ECi) with the immuno-dominant peptide of myelin basic protein (MBP), Ac1-11, protects mice that are transgenic for an Ac1-11-specific T cell receptor against both the induced and spontaneous forms of experimental allergic encephalomyelitis (EAE).

Spleens from B10.PL and MBP transgenic mice are harvested and homogenized to obtain single cell suspensions. After erythrocyte lysis with Gay's solution, spienocytes are resuspended in PBS, washed and counted. After the isolation procedures, cellular viability is more than 90% by trypan blue dye exclusion. The B10.PL antigen presenting cells (APCs) are then irradiated with 25 Gy of g-irradiation (stimulants), washed and resuspended in complete medium at $1.9 \times 10^6$ cells/ml. The responder cell population is adjusted at $3.8 \times 10^6$ cells/ml in complete medium. 80 µl of each cell suspension per well are mixed in 96 well plates. The antigen is then added in a volume of 20 µl: 10 µg/ml of MBP murine or 1 µg/ml of Ac 1-11 MBP peptide per well (adequate negative controls are BSA, MSA and an irrelevant MBP-derived peptide respectively). The protein is added in a volume of 20 µl and then incubated at 37° C. in a humidified atmosphere with 5% CO2. After 3 days of culture, either the supernatants are harvested and frozen at −80° C. until testing for cytokine production or 1 μCi of ³H thymidine are added and counted for radioactivity incorporation after 14-16 hours of additional incubation.

A sCD164 variant may inhibit the proliferation of MBP specific T cells induced by Ac1-11. Thus, the active sCD164 variant might be useful in the treatment of multiple sclerosis.

Example 13

Effect of a sCD164 Variant in an Animal Model of Fulminant Liver Hepatitis

Several sCD164 variants have been shown in vitro to inhibit secretion of certain cytokines by ConA-stimulated human peripheral blood mononuclear cells (PBMC), see Example 2. Since cytokines play a crucial role in T-cell induced ConA induced liver hepatitis (Seino et al. 2001, Kusters, 1996; Toyonaga et al. 1994), this model may be used to further test the active CD164 variants.

Female C57/BL6 mice (8 weeks of age; IFFA CREDO) are used. In general, 7 animals per experimental group are used. Mice were maintained in standard conditions under a 12-hour light-dark cycle, provided irradiated food and water ad libitum.

Concanavalin A (ConA; Sigma ref.C7275) is injected at 18 mg/kg intravenously (iv) and blood samples are taken at 1.30 and 8 hours post-injection. The sCD164 variant is injected 30 minutes before ConA injection. Positive controls are injected with Dexamethasone (0.1 mg/kg), and negative control is injected with PBS-BSA 1.8% glycerol. At the time of sacrifice, blood is taken from the heart. IL-6 and IFN-gamma cytokine levels are measured using the TH1/TH2 CBA assay 1.5 hours after ConA injection. Transaminase blood parameters are determined using the COBAS instrument (Hitachi).

The experiment is predicted to show that the sCD164 variant protects from liver injury in a mouse model mimicking fulminant hepatitis after subcutaneous delivery of the sCD164 variant, since it may decrease relevant parameters such as transaminases levels (ALAT), IFN-γ, and IL-6 cytokine levels.

REFERENCES

1. Altschul et al., (1990) J Mol Biol 215(3):403-410
2. Altschul et al., (1993) Nature Genetics 3:266-272
3. Altschul et al., (1997) Nuc Acids Res 25:3389-3402
4. Anthony-Cahill S J and Magliery T J, Curr Pharm Biotechnol, 3: 285-97, 2002
5. Brown A et al., J Pept Sci 2:40-46, 1996
6. Brutlag et al. (1990) Comp. App. Biosci. 6:237-245
7. Casi G and Hilvert D, Curr Opin Struct Biol, 13: 589-94, 2003
8. Chai et al. (1993; Biotechnol Appl Biochem. December; 18 (Pt 3):259-73)
9. Chan Y H et al., J. Biol. Chem., 276:2139-2152, 2001
10. Cleland J L et al., Curr Opin Biotechnol, 12: 212-9, 2001
11. Dougherty D A, Curr Opin Chem Bio, 4: 645-52, 2000
12. Doyonnas et al., J Immunol, 165: 840-851, 2000
13. Feldman and Steg (1996; Semin Interv Cardiol 1(3): 203-8)
14. Ghosh and Bacchawat, (1991) Targeted Diagn Ther4: 87-103
15. Gonnet et al., (1992) Science 256(5062)
16. Golebiowski A et al., Curr Opin Drug Discov Devel, 4: 428-34, 2001
17. Grantham, Science, Vol. 185, pp. 862-864 (1974).
18. Gustafsson C et al., Trends Biotechnol, 22: 346-53, 2004
19. Henikoff and Henikoff (1993) Proteins 17(1):49-61
20. Higgins et al., (1996) Meth Enzymol 266:383-402
21. Hruby V J and Balse P M, Curr Med Chem, 7:945-70, 2000
22. Karlin and Altschul (1990) Proc Natl Acad Sci USA 87(6):2264-8
23. Kusters S, Gastroenterology 111 (2):462-71, 1996
24. Lee et al., Mol Cell Biol, 21: 7696-7706, 2001
25. Lenhard et al. (1996; Gene March 9; 169(2):187-90)
26. Luo B and Prestwich G D, Exp Opin Ther Patents, 11: 1395-1410, 2001
27. Matsui et al., J Biochem, 127: 1103-1107, 2000
28. Muir T W, Annu Rev Biochem, 72: 249-89, 2003
29. Nicolau et al., (1987) Methods Enzymol 149:157-76
30. Ohno et al. (1994; Science 265(5173):781-4)
31. Pearson and Lipman, (1988) Proc Natl Acad Sci USA 85(8):2444-8
32. Pillai O and Panchagnula R, Curr Opin Chem Biol, 5: 447-451, 2001
33. Seino et al. 2001, Annals of surgery 234, 681
34. Tascon et al., Nature Medicine 2: 888-892, 1996
35. Thompson et al., (1994) Nucleic Acids Res 22(2):4673-4680
36. Toyonaga et al. 1994, PNAS 91, 614-618
37. Villain M et al., Chem Biol, 8: 673-9, 2001, WO 02/10195
38. Vlasak et al. (1983; Eur J Biochem September 1; 135 (1):123-6)
39. Watt and Chan, Leuk Lymph, 37(: 1-25. 2000
40. Watt et al., Blood, 92: 849-866, 1998
41. Wong et al., (1980) Gene 10:87-94
42. Zannettino A, J Biol Regul Homeost Agents, 15: 394-396, 2001;
43. Zannettino et al. Blood, 92: 2613-2628, 1998
44. WO 90/11092
45. WO 95/11307

The invention claimed is:

1. An isolated sCD164 variant polypeptide selected from:
   (i) a polypeptide comprising SEQ ID NO: 16;
   (ii) a fusion protein comprising SEQ ID NO: 16 and a radioactive label, biotin, fluorescent label, cytotoxic agent or a polymer; or
   (iii) a polypeptide comprising SEQ ID NO: 16 and a signal sequence.

2. The isolated sCD164 variant polypeptide according to claim 1, wherein said sCD164 variant polypeptide comprises SEQ ID NO: 16.

3. The isolated sCD164 variant polypeptide according to claim 1, wherein said sCD164 variant polypeptide comprises SEQ ID NO: 16 and a radioactive label, biotin, fluorescent label, cytotoxic agent or a polymer.

4. The isolated sCD164 variant polypeptide according to claim 1, wherein said sCD164 variant polypeptide comprises SEQ ID NO: 16 and a signal sequence.

5. A composition comprising a pharmaceutically acceptable carrier and a sCD164 variant polypeptide selected from:
   (i) a polypeptide comprising SEQ ID NO: 16;
   (ii) a fusion protein comprising SEQ ID NO: 16 and a radioactive label, biotin, fluorescent label, cytotoxic agent or a polymer; or
   (iii) a polypeptide comprising SEQ ID NO: 16 and a signal sequence.

6. The composition according to claim 5, wherein said sCD164 variant polypeptide comprises SEQ ID NO: 16.

7. The composition according to claim 5, wherein said sCD164 variant polypeptide comprises SEQ ID NO: 16 and a radioactive label, biotin, fluorescent label, cytotoxic agent or a polymer.

8. The composition according to claim 5, wherein said sCD164 variant polypeptide comprises SEQ ID NO: 16 and a signal sequence.

* * * * *

UNITED STATES PATENT AND TRADEMARK OFFICE
CERTIFICATE OF CORRECTION

PATENT NO. : 7,803,910 B2  
APPLICATION NO. : 11/814389  
DATED : September 28, 2010  
INVENTOR(S) : Gabriela Saborio et al.

Page 1 of 2

It is certified that error appears in the above-identified patent and that said Letters Patent is hereby corrected as shown below:

Column 4,
Lines 27-28, "haematopoisesis" should read --haematopoiesis--.

Column 6,
Line 9, "sCD164-Fe" should read --sCD164-Fc--.

Column 7,
Line 31, "(μg/m1)" should read --(μg/ml)--.
Line 44, "Il-1β" should read --IL-1β--.
Line 58, "(FIG. 21A)" should read --(FIG. 22A)--.

Column 14,
Line 30, "CM75302" should read --CAA75302--.
Line 65, "1 g-fusion" should read --Ig-fusion--.

Column 26,
Line 19, "Fingi et al." should read --Fingl et al.--.

Column 27,
Line 67, "an range" should read --and range--.

Column 33,
Line 67, "TNF-αwere" should read --TNF-α were--.

Column 35,
Line 30, "IL-1p" should read --IL-1β--.

Column 38,
Line 52, "spienocytes" should read --splenocytes--.

Signed and Sealed this
Fifteenth Day of February, 2011

David J. Kappos
*Director of the United States Patent and Trademark Office*

Column 55,
Line 67, "sCD 164" should read --sCD164--.

Column 56,
Line 60, "sCD 164" should read --sCD164--.

SEQUENCE LISTING

<160> NUMBER OF SEQ ID NOS: 18

<210> SEQ ID NO 1
<211> LENGTH: 53
<212> TYPE: PRT
<213> ORGANISM: homo sapiens

<400> SEQUENCE: 1

-continued

Val Ser Thr Ala Thr Pro Val Pro Thr Ala Asn Ser Thr Ala Lys Pro
1               5                   10                  15

Thr Val Gln Pro Ser Pro Ser Thr Thr Ser Lys Thr Val Thr Thr Ser
            20                  25                  30

Gly Thr Thr Asn Asn Thr Val Thr Pro Thr Ser Gln Pro Val Arg Lys
            35                  40                  45

Ser Thr Phe Asp Ala
        50

<210> SEQ ID NO 2
<211> LENGTH: 77
<212> TYPE: PRT
<213> ORGANISM: homo sapiens

<400> SEQUENCE: 2

Asp Glu Ser Tyr Cys Ser His Asn Ser Thr Val Ser Asp Cys Gln Val
1               5                   10                  15

Gly Asn Thr Thr Asp Phe Cys Ser Val Ser Thr Ala Pro Val Pro
            20                  25                  30

Thr Ala Asn Ser Thr Ala Lys Pro Thr Val Gln Pro Ser Pro Ser Thr
            35                  40                  45

Thr Ser Lys Thr Val Thr Thr Ser Gly Thr Thr Asn Asn Thr Val
        50                  55                  60

Pro Thr Ser Gln Pro Val Arg Lys Ser Thr Phe Asp Ala
65                  70                  75

<210> SEQ ID NO 3
<211> LENGTH: 35
<212> TYPE: PRT
<213> ORGANISM: homo sapiens

<400> SEQUENCE: 3

Asp Lys Asn Thr Thr Gln His Pro Asn Val Thr Leu Ala Pro Ile
1               5                   10                  15

Ser Asn Val Thr Ser Ala Pro Val Thr Ser Leu Pro Leu Val Thr Thr
            20                  25                  30

Pro Ala Pro
        35

<210> SEQ ID NO 4
<211> LENGTH: 56
<212> TYPE: PRT
<213> ORGANISM: homo sapiens

<400> SEQUENCE: 4

Asp Lys Asn Thr Thr Gln His Pro Asn Val Thr Leu Ala Pro Ile
1               5                   10                  15

Ser Asn Val Thr Ser Ala Pro Val Thr Ser Leu Pro Leu Val Thr Thr
            20                  25                  30

Pro Ala Pro Gly Thr Thr Asn Asn Thr Val Thr Pro Thr Ser Gln Pro
            35                  40                  45

Val Arg Lys Ser Thr Phe Asp Ala
        50                  55

<210> SEQ ID NO 5
<211> LENGTH: 69
<212> TYPE: PRT
<213> ORGANISM: homo sapiens

<400> SEQUENCE: 5

```
Asp Lys Asn Thr Thr Gln His Pro Asn Val Thr Thr Leu Ala Pro Ile
1               5                   10                  15

Ser Asn Val Thr Ser Ala Pro Val Thr Ser Leu Pro Leu Val Thr Thr
                20                  25                  30

Pro Ala Pro Val Ser Thr Ala Thr Pro Val Pro Thr Ala Asn Ser Thr
            35                  40                  45

Gly Thr Thr Asn Asn Thr Val Thr Pro Thr Ser Gln Pro Val Arg Lys
        50                  55                  60

Ser Thr Phe Asp Ala
65

<210> SEQ ID NO 6
<211> LENGTH: 88
<212> TYPE: PRT
<213> ORGANISM: homo sapiens

<400> SEQUENCE: 6

Asp Lys Asn Thr Thr Gln His Pro Asn Val Thr Thr Leu Ala Pro Ile
1               5                   10                  15

Ser Asn Val Thr Ser Ala Pro Val Thr Ser Leu Pro Leu Val Thr Thr
                20                  25                  30

Pro Ala Pro Val Ser Thr Ala Thr Pro Val Pro Thr Ala Asn Ser Thr
            35                  40                  45

Ala Lys Pro Thr Val Gln Pro Ser Pro Ser Thr Ser Lys Thr Val
        50                  55                  60

Thr Thr Ser Gly Thr Thr Asn Asn Thr Val Thr Pro Thr Ser Gln Pro
65                  70                  75                  80

Val Arg Lys Ser Thr Phe Asp Ala
                85

<210> SEQ ID NO 7
<211> LENGTH: 112
<212> TYPE: PRT
<213> ORGANISM: homo sapiens

<400> SEQUENCE: 7

Asp Lys Asn Thr Thr Gln His Pro Asn Val Thr Thr Leu Ala Pro Ile
1               5                   10                  15

Ser Asn Val Thr Ser Ala Pro Val Thr Ser Leu Pro Leu Val Thr Thr
                20                  25                  30

Pro Ala Pro Asp Glu Ser Tyr Cys Ser His Asn Ser Thr Val Ser Asp
            35                  40                  45

Cys Gln Val Gly Asn Thr Thr Asp Phe Cys Ser Val Ser Thr Ala Thr
        50                  55                  60

Pro Val Pro Thr Ala Asn Ser Thr Ala Lys Pro Thr Val Gln Pro Ser
65                  70                  75                  80

Pro Ser Thr Thr Ser Lys Thr Val Thr Thr Ser Gly Thr Thr Asn Asn
                85                  90                  95

Thr Val Thr Pro Thr Ser Gln Pro Val Arg Lys Ser Thr Phe Asp Ala
            100                 105                 110

<210> SEQ ID NO 8
<211> LENGTH: 127
<212> TYPE: PRT
<213> ORGANISM: homo sapiens

<400> SEQUENCE: 8
```

```
Asp Lys Asn Thr Thr Gln His Pro Asn Val Thr Thr Leu Ala Pro Ile
1               5                   10                  15

Ser Asn Val Thr Ser Ala Pro Val Thr Ser Leu Pro Leu Val Thr Thr
            20                  25                  30

Pro Ala Pro Glu Thr Cys Glu Gly Arg Asn Ser Cys Val Ser Cys Phe
        35                  40                  45

Asn Val Ser Val Val Asn Thr Thr Cys Phe Trp Ile Glu Cys Lys Asp
    50                  55                  60

Glu Ser Tyr Cys Ser His Asn Ser Thr Val Ser Asp Cys Gln Val Gly
65                  70                  75                  80

Asn Thr Thr Asp Phe Cys Ser Ala Lys Pro Thr Val Gln Pro Ser Pro
                85                  90                  95

Ser Thr Thr Ser Lys Thr Val Thr Ser Gly Thr Thr Asn Asn Thr
                100                 105                 110

Val Thr Pro Thr Ser Gln Pro Val Arg Lys Ser Thr Phe Asp Ala
            115                 120                 125
```

<210> SEQ ID NO 9
<211> LENGTH: 87
<212> TYPE: PRT
<213> ORGANISM: homo sapiens

<400> SEQUENCE: 9

```
Asp Lys Asn Thr Thr Gln His Pro Asn Val Thr Thr Leu Ala Pro Ile
1               5                   10                  15

Ser Asn Val Thr Ser Ala Pro Val Thr Ser Leu Pro Leu Val Thr Thr
            20                  25                  30

Pro Ala Pro Glu Thr Cys Glu Gly Arg Asn Ser Cys Val Ser Cys Phe
        35                  40                  45

Asn Val Ser Val Val Asn Thr Thr Cys Phe Trp Ile Glu Cys Lys Asp
    50                  55                  60

Glu Ser Tyr Cys Ser His Asn Ser Thr Val Ser Asp Cys Gln Val Gly
65                  70                  75                  80

Asn Thr Thr Asp Phe Cys Ser
                85
```

<210> SEQ ID NO 10
<211> LENGTH: 108
<212> TYPE: PRT
<213> ORGANISM: homo sapiens

<400> SEQUENCE: 10

```
Asp Lys Asn Thr Thr Gln His Pro Asn Val Thr Thr Leu Ala Pro Ile
1               5                   10                  15

Ser Asn Val Thr Ser Ala Pro Val Thr Ser Leu Pro Leu Val Thr Thr
            20                  25                  30

Pro Ala Pro Glu Thr Cys Glu Gly Arg Asn Ser Cys Val Ser Cys Phe
        35                  40                  45

Asn Val Ser Val Val Asn Thr Thr Cys Phe Trp Ile Glu Cys Lys Asp
    50                  55                  60

Glu Ser Tyr Cys Ser His Asn Ser Thr Val Ser Asp Cys Gln Val Gly
65                  70                  75                  80

Asn Thr Thr Asp Phe Cys Ser Gly Thr Thr Asn Asn Thr Val Thr Pro
                85                  90                  95

Thr Ser Gln Pro Val Arg Lys Ser Thr Phe Asp Ala
            100                 105
```

```
<210> SEQ ID NO 11
<211> LENGTH: 119
<212> TYPE: PRT
<213> ORGANISM: homo sapiens

<400> SEQUENCE: 11

Asp Lys Asn Thr Thr Gln His Pro Asn Val Thr Thr Leu Ala Pro Ile
1               5                   10                  15

Ser Asn Val Thr Ser Ala Pro Val Thr Ser Leu Pro Leu Val Thr Thr
            20                  25                  30

Pro Ala Pro Glu Thr Cys Glu Gly Arg Asn Ser Cys Val Ser Cys Phe
        35                  40                  45

Asn Val Ser Val Val Asn Thr Thr Cys Phe Trp Ile Glu Cys Lys Asp
    50                  55                  60

Glu Ser Tyr Cys Ser His Asn Ser Thr Val Ser Asp Cys Gln Val Gly
65                  70                  75                  80

Asn Thr Thr Asp Phe Cys Ser Val Ser Thr Ala Thr Pro Val Pro Thr
                85                  90                  95

Ala Asn Ser Thr Ala Lys Pro Thr Val Gln Pro Ser Pro Ser Thr Thr
            100                 105                 110

Ser Lys Thr Val Thr Thr Ser
        115

<210> SEQ ID NO 12
<211> LENGTH: 121
<212> TYPE: PRT
<213> ORGANISM: homo sapiens

<400> SEQUENCE: 12

Asp Lys Asn Thr Thr Gln His Pro Asn Val Thr Thr Leu Ala Pro Ile
1               5                   10                  15

Ser Asn Val Thr Ser Ala Pro Val Thr Ser Leu Pro Leu Val Thr Thr
            20                  25                  30

Pro Ala Pro Glu Thr Cys Glu Gly Arg Asn Ser Cys Val Ser Cys Phe
        35                  40                  45

Asn Val Ser Val Val Asn Thr Thr Cys Phe Trp Ile Glu Cys Lys Asp
    50                  55                  60

Glu Ser Tyr Cys Ser His Asn Ser Thr Val Ser Asp Cys Gln Val Gly
65                  70                  75                  80

Asn Thr Thr Asp Phe Cys Ser Val Ser Thr Ala Thr Pro Val Pro Thr
                85                  90                  95

Ala Asn Ser Thr Gly Thr Thr Asn Asn Thr Val Thr Pro Thr Ser Gln
            100                 105                 110

Pro Val Arg Lys Ser Thr Phe Asp Ala
        115                 120

<210> SEQ ID NO 13
<211> LENGTH: 140
<212> TYPE: PRT
<213> ORGANISM: homo sapiens

<400> SEQUENCE: 13

Asp Lys Asn Thr Thr Gln His Pro Asn Val Thr Thr Leu Ala Pro Ile
1               5                   10                  15

Ser Asn Val Thr Ser Glu Pro Val Thr Ser Leu Pro Leu Val Thr Thr
            20                  25                  30

Pro Ala Pro Glu Thr Cys Glu Gly Arg Asn Ser Cys Val Ser Cys Phe
```

```
                35                  40                  45
Asn Val Ser Val Val Asn Thr Thr Cys Phe Trp Ile Glu Cys Lys Asp
 50                  55                  60

Glu Ser Tyr Cys Ser His Asn Ser Thr Val Ser Asp Cys Gln Val Glu
 65                  70                  75                  80

Asn Thr Thr Asp Phe Cys Ser Val Ser Thr Ala Thr Pro Val Pro Thr
                 85                  90                  95

Ala Asn Ser Thr Ala Lys Pro Thr Val Gln Pro Ser Pro Ser Thr Thr
                100                 105                 110

Ser Lys Thr Val Thr Thr Ser Gly Thr Thr Asn Asn Thr Val Thr Pro
            115                 120                 125

Thr Ser Gln Pro Val Arg Lys Ser Thr Phe Asp Ala
            130                 135                 140

<210> SEQ ID NO 14
<211> LENGTH: 140
<212> TYPE: PRT
<213> ORGANISM: homo sapiens

<400> SEQUENCE: 14

Asp Lys Asn Thr Thr Gln His Pro Ala Val Thr Thr Leu Ala Pro Ile
 1               5                  10                  15

Ser Ala Val Thr Ser Ala Pro Val Thr Ser Leu Pro Leu Val Thr Thr
                20                  25                  30

Pro Ala Pro Glu Thr Cys Glu Gly Arg Asn Ser Cys Val Ser Cys Phe
                35                  40                  45

Asn Val Ser Val Val Asn Thr Thr Cys Phe Trp Ile Glu Cys Lys Asp
 50                  55                  60

Glu Ser Tyr Cys Ser His Asn Ser Thr Val Ser Asp Cys Gln Val Gly
 65                  70                  75                  80

Asn Thr Thr Asp Phe Cys Ser Val Ser Thr Ala Thr Pro Val Pro Thr
                 85                  90                  95

Ala Asn Ser Thr Ala Lys Pro Thr Val Gln Pro Ser Pro Ser Thr Thr
                100                 105                 110

Ser Lys Thr Val Thr Thr Ser Gly Thr Thr Asn Asn Thr Val Thr Pro
            115                 120                 125

Thr Ser Gln Pro Val Arg Lys Ser Thr Phe Asp Ala
            130                 135                 140

<210> SEQ ID NO 15
<211> LENGTH: 140
<212> TYPE: PRT
<213> ORGANISM: homo sapiens

<400> SEQUENCE: 15

Asp Lys Asn Thr Thr Gln His Pro Asn Val Thr Thr Leu Ala Pro Ile
 1               5                  10                  15

Ser Asn Val Thr Ser Ala Pro Val Thr Ser Leu Pro Leu Val Thr Thr
                20                  25                  30

Pro Ala Pro Glu Thr Cys Glu Gly Arg Asn Ser Cys Val Ser Cys Phe
                35                  40                  45

Asn Val Ser Val Val Asn Thr Thr Cys Phe Trp Ile Glu Cys Lys Asp
 50                  55                  60

Glu Ser Tyr Cys Ser His Asn Ser Thr Val Ser Asp Cys Gln Val Gly
 65                  70                  75                  80

Asn Thr Thr Asp Phe Cys Ser Val Ser Thr Ala Thr Pro Val Pro Thr
```

-continued

```
                    85                  90                  95
Ala Asn Ser Thr Ala Lys Pro Thr Val Gln Pro Ser Pro Ser Thr Thr
                100                 105                 110

Ser Lys Thr Val Thr Thr Ser Gly Thr Thr Asn Asn Thr Val Thr Pro
            115                 120                 125

Thr Ser Gln Pro Val Arg Lys Ser Thr Phe Asp Ala
        130                 135                 140

<210> SEQ ID NO 16
<211> LENGTH: 372
<212> TYPE: PRT
<213> ORGANISM: homo sapiens

<400> SEQUENCE: 16

Asp Lys Asn Thr Thr Gln His Pro Asn Val Thr Thr Leu Ala Pro Ile
1               5                   10                  15

Ser Asn Val Thr Ser Ala Pro Val Thr Ser Leu Pro Leu Val Thr Thr
            20                  25                  30

Pro Ala Pro Glu Thr Cys Glu Gly Arg Asn Ser Cys Val Ser Cys Phe
        35                  40                  45

Asn Val Ser Val Val Asn Thr Thr Cys Phe Trp Ile Glu Cys Lys Asp
    50                  55                  60

Glu Ser Tyr Cys Ser His Asn Ser Thr Val Ser Asp Cys Gln Val Gly
65                  70                  75                  80

Asn Thr Thr Asp Phe Cys Ser Val Ser Thr Ala Thr Pro Val Pro Thr
                85                  90                  95

Ala Asn Ser Thr Ala Lys Pro Thr Val Gln Pro Ser Pro Ser Thr Thr
                100                 105                 110

Ser Lys Thr Val Thr Thr Ser Gly Thr Thr Asn Asn Thr Val Thr Pro
            115                 120                 125

Thr Ser Gln Pro Val Arg Lys Ser Thr Phe Asp Ala Glu Pro Lys Ser
        130                 135                 140

Cys Asp Lys Thr His Thr Cys Pro Pro Cys Pro Ala Pro Glu Leu Leu
145                 150                 155                 160

Gly Gly Pro Ser Val Phe Leu Phe Pro Pro Lys Pro Lys Asp Thr Leu
                165                 170                 175

Met Ile Ser Arg Thr Pro Glu Val Thr Cys Val Val Val Asp Val Ser
            180                 185                 190

His Glu Asp Pro Glu Val Lys Phe Asn Trp Tyr Val Asp Gly Val Glu
        195                 200                 205

Val His Asn Ala Lys Thr Lys Pro Arg Glu Glu Gln Tyr Asn Ser Thr
    210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                245                 250                 255

Ile Glu Lys Thr Ile Ser Lys Ala Lys Gly Gln Pro Arg Glu Pro Gln
            260                 265                 270

Val Tyr Thr Leu Pro Pro Ser Arg Glu Glu Met Thr Lys Asn Gln Val
        275                 280                 285

Ser Leu Thr Cys Leu Val Lys Gly Phe Tyr Pro Ser Asp Ile Ala Val
    290                 295                 300

Glu Trp Glu Ser Asn Gly Gln Pro Glu Asn Asn Tyr Lys Thr Thr Pro
305                 310                 315                 320
```

```
Pro Val Leu Asp Ser Asp Gly Ser Phe Phe Leu Tyr Ser Lys Leu Thr
                325                 330                 335

Val Asp Lys Ser Arg Trp Gln Gln Gly Asn Val Phe Ser Cys Ser Val
            340                 345                 350

Met His Glu Ala Leu His Asn His Tyr Thr Gln Lys Ser Leu Ser Leu
        355                 360                 365

Ser Pro Gly Lys
        370

<210> SEQ ID NO 17
<211> LENGTH: 197
<212> TYPE: PRT
<213> ORGANISM: homo sapiens

<400> SEQUENCE: 17

Met Ser Arg Leu Ser Arg Ser Leu Leu Trp Ala Ala Thr Cys Leu Gly
1               5                   10                  15

Val Leu Cys Val Leu Ser Ala Asp Lys Asn Thr Thr Gln His Pro Asn
                20                  25                  30

Val Thr Thr Leu Ala Pro Ile Ser Asn Val Thr Ser Ala Pro Val Thr
            35                  40                  45

Ser Leu Pro Leu Val Thr Thr Pro Ala Pro Glu Thr Cys Glu Gly Arg
        50                  55                  60

Asn Ser Cys Val Ser Cys Phe Asn Val Ser Val Asn Thr Thr Cys
65                  70                  75                  80

Phe Trp Ile Glu Cys Lys Asp Glu Ser Tyr Cys Ser His Asn Ser Thr
                85                  90                  95

Val Ser Asp Cys Gln Val Gly Asn Thr Thr Asp Phe Cys Ser Val Ser
                100                 105                 110

Thr Ala Thr Pro Val Pro Thr Ala Asn Ser Thr Ala Lys Pro Thr Val
            115                 120                 125

Gln Pro Ser Pro Ser Thr Thr Ser Lys Thr Val Thr Thr Ser Gly Thr
        130                 135                 140

Thr Asn Asn Thr Val Thr Pro Thr Ser Gln Pro Val Arg Lys Ser Thr
145                 150                 155                 160

Phe Asp Ala Ala Ser Phe Ile Gly Gly Ile Val Leu Val Leu Gly Val
                165                 170                 175

Gln Ala Val Ile Phe Phe Leu Tyr Lys Phe Cys Lys Ser Lys Glu Arg
                180                 185                 190

Asn Tyr His Thr Leu
        195

<210> SEQ ID NO 18
<211> LENGTH: 372
<212> TYPE: PRT
<213> ORGANISM: Homo sapiens

<400> SEQUENCE: 18

Asp Lys Asn Thr Thr Gln His Pro Asn Val Thr Thr Leu Ala Pro Ile
1               5                   10                  15

Ser Asn Val Thr Ser Ala Pro Val Thr Ser Leu Pro Leu Val Thr Thr
                20                  25                  30

Pro Ala Pro Glu Thr Cys Glu Gly Arg Asn Ser Cys Val Ser Cys Phe
            35                  40                  45

Asn Val Ser Val Val Asn Thr Thr Cys Phe Trp Ile Glu Cys Lys Asp
        50                  55                  60
```

-continued

```
Glu Ser Tyr Cys Ser His Asn Ser Thr Val Ser Asp Cys Gln Val Gly
 65                  70                  75                  80

Asn Thr Thr Asp Phe Cys Ser Val Ser Thr Ala Thr Pro Val Pro Thr
                 85                  90                  95

Ala Asn Ser Thr Ala Lys Pro Thr Val Gln Pro Ser Pro Ser Thr Thr
            100                 105                 110

Ser Lys Thr Val Thr Thr Ser Gly Thr Thr Asn Asn Thr Val Thr Pro
        115                 120                 125

Thr Ser Gln Pro Val Arg Lys Ser Thr Phe Asp Ala Glu Pro Lys Ser
    130                 135                 140

Cys Asp Lys Thr His Thr Cys Pro Pro Cys Pro Ala Pro Glu Ala Glu
145                 150                 155                 160

Gly Ala Pro Ser Val Phe Leu Phe Pro Pro Lys Pro Lys Asp Thr Leu
                165                 170                 175

Met Ile Ser Arg Thr Pro Glu Val Thr Cys Val Val Val Asp Val Ser
            180                 185                 190

His Glu Asp Pro Glu Val Lys Phe Asn Trp Tyr Val Asp Gly Val Glu
        195                 200                 205

Val His Asn Ala Lys Thr Lys Pro Arg Glu Glu Gln Tyr Asn Ser Thr
    210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ser Ser
                245                 250                 255

Ile Glu Lys Thr Ile Ser Lys Ala Lys Gly Gln Pro Arg Glu Pro Gln
            260                 265                 270

Val Tyr Thr Leu Pro Pro Ser Arg Glu Glu Met Thr Lys Asn Gln Val
        275                 280                 285

Ser Leu Thr Cys Leu Val Lys Gly Phe Tyr Pro Ser Asp Ile Ala Val
    290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
                325                 330                 335

Val Asp Lys Ser Arg Trp Gln Gln Gly Asn Val Phe Ser Cys Ser Val
            340                 345                 350

Met His Glu Ala Leu His Asn His Tyr Thr Gln Lys Ser Leu Ser Leu
        355                 360                 365

Ser Pro Gly Lys
    370
```